(12) United States Patent
Couture et al.

(10) Patent No.: US 12,364,544 B2
(45) Date of Patent: Jul. 22, 2025

(54) SOFT TISSUE BALANCING IN ARTICULAR SURGERY

(71) Applicant: Zimmer, Inc., Warsaw, IN (US)

(72) Inventors: Pierre Couture, Montreal (CA); Alain Richard, Lachine (CA); Olivier Boisvert, Montreal (CA); Emily Gogarty, Montreal (CA); Louis-Philippe Amiot, Montreal (CA); Sebastien Parratte, Marseilles (FR); Di Li, LaSalle (CA); Dugal James, Bendigo (AU)

(73) Assignee: Zimmer, Inc., Warsaw, IN (US)

( * ) Notice: Subject to any disclaimer, the term of this patent is extended or adjusted under 35 U.S.C. 154(b) by 754 days.

(21) Appl. No.: 17/469,415

(22) Filed: Sep. 8, 2021

(65) Prior Publication Data

US 2022/0096166 A1 Mar. 31, 2022

Related U.S. Application Data

(63) Continuation of application No. 16/166,795, filed on Oct. 22, 2018, now Pat. No. 11,135,021, which is a
(Continued)

(51) Int. Cl.
*A61B 34/20* (2016.01)
*A61B 5/00* (2006.01)
(Continued)

(52) U.S. Cl.
CPC ............ *A61B 34/20* (2016.02); *A61B 5/4585* (2013.01); *A61B 17/1675* (2013.01);
(Continued)

(58) Field of Classification Search
CPC ............ A61B 34/20; A61B 2034/2055; A61B 2034/2068; A61B 2034/2074;
(Continued)

(56) References Cited

U.S. PATENT DOCUMENTS

| 5,682,886 A | 11/1997 | Delp et al. |
| 6,478,753 B2 | 11/2002 | Reay-young |

(Continued)

FOREIGN PATENT DOCUMENTS

| AU | 2019204049 A1 | 7/2019 |
| CA | 3072502 | 9/2023 |

(Continued)

OTHER PUBLICATIONS

"U.S. Appl. No. 17/559,971, Non Final Office Action mailed Dec. 1, 2022", 19 pgs.
(Continued)

*Primary Examiner* — Matthew J Lawson
(74) *Attorney, Agent, or Firm* — SCHWEGMAN LUNDBERG & WOESSNER, P.A.

(57) ABSTRACT

Systems and methods may be used to perform robot-aided surgery. A system may include a robotic controller to monitor a position and orientation of an end effector coupled to an end of a robotic arm. The robotic controller may apply a force to a bone using the end effector, such as via a soft tissue balancing component. The robotic controller may determine soft tissue balance using information from a tracking system, such as a position of a first tracker affixed to the bone. The soft tissue balance may be output, such as to a display device.

20 Claims, 42 Drawing Sheets

Related U.S. Application Data continuation of application No. 15/624,621, filed on Jun. 15, 2017, now Pat. No. 10,136,952.

(60) Provisional application No. 62/501,585, filed on May 4, 2017, provisional application No. 62/424,732, filed on Nov. 21, 2016, provisional application No. 62/375,049, filed on Aug. 15, 2016, provisional application No. 62/350,958, filed on Jun. 16, 2016.

(51) Int. Cl.
*A61B 17/02* (2006.01)
*A61B 17/16* (2006.01)
*A61B 34/00* (2016.01)
*A61B 34/10* (2016.01)
*A61B 34/30* (2016.01)
*A61G 13/12* (2006.01)
*A61B 5/11* (2006.01)
*A61B 90/00* (2016.01)
*A61G 13/00* (2006.01)

(52) U.S. Cl.
CPC ............. *A61B 34/10* (2016.02); *A61B 34/25* (2016.02); *A61B 34/30* (2016.02); *A61B 5/1114* (2013.01); *A61B 5/1121* (2013.01); *A61B 5/1127* (2013.01); *A61B 2017/0268* (2013.01); *A61B 2034/104* (2016.02); *A61B 2034/105* (2016.02); *A61B 2034/108* (2016.02); *A61B 2034/2048* (2016.02); *A61B 2034/2055* (2016.02); *A61B 2034/2068* (2016.02); *A61B 2034/2074* (2016.02); *A61B 2034/252* (2016.02); *A61B 2034/254* (2016.02); *A61B 2090/064* (2016.02); *A61B 2090/067* (2016.02); *A61B 2090/3916* (2016.02); *A61B 2505/05* (2013.01); *A61B 2562/0252* (2013.01); *A61G 13/0063* (2016.11); *A61G 13/1245* (2013.01); *A61G 13/125* (2013.01)

(58) Field of Classification Search
CPC ... A61B 34/25; A61B 34/30; A61B 2034/104; A61B 2034/252; A61B 17/1626; A61B 17/1703; A61B 17/1707; A61B 17/1764; A61B 17/025; A61B 2017/0268
See application file for complete search history.

(56) References Cited

U.S. PATENT DOCUMENTS

| | | |
|---|---|---|
| 7,615,055 B2 | 11/2009 | DiSilvestro |
| 8,007,448 B2 | 8/2011 | Moctesuma de la Barrera |
| 8,065,927 B2 | 11/2011 | Crottet et al. |
| 8,323,290 B2 | 12/2012 | Metzger et al. |
| 8,337,508 B2 | 12/2012 | Lavallee et al. |
| 8,394,104 B2 | 3/2013 | DiSilvestro |
| 8,556,830 B2 | 10/2013 | Sherman et al. |
| 8,571,637 B2 | 10/2013 | Sheffer et al. |
| 8,734,454 B2 | 5/2014 | DiSilvestro |
| 8,888,718 B2 | 11/2014 | Siston et al. |
| 9,259,172 B2 | 2/2016 | Stein et al. |
| 9,265,447 B2 | 2/2016 | Stein et al. |
| 9,585,615 B2 | 3/2017 | Singh et al. |
| 9,622,701 B2 | 4/2017 | Stein et al. |
| 9,636,185 B2 | 5/2017 | Quaid et al. |
| 10,136,952 B2 | 11/2018 | Couture et al. |
| 10,206,792 B2 | 2/2019 | Sherman et al. |
| 10,729,417 B2 | 8/2020 | Cole et al. |
| 10,758,375 B2 | 9/2020 | Walker et al. |
| 10,973,659 B2 | 4/2021 | Cabot |
| 11,135,021 B2 | 10/2021 | Couture et al. |
| 11,229,489 B2 | 1/2022 | Merette et al. |
| 11,707,333 B2 | 7/2023 | Merette et al. |
| 2002/0052606 A1 | 5/2002 | Bonutti |
| 2003/0069644 A1 | 4/2003 | Kovacevic et al. |
| 2003/0153978 A1 | 8/2003 | Whiteside |
| 2004/0030245 A1 | 2/2004 | Noble et al. |
| 2004/0097951 A1 | 5/2004 | Steffensmeier |
| 2004/0111183 A1* | 6/2004 | Sutherland ............. A61B 34/76 700/245 |
| 2004/0254771 A1 | 12/2004 | Riener et al. |
| 2006/0142657 A1 | 6/2006 | Quaid et al. |
| 2006/0149277 A1 | 7/2006 | Cinquin et al. |
| 2006/0241569 A1 | 10/2006 | Disilvestro |
| 2007/0066917 A1* | 3/2007 | Hodorek ................ A61B 90/36 600/595 |
| 2007/0100258 A1* | 5/2007 | Shoham ............... A61B 17/157 606/86 R |
| 2007/0156157 A1 | 7/2007 | Nahum et al. |
| 2007/0179626 A1 | 8/2007 | de la Barrera et al. |
| 2007/0244488 A1 | 10/2007 | Metzger et al. |
| 2007/0270680 A1 | 11/2007 | Sheffer et al. |
| 2009/0043556 A1* | 2/2009 | Axelson ................ A61B 90/36 600/416 |
| 2009/0171371 A1* | 7/2009 | Nixon .................... A61B 34/37 700/264 |
| 2010/0010506 A1 | 1/2010 | Murphy |
| 2010/0198275 A1 | 8/2010 | Chana et al. |
| 2010/0198402 A1* | 8/2010 | Greer ........................ B25J 3/04 901/41 |
| 2010/0234770 A1 | 9/2010 | Colombet et al. |
| 2010/0249533 A1 | 9/2010 | Pierce et al. |
| 2010/0250571 A1 | 9/2010 | Pierce et al. |
| 2011/0130761 A1* | 6/2011 | Plaskos ................. A61B 34/10 606/87 |
| 2011/0196377 A1* | 8/2011 | Hodorek ............... A61B 17/157 606/87 |
| 2011/0257653 A1* | 10/2011 | Hughes ................. A61B 34/10 606/86 R |
| 2011/0275957 A1 | 11/2011 | Bhandari |
| 2012/0259342 A1 | 10/2012 | Chana et al. |
| 2012/0290088 A1 | 11/2012 | Amirouche et al. |
| 2013/0023794 A1 | 1/2013 | Stein et al. |
| 2013/0066432 A1 | 3/2013 | Colwell et al. |
| 2013/0296868 A1 | 11/2013 | Bonutti |
| 2014/0188129 A1 | 7/2014 | Kang |
| 2014/0189508 A1* | 7/2014 | Granchi ................ A61B 34/10 715/705 |
| 2014/0228860 A1 | 8/2014 | Steines et al. |
| 2015/0094736 A1 | 4/2015 | Malackowski et al. |
| 2015/0105782 A1 | 4/2015 | D'lima et al. |
| 2015/0106024 A1 | 4/2015 | Lightcap et al. |
| 2015/0164609 A1 | 6/2015 | Wu |
| 2015/0182288 A1* | 7/2015 | Greenwald ............ A61B 34/20 606/279 |
| 2015/0265291 A1 | 9/2015 | Wilkinson |
| 2015/0305828 A1* | 10/2015 | Park ....................... A61B 34/30 345/629 |
| 2015/0374446 A1* | 12/2015 | Malackowski ........ A61B 34/20 606/130 |
| 2016/0045268 A1 | 2/2016 | Keppler et al. |
| 2016/0081758 A1 | 3/2016 | Bonutti |
| 2016/0095694 A1 | 4/2016 | Hauri et al. |
| 2016/0228193 A1* | 8/2016 | Moctezuma de la Barrera ......... A61F 2/38 |
| 2016/0278944 A1 | 9/2016 | D'lima et al. |
| 2016/0343273 A1* | 11/2016 | Stuart .................... B25J 9/1676 |
| 2017/0312099 A1 | 11/2017 | Paszicsnyek |
| 2017/0360512 A1 | 12/2017 | Couture et al. |
| 2018/0132949 A1 | 5/2018 | Merette et al. |
| 2019/0053859 A1 | 2/2019 | Couture et al. |
| 2019/0290451 A1 | 9/2019 | Trabish et al. |
| 2020/0261297 A1 | 8/2020 | Strydom et al. |
| 2020/0323540 A1 | 10/2020 | Kang et al. |
| 2021/0000612 A1 | 1/2021 | Mahfouz |

(56) References Cited

U.S. PATENT DOCUMENTS

| | | | |
|---|---|---|---|
| 2021/0007809 | A1 | 1/2021 | Morgan |
| 2022/0183774 | A1 | 6/2022 | Merette et al. |

FOREIGN PATENT DOCUMENTS

| | | | |
|---|---|---|---|
| CN | 101375797 | A | 3/2009 |
| CN | 101612055 | A | 12/2009 |
| CN | 105011997 | A | 11/2015 |
| CN | 105592817 | A | 5/2016 |
| CN | 109640862 | A | 4/2019 |
| CN | 110623732 | A | 12/2019 |
| EP | 0204639 | B1 | 10/1990 |
| ES | 2341267 | T3 | 6/2010 |
| JP | 2007152100 | A | 6/2007 |
| JP | 2007202950 | A | 8/2007 |
| JP | 2008517708 | A | 5/2008 |
| JP | 2010240406 | A | 10/2010 |
| JP | 2019521755 | A | 8/2019 |
| JP | 2020044443 | A | 3/2020 |
| WO | WO-2013020026 | A1 | 2/2013 |
| WO | WO-2017195046 | A2 | 11/2017 |
| WO | WO-2017218928 | A1 | 12/2017 |

OTHER PUBLICATIONS

"Canadian Application Serial No. 3,072,502, Response filed Jan. 12, 2023 to Office Action mailed Sep. 27, 2022", 15 pgs.
"U.S. Appl. No. 17/559,971, Response filed Feb. 24, 2023 to Non Final Office Action mailed Dec. 1, 2022", 11 pgs.
"U.S. Appl. No. 17/559,971, Notice of Allowance mailed Mar. 8, 2023", 7 pgs.
"Australian Application Serial No. 2023200636, First Examination Report mailed Jan. 8, 2024", 2 pgs.
"European Application Serial No. 17734204.5, Communication Pursuant to Article 94(3) EPC mailed Feb. 13, 2024", 6 pgs.
"U.S. Appl. No. 15/624,621, Advisory Action mailed Jul. 6, 2018", 3 pgs.
"U.S. Appl. No. 15/624,621, Examiner Interview Summary mailed Dec. 18, 2017", 3 pgs.
"U.S. Appl. No. 15/624,621, Final Office Action mailed Apr. 26, 2018", 14 pgs.
"U.S. Appl. No. 15/624,621, Non Final Office Action mailed Oct. 20, 2017", 12 pgs.
"U.S. Appl. No. 15/624,621, Notice of Allowance mailed Jul. 23, 2018", 5 pgs.
"U.S. Appl. No. 15/624,621, Response filed Jan. 17, 2018 to Non Final Office Action mailed Oct. 20, 2017", 14 pgs.
"U.S. Appl. No. 15/624,621, Response filed Jun. 25, 2018 to Final Office Action mailed Apr. 26, 2018", 10 pgs.
"U.S. Appl. No. 15/624,621, Response filed Jul. 13, 2018 to Advisory Action mailed Jul. 16, 2018", 5 pgs.
"U.S. Appl. No. 15/624,621, Response filed Sep. 27, 2017 to Restriction Requirement mailed Sep. 13, 2017", 9 pgs.
"U.S. Appl. No. 15/624,621, Restriction Requirement mailed Sep. 13, 2017", 8 pgs.
"U.S. Appl. No. 15/853,657, Corrected Notice of Allowability mailed Dec. 22, 2021", 4 pgs.
"U.S. Appl. No. 15/853,657, Final Office Action mailed Dec. 22, 2020", 21 pgs.
"U.S. Appl. No. 15/853,657, Non Final Office Action mailed May 6, 2021", 20 pgs.
"U.S. Appl. No. 15/853,657, Non Final Office Action mailed Jun. 11, 2020", 15 pgs.
"U.S. Appl. No. 15/853,657, Notice of Allowance mailed Sep. 21, 2021", 7 pgs.
"U.S. Appl. No. 15/853,657, Response filed Mar. 9, 2020 to Restriction Requirement mailed Jan. 7, 2020", 7 pgs.
"U.S. Appl. No. 15/853,657, Response filed Mar. 19, 2021 to Final Office Action mailed Dec. 22, 2020", 11 pgs.
"U.S. Appl. No. 15/853,657, Response filed Aug. 5, 2021 to Non Final Office Action mailed May 6, 2021", 10 pages.
"U.S. Appl. No. 15/853,657, Response filed Sep. 11, 2020 to Non Final Office Action mailed Jun. 11, 2020", 10 pgs.
"U.S. Appl. No. 15/853,657, Restriction Requirement mailed Jan. 7, 2020", 6 pgs.
"U.S. Appl. No. 16/166,795, Advisory Action mailed Feb. 11, 2021", 2 pgs.
"U.S. Appl. No. 16/166,795, Corrected Notice of Allowability mailed Jun. 16, 2021", 2 pgs.
"U.S. Appl. No. 16/166,795, Final Office Action mailed Nov. 9, 2020", 7 pgs.
"U.S. Appl. No. 16/166,795, Non Final Office Action mailed Jul. 27, 2020", 9 pgs.
"U.S. Appl. No. 16/166,795, Notice of Allowance mailed Jun. 2, 2021", 6 pgs.
"U.S. Appl. No. 16/166,795, Preliminary Amendment filed Nov. 8, 2018", 6 pgs.
"U.S. Appl. No. 16/166,795, Response filed Jan. 11, 2021 to Final Office Action mailed Nov. 9, 2020", 10 pgs.
"U.S. Appl. No. 16/166,795, Response filed Mar. 9, 2021 to Advisory Action mailed Feb. 11, 2021", 10 pgs.
"U.S. Appl. No. 16/166,795, Response filed Jul. 2, 2020 to Restriction Requirement mailed May 5, 2020", 9 pgs.
"U.S. Appl. No. 16/166,795, Response filed Oct. 27, 2020 to Non Final Office Action mailed Jul. 27, 2020", 9 pgs.
"U.S. Appl. No. 16/166,795, Restriction Requirement mailed May 5, 2020", 7 pgs.
"Australian Application Serial No. 2017283630, First Examination Report mailed Jan. 17, 2019", 4 pgs.
"Australian Application Serial No. 2018282467, First Examination Report mailed Jan. 28, 2020", 12 pgs.
"Australian Application Serial No. 2019204049, First Examination Report mailed Mar. 6, 2020", 6 pgs.
"Australian Application Serial No. 2019204049, Response filed Jul. 27, 2020 to First Examination Report mailed Mar. 6, 2020", 17 pgs.
"Australian Application Serial No. 2019204049, Response filed Nov. 9, 2020 to Subsequent Examiners Report mailed Aug. 24, 2020", 17 pgs.
"Australian Application Serial No. 2019204049, Subsequent Examiners Report mailed Aug. 24, 2020", 3 pgs.
"Canadian Application Serial No. 3,026,416, Examiner's Rule 30(2) Requisition mailed Jan. 22, 2019", 4 pgs.
"Canadian Application Serial No. 3,026,416, Response filed Jul. 22, 2019 to Examiner's Rule 30(2) Requisition mailed Jan. 22, 2019", 4 pgs.
"Canadian Application Serial No. 3,072,502, Office Action mailed Mar. 3, 2021", 3 pgs.
"Canadian Application Serial No. 3,072,502, Office Action mailed Sep. 2, 2021", 3 pgs.
"Canadian Application Serial No. 3,072,502, Response filed Jul. 5, 2021 to Office Action mailed Mar. 3, 2021", 15 pgs.
"Chinese Application Serial No. 201780037103.7, Office Action mailed Jun. 27, 2019", w/ English translation, 8 pgs.
"Chinese Application Serial No. 201780037103.7, Response filed Aug. 9, 2019 to Office Action mailed Jun. 27, 2019", w/English claims, 6 pgs.
"De Mayo Universal Distractor®", Innovative Medical Products, Inc., (2013), 2 pgs.
"European Application Serial No. 17734204.5, Response filed Aug. 8, 2019 to Office Action mailed Jan. 29, 2019", 25 pgs.
"European Application Serial No. 18215519.2, Extended European Search Report mailed Jul. 30, 2019", 7 pgs.
"European Application Serial No. 18215519.2, Response filed Feb. 28, 2020 to Extended European Search Report mailed Jul. 30, 2019", 23 pgs.
"International Application Serial No. PCT/US2017/037930, International Preliminary Report on Patentability mailed Dec. 27, 2018", 13 pgs.
"International Application Serial No. PCT/US2017/037930, International Search Report mailed Sep. 26, 2017", 5 pgs.
"International Application Serial No. PCT/US2017/037930, Written Opinion mailed Sep. 26, 2017", 11 pgs.

(56) References Cited

OTHER PUBLICATIONS

"Japanese Application Serial No. 2018-565863, Notification of Reasons for Refusal mailed Jul. 16, 2019", w/ English Translation, 8 pgs.

"Japanese Application Serial No. 2018-565863, Response filed Oct. 10, 2019 to Notification of Reasons for Refusal mailed Jul. 16, 2019", (W/ English Translation of Claims), 15 pgs.

"Japanese Application Serial No. 2019-236315, Examiners Decision of Final Refusal mailed Jul. 27, 2021", w/ English translation, 5 pages.

"Japanese Application Serial No. 2019-236315, Notification of Reasons for Refusal mailed Mar. 2, 2021", with English translation, 9 pages.

"Japanese Application Serial No. 2019-236315, Response filed Jun. 2, 2021 to Notification of Reasons for Refusal mailed Mar. 2, 2021", (W/ English Translation), 27 pgs.

"Surgical Technique for Use With The Journey II BCS and Journey II CR.", Smith-nephew.com, <https://www.smithnephew.com/global/assets/pdf/products/surgical/navio_tka_st_manual_5 00081revb.pdf>, (2011).

Fickert, S, et al., "Precision of Ci-Navigated Extension and Flexion Gap Balancing in Total Knee Arthroplasty and Analysis of Potential Predictive Variables", Archives of Orthopaedic and Trauma Surgery, U.S. National Library of Medicine, (Nov. 2011).

"U.S. Appl. No. 17/559,971, Preliminary Amendment filed Mar. 3, 2022", 7 pgs.

"Australian Application Serial No. 2021202048, First Examination Report mailed Feb. 25, 2022"; 2 pgs.

"Australian Application Serial No. 2021202048, Response filed Sep. 29, 2022 to First Examination Report mailed Feb. 25, 2022", 10 pgs.

"Canadian Application Serial No. 3,072,502, Office Action mailed Sep. 27, 2022", 3 pgs.

"Canadian Application Serial No. 3,072,502, Response filed Dec. 30, 2021 to Office Action mailed Sep. 2, 2021", 13 pgs.

"Chinese Application Serial No. 201911065681.9, Office Action mailed Mar. 16, 2022", w/ English Translation, 17 pgs.

"Chinese Application Serial No. 201911065681.9, Office Action mailed Aug. 8, 2022", w/ English Translation, 14 pgs.

"Chinese Application Serial No. 201911065681.9, Response filed Jul. 4, 2022 to Office Action mailed Mar. 16, 2022", w/ English claims, 55 pgs.

"Chinese Application Serial No. 201911065681.9, Response filed Sep. 27, 2022 to Office Action mailed Aug. 8, 2022", w/ English claims, 12 pgs.

"Chinese Application Serial No. 201911065681.9, Response filed Oct. 26, 2022", w/ English claims, 5 pgs.

"European Application Serial No. 17734204.5, Communication Pursuant to Article 94(3) EPC mailed Jun. 30, 2022", 7 pgs.

U.S. Appl. No. 15/624,621 U.S. Pat. No. 10,136,952, filed Jun. 15, 2017, Soft Tissue Balancing in Articular Surgery.

U.S. Appl. No. 16/166,795 U.S. Pat. No. 11,135,021, filed Oct. 22, 2018, Soft Tissue Balancing in Articular Surgery.

U.S. Appl. No. 15/853,657, filed Dec. 22, 2017, Soft Tissue Balancing in Articular Surgery.

U.S. Appl. No. 17/559,971, filed Dec. 22, 2021, Soft Tissue Balancing in Articular Surgery.

"Australian Application Serial No. 2023200636, Response filed Jun. 5, 2024 to First Examination Report mailed Jan. 8, 2024", 15 pgs.

"Australian Application Serial No. 2023200636, Response filed Oct. 14, 2024 to Subsequent Examination Report mailed Jul. 23, 2024", 16 pgs.

"Australian Application Serial No. 2023200636, Subsequent Examination Report mailed Jul. 23, 2024", 4 pgs.

"Canadian Application Serial No. 3,187,070, Office Action mailed Jun. 25, 2024", 3 pgs.

"Canadian Application Serial No. 3, 187,070, Examiners Rule 86(2) Report mailed Jun. 2, 2025", 4 pgs.

\* cited by examiner

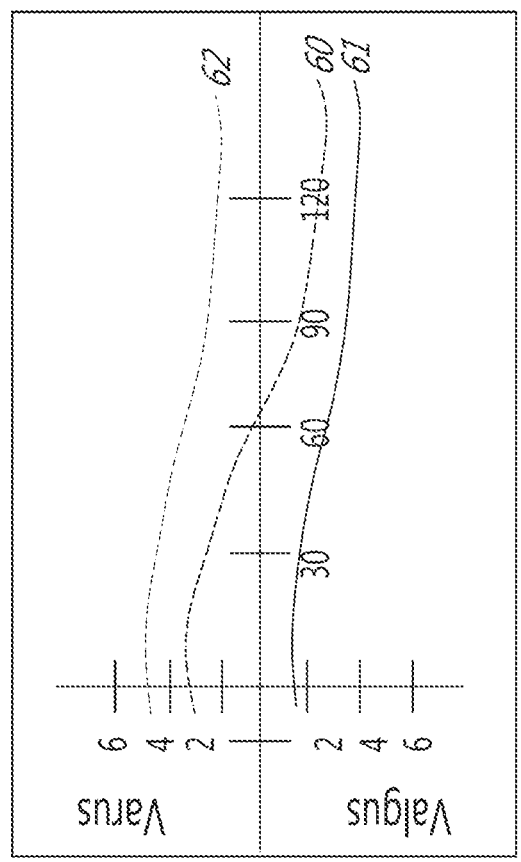
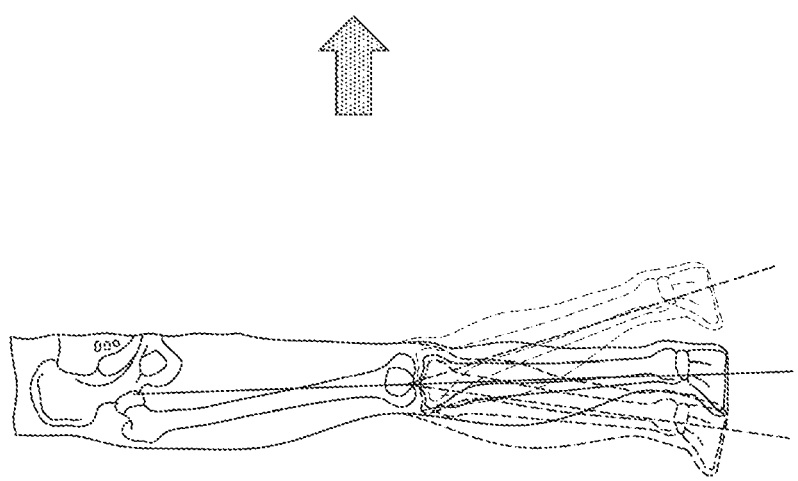
FIG. 17A
FIG. 17B

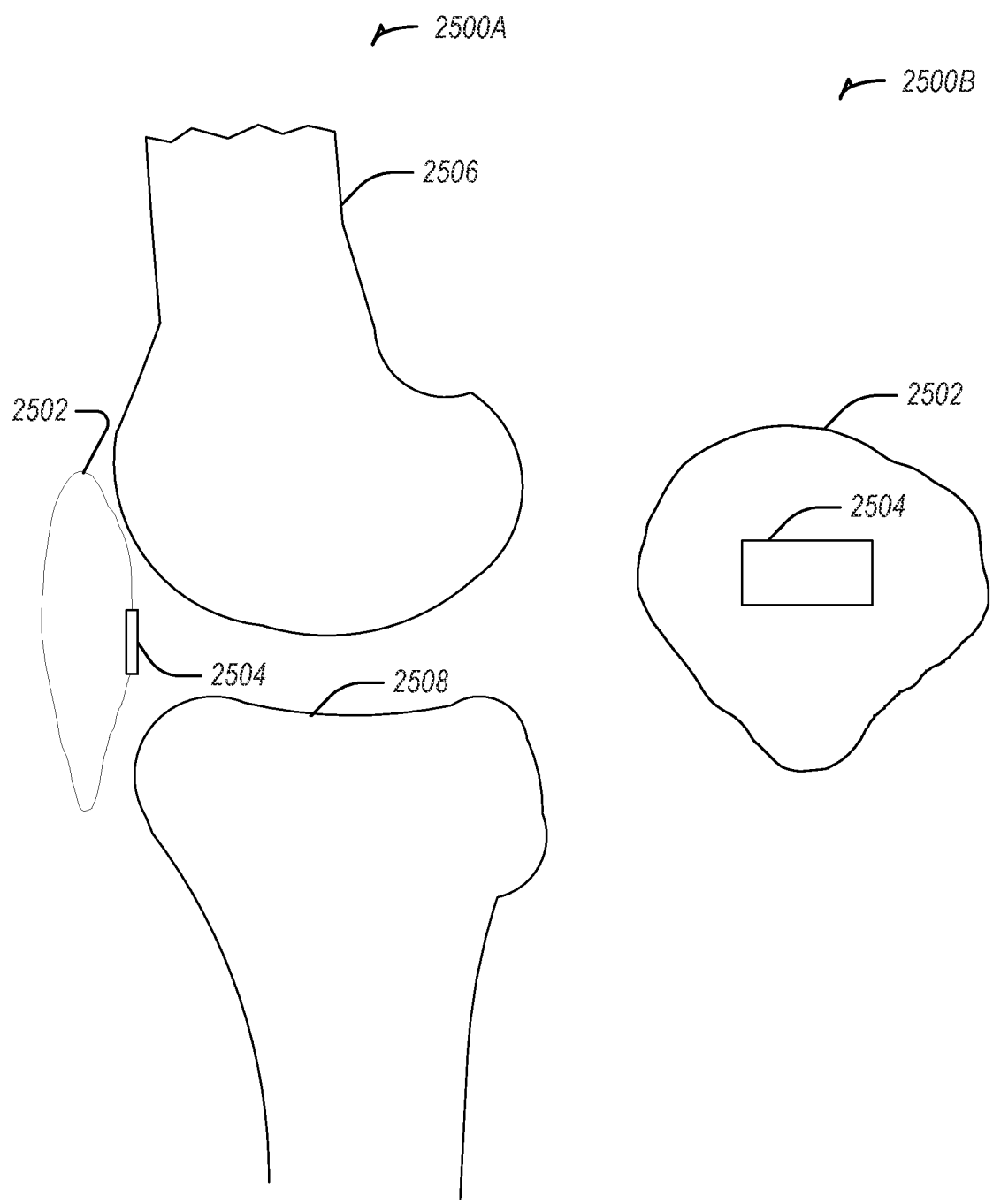
*FIG. 25A*  *FIG. 25B*

SOFT TISSUE BALANCING IN ARTICULAR SURGERY

CLAIM OF PRIORITY

This application is a continuation of U.S. patent application Ser. No. 16/166,795, filed Oct. 22, 2018, which is a continuation of U.S. patent application Ser. No. 15/624,621, filed Jun. 15, 2017, now issued as U.S. Pat. No. 10,136,952, which claims the benefit of priority to U.S. Provisional Applications Nos. 62/350,958, filed Jun. 16, 2016, titled "Method and System for Balancing Soft Tissue in Articular Surgery"; 62/375,049, filed Aug. 15, 2016, titled "Method and System for Balancing Soft Tissue in Articular Surgery"; 62/424,732 filed Nov. 21, 2016, titled "Soft Tissue Balancing in Articular Surgery"; and 62/501,585, filed May 4, 2017, titled "Soft Tissue Balancing in Articular Surgery", each of which is hereby incorporated herein by reference in its entirety.

TECHNICAL FIELD

The present application relates to computer-assisted orthopedic surgery used to assist in the placement of implants at articular surfaces of bones.

BACKGROUND

Computer-assisted surgery has been developed in order to help a surgeon in altering bones, and in positioning and orienting implants to a desired location. Computer-assisted surgery may encompass a wide range of devices, including surgical navigation, pre-operative planning, and various robotic devices. One area where computer-assisted surgery has potential is in orthopedic joint repair or replacement surgeries. For example, soft tissue balancing is an important factor in articular repair, as an unbalance may result in joint instability. However, when performing orthopedic surgery on joints, soft tissue evaluations are conventionally done by hand, with the surgeon qualitatively assessing the limits of patient's range of motion. The conventional technique may result in errors or lack precision.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 17A and 17B are user interfaces for displaying a range-of-motion (ROM) analysis of a CAS controller in accordance with some embodiments.

FIGS. 25A-25B illustrate a patella sensor in a range of motion testing system in accordance with some embodiments.

DETAILED DESCRIPTION

The systems and methods described herein may be used for soft tissue balancing using a robotic arm. A robotic arm, used during a surgical procedure may perform soft tissue balancing assessment. For example, a component (such as a pin, a cutting block, etc., as further described below) may anchor to a bone and the robotic arm may be driven to pull on the bone or other anatomy to perform the soft tissue balancing assessment. In an example, the soft tissue may be placed under tension to determine balance. Applied tension may be determined using information received from a force/torque sensor in the robotic arm. The robotic arm may include a sensor (e.g., inertial, optical, encoder, etc.) to measure a rotation indicative of a rotation required for soft tissue balancing. The soft tissue balancing may be performed with the robotic arm with a leg in flexion or in extension. In an example, a computer-assisted surgery (CAS) system may be used to implement or control the robotic arm.

In an example, a robotic arm may raise an end effector (e.g., located at a distal end of the robotic arm) to displace a femur, while the tibia remains still by gravity, by its fixation to the table (e.g., when a foot support is used), by a human (e.g., surgical assistant or the surgeon), by surgical tape, self-adherent wrap or tape, or other fixing devices or components to secure the tibia. In another example, the robotic arm may use a laminar spreader to spread the bones apart. The laminar spreader may be inserted in the gap between the femoral condyles and the tibial plateau. In order to assist the laminar spreader, additional devices may be used and manipulated by the robotic arm. For example, the robotic arm may manipulate a clamp to benefit from the leveraging of the clamp to apply a greater moment of force at the bones. The laminar spreader may include a gear mechanism (e.g., planetary gear device, rack and pinion, etc.) to assist in amplifying the force of the robotic arm.

A joint laxity may be determined using a sensor on the robotic arm or a component attached to the robotic arm, such as to assist in the soft-tissue balancing at different times during a surgical procedures. For example, soft-tissue balancing may be determined prior to having the robotic arm perform an alteration to the bone, to confirm a predetermined implant size or location on the bone, or to enable adjustments to the predetermined implant size or location on the bone. In another example, the soft-tissue balancing may be determined after one or more cut planes have been made, such as to determine whether further adjustments are necessary.

Figure 1:
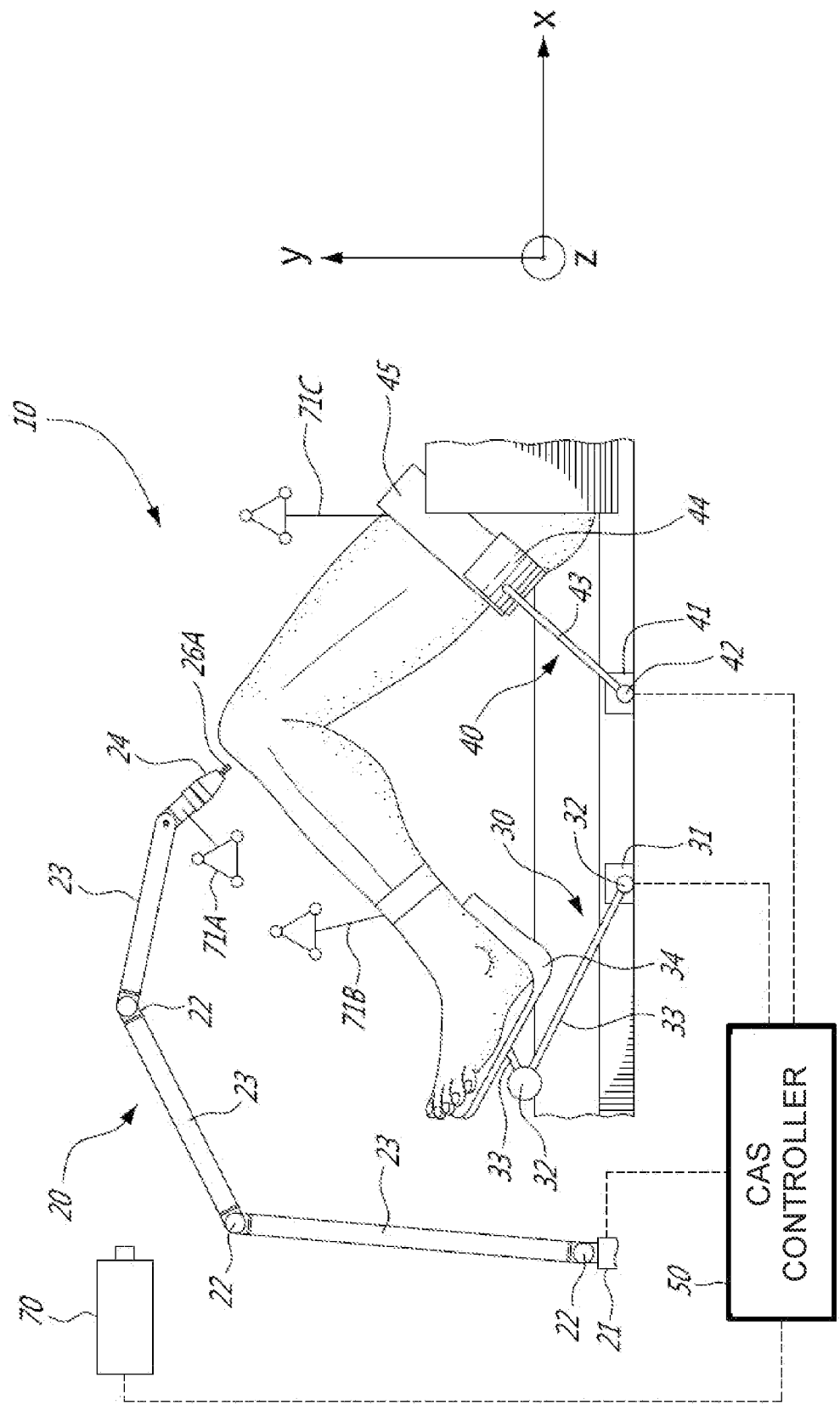
FIG. 1 is a schematic view of a CAS system in accordance with some embodiments.

Referring to the drawings and more particularly to FIG. 1, a computer-assisted surgery (CAS) system is generally shown at 10, and is used to perform orthopedic surgery maneuvers on a patient, including pre-operative analysis of range of motion and implant assessment planning, as described hereinafter. The system 10 is shown relative to a patient's knee joint in supine decubitus, but only as an example. The system 10 could be used for other body parts, including non-exhaustively hip joint, spine, and shoulder bones. A particular function of the CAS system 10 is assistance in planning soft tissue balancing, whereby the CAS system 10 may be used in total knee replacement surgery, to balance tension/stress in knee joint ligaments.

The CAS system 10 may be robotized, in which case it may have a robot arm 20, a foot support 30, a thigh support 40 and a CAS controller 50. The robot arm 20 is the working end of the system 10, and is used to perform bone alterations as planned by an operator or the CAS controller 50 and as controlled by the CAS controller 50. The foot support 30 supports the foot and lower leg of the patient, in such a way that it is only selectively movable. The foot support 30 may be robotized in that its movements may be controlled by the CAS controller 50. The thigh support 40 supports the thigh and upper leg of the patient, again in such a way that it is only selectively or optionally movable. The thigh support 40 may optionally be robotized in that its movements may be controlled by the CAS controller 50. The CAS controller 50 controls the robot arm 20, the foot support 30, or the thigh support 40. Moreover, as described hereinafter, the CAS controller 50 may perform a range-of-motion (ROM) analysis and implant assessment in pre-operative planning, with or without the assistance of an operator. The CAS controller 50 may also guide an operator through the surgical procedure, by providing intraoperative data of position and orientation and joint laxity boundaries, as explained hereinafter. The tracking apparatus 70 may be used to track the bones of the patient, and the robot arm 20 when present. For example, the tracking apparatus 70 may assist in performing the calibration of the patient bone with respect to the robot arm, for subsequent navigation in the X, Y, Z coordinate system.

Figure 2:
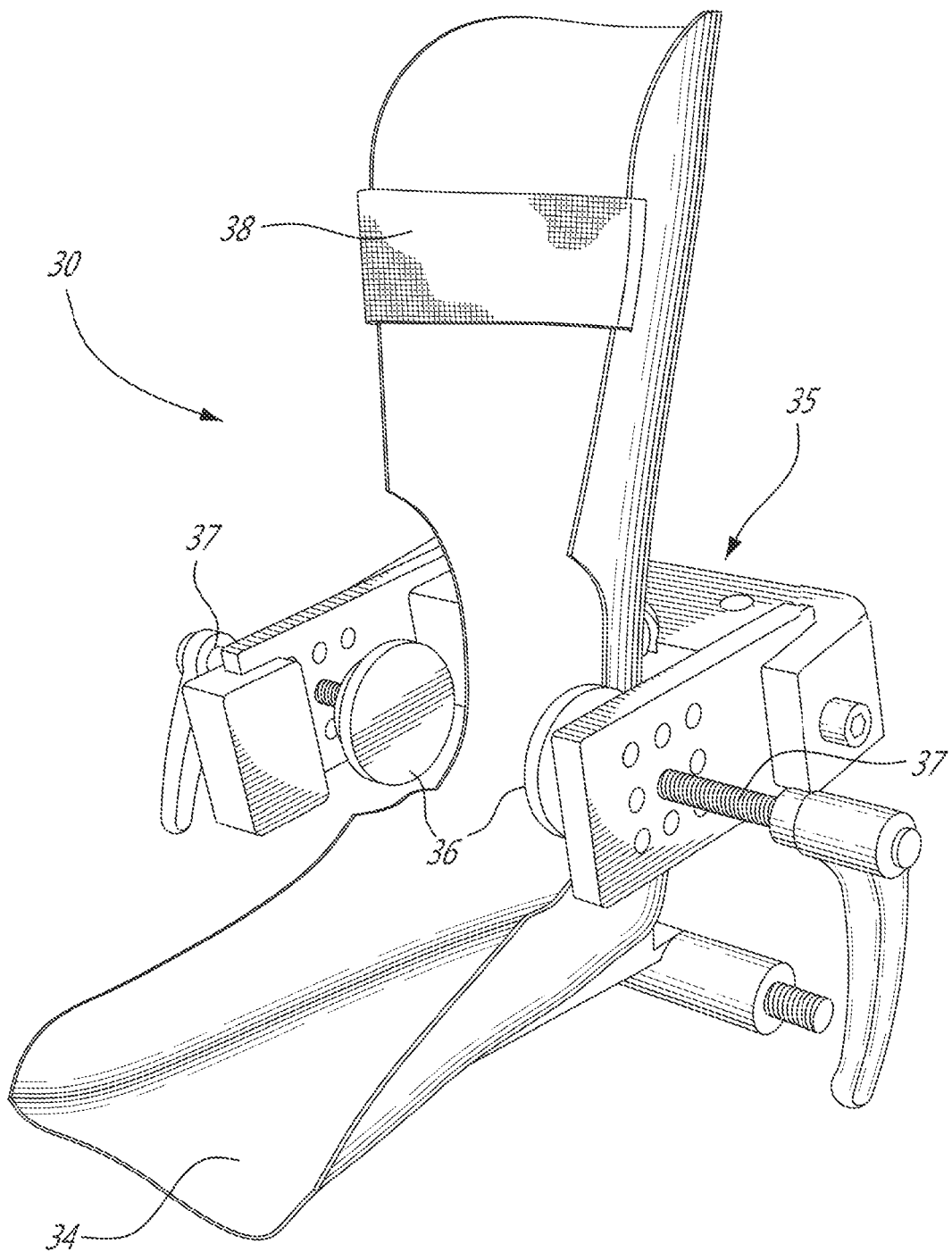
FIG. 2 is an exemplary perspective view of a foot support of a CAS system in accordance with some embodiments.

Referring to FIGS. 1 and 2, a schematic example of the robot arm 20 is provided. The robot arm 20 may stand from a base 21, for instance in a fixed relation relative to the operating-room (OR) table supporting the patient. In one example configuration, the OR table may consist of a 'U'-shaped end portion with each side of the 'U' supporting a leg of the patient and an open floor space existing between each leg. In this configuration, the base is positioned in the open floor space between the legs, therefore allowing the robot arm to access each leg of the patient without repositioning the base as would be desired in a bilateral total knee replacement procedure. The relative positioning of the robot arm 20 relative to the patient is a determinative factor in the precision of the surgical procedure, whereby the foot support 30 and thigh support 40 may assist in keeping the operated limb fixed in the illustrated X, Y, Z coordinate system. The robot arm 20 has a plurality of joints 22 and links 23, of any appropriate form, to support a tool head 24 that interfaces with the patient. The arm 20 is shown being a serial mechanism, arranged for the tool head 24 to be displaceable in a desired number of degrees of freedom (DOF). For example, the robot arm 20 controls 6-DOF movements of the tool head 24, i.e., X, Y, Z in the coordinate system, and pitch, roll and yaw. Fewer or additional DOFs may be present. For simplicity, only a generic illustration of the joints 22 and links 23 is provided, but more joints of different types may be present to move the tool head 24 in the manner described above. The joints 22 are powered for the robot arm 20 to move as controlled by the controller 50 in the six DOFs. Therefore, the powering of the joints 22 is such that the tool head 24 of the robot arm 20 may execute precise movements, such as moving along a single direction in one translation DOF, or being restricted to moving along a plane, among possibilities. Such robot arms 20 are known, for instance as described in U.S. patent application Ser. No. 11/610,728, incorporated herein by reference.

Figure 3:
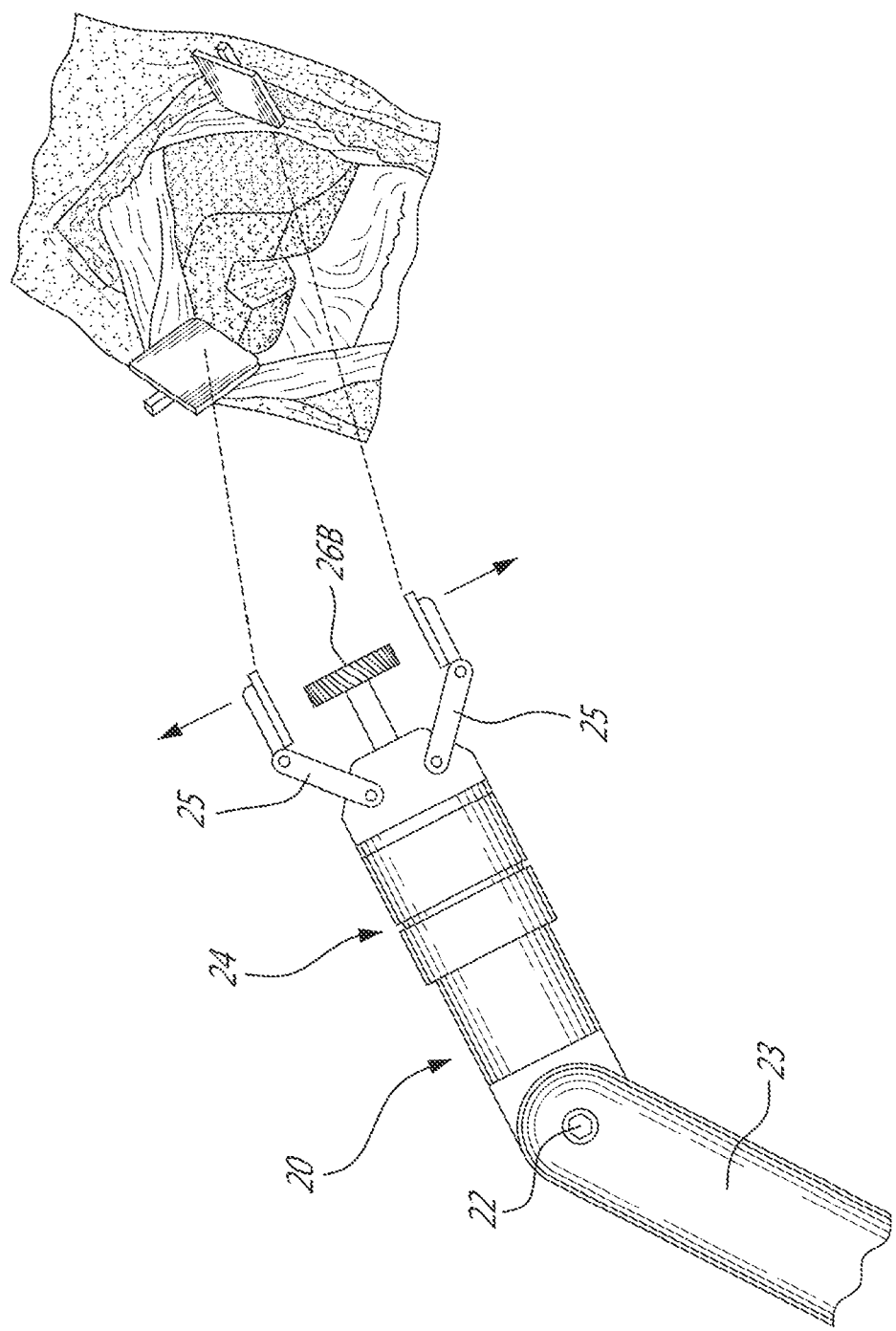
FIG. 3 is a perspective schematic view of a tool head of a CAS system in accordance with some embodiments.

Referring to FIG. 3, the tool head 24 is shown in greater detail. The tool head 24 may have laminar spreader plates 25, actuatable independently from a remainder of the tool head 24, for simultaneous use with a tool support by the tool head 24. The laminar spreader plates 25 are used to spread soft tissue apart to expose the operation site. The laminar spreader plates 25 may also be used as pincers, to grasp objects, etc. The tool head 24 may also comprise a chuck or like tool interface, typically actuatable in rotation. In FIG. 1, the tool head 24 supports a burr 26A, used to resurface a bone. In FIG. 3, the tool head 24 supports a circular tool 26B. As a non-exhaustive example, other tools that may be supported by the tool head 24 include a registration pointer, a reamer, a reciprocating saw, a retractor, depending on the nature of the surgery. The various tools may be part of a multi-mandible configuration or may be interchangeable, whether with human assistance, or as an automated process. The installation of a tool in the tool head 24 may then require some calibration in order to track the installed tool in the X, Y, Z coordinate system of the robot arm 20.

In order to preserve the fixed relation between the leg and the coordinate system, and to perform controlled movements of the leg as described hereinafter, a generic embodiment is shown in FIG. 1, while one possible implementation of the foot support 30 is shown in greater detail in FIG. 2. The foot support 30 may be displaceable relative to the OR table, in order to move the leg in flexion/extension (e.g., to a fully extended position and to a flexed knee position), with some controlled lateral movements being added to the flexion/extension. Accordingly, the foot support 30 is shown as having a robotized mechanism by which it is connected to the OR table, with sufficient DOFs to replicate the flexion/extension of the lower leg. Alternatively, the foot support 30 could be supported by a passive mechanism, with the robot arm 20 connecting to the foot support 30 to actuate its displacements in a controlled manner in the coordinate system. The mechanism of the foot support 30 may have a slider 31, moving along the OR table in the X-axis direction. Joints 32 and links 33 may also be part of the mechanism of the foot support 30, to support a foot interface 34 receiving the patient's foot.

Referring to FIG. 2, an example of the foot interface 34 has an L-shaped body ergonomically shaped to receive the patient's foot. In order to fix the foot in the foot support 33, different mechanisms may be used, one of which features an ankle clamp 35. The ankle clamp 35 surrounds the rear of the foot interface 34, and laterally supports a pair of malleolus pads 36. The malleolus pads 36 are positioned to be opposite the respective malleoli of the patient, and are displaceable via joints 37, to be brought together and hence clamp onto the malleoli. A strap 38 may also be present, to further secure the leg in the foot support 30, for example by attaching to the patient's shin. As an alternative to the arrangement of FIG. 2, a cast-like boot may be used, or a plurality of straps 38, provided the foot is fixed in the foot support 33. In essence, the foot support 30 must anchor the leg to the table, with controllable movements being permissible under the control of the controller 50.

Referring to FIG. 1, the thigh support 40 may be robotized, static or adjustable passively. In the latter case, the thigh support 40 may be displaceable relative to the OR table, in order to be better positioned as a function of the patient's location on the table. Accordingly, the thigh support 40 is shown as including a passive mechanism, with various lockable joints to lock the thigh support 40 in a desired position and orientation. The mechanism of the thigh support 40 may have a slider 41, moving along the OR table in the X-axis direction. Joints 42 and links 43 may also be part of the mechanism of the thigh support 40, to support a thigh bracket 44. A strap 45 may immobilize the thigh/femur in the thigh support 40. The thigh support 40 may not be necessary in some instances. However, in the embodiment in which the range of motion is analyzed, the fixation of the femur via the thigh support 40 may assist in isolating joint movements.

Figure 4:
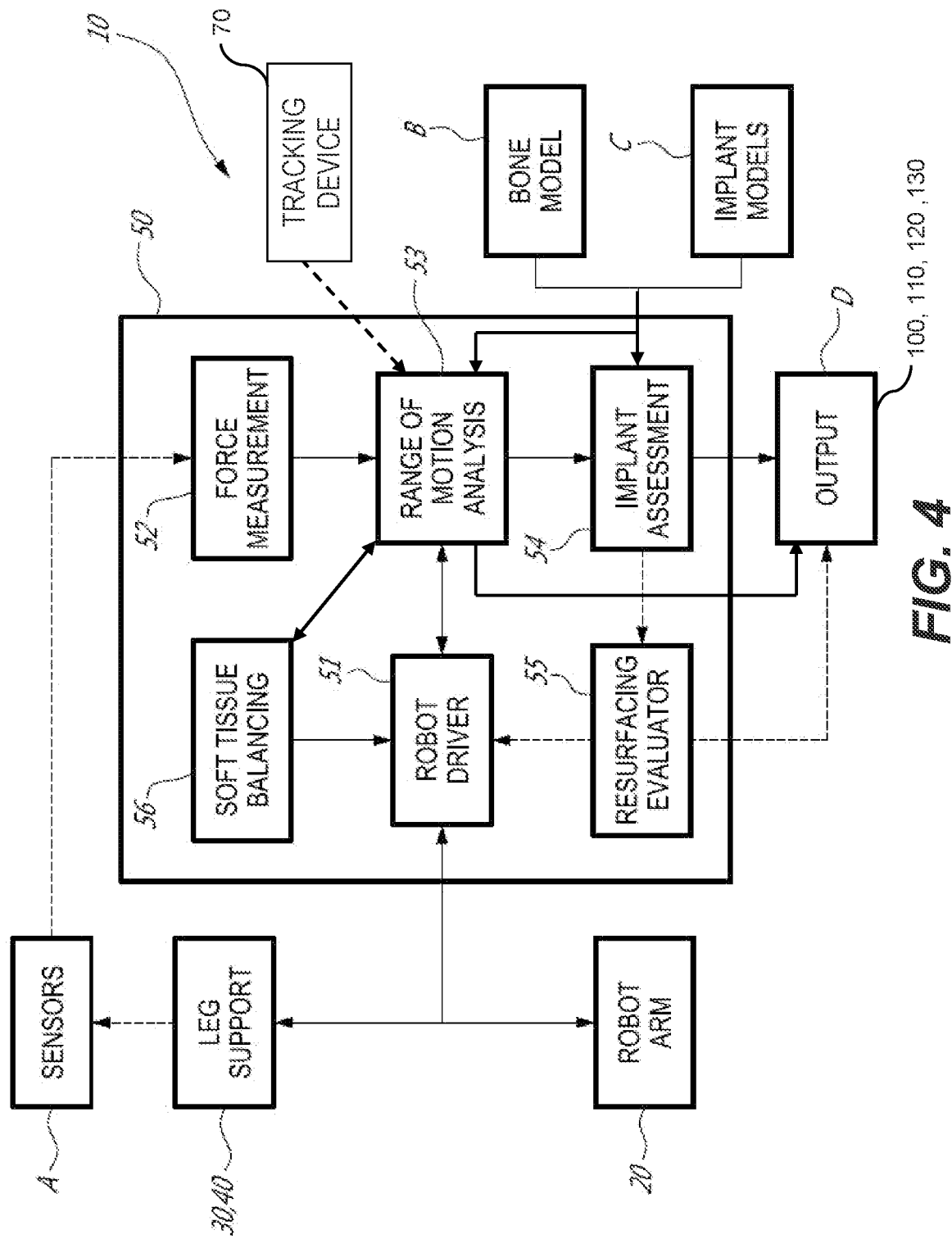
FIG. 4 is a block diagram of a CAS controller used with a robotized surgery system in accordance with some embodiments.

Referring to FIG. 4, the CAS controller 50 is shown in greater detail relative to the other components of the robotized surgery system 10. The controller 50 has a processor unit to control movement of the robot arm 20, and of the leg support (foot support 30 and thigh support 40), when applicable. The robotized surgery controller 50 provides computer-assisted surgery guidance to an operator, whether in the form of a range-of-motion (ROM) analysis or implant assessment in pre-operatively planning or during the surgical procedure. The system 10 may comprise various types of interfaces, for the information to be provided to the operator. The interfaces may be monitors or screens including wireless portable devices (e.g., phones, tablets), audio guidance, LED displays, among many other possibilities. For example, there is illustrated in FIGS. 20-23 and 33A-33D graphic user interfaces (GUI) e.g., 100, 110, 120, 130, and 3300A-3300D that may be operated by the system 10. The controller 50 may then drive the robot arm 20 in performing the surgical procedure based on the planning achieved pre-operatively. The controller 50 may do an intra-operative soft-tissue balancing assessment, and hence enable corrective plan cuts to be made, or guide the selection of implants or other intra-operative adjustments to the plan. The controller 50 may also perform a post-operative ROM analysis.

The controller 50 may hence have a robot driver 51, such as when the robot arm 20 is part of the CAS system 10. The robot driver 51 is tasked with powering or controlling the various joints of the robot arm 20, foot support 30 and thigh support 40, when applicable. As shown with bi-directional arrows in FIG. 4, there may be some force feedback provided by the robot arm 20 and leg support 30,40 to avoid overextending the leg or damaging the soft tissue, and to assist in determining joint laxity boundaries. The robot driver 51 may control the foot support 30 in performing particular motions, to replicate a flexion/extension of the knee, with lateral movements, to measure soft tissue tension and analyze the range of motion of the leg, including varus/valgus. As such, the robot driver 51 may output the instant angle of flexion using the position or orientation data it uses to drive the movement of the foot support 30. Sensors A are provided on the foot support 30 or in the robot arm 20 in order to measure throughout the movement the forces indicative of the tension/stress in the joint. The sensors A must therefore be sensitive enough to detect soft tissue tension/stress through the movement of the foot support 30. In the case of the robot arm 20, the sensors A may be force-torque sensors integrated therein.

The CAS controller 50 may use a processor to implement force measurement 52. Force measurement 52 may include receiving the signals from the sensors A, and calculating the instant forces on the foot support 30, representative of the tension/stress in the knee joint, or in the robot arm 20, as exemplified hereinafter. The instant forces may be used to perform ROM analysis 53 using the processor, along with the foot support tracking data from the robot driver 51. Alternatively or additionally, the ROM analysis 53 may use tracking data received from the tracking device 70 to determine the range of motion of the leg, as explained hereinafter. The ROM analysis 53 may convert the signals from the tracking device 70 into position or orientation data. In the latter case, various types of tracking technology may be used to determine the instant flexion/extension and varus/valgus, such as optical tracking as illustrated in FIG. 1, inertial sensors, etc. With the combined data from the force measurement 52 and from the robot driver 51 or other source such as surgeon or medical professional assessment, the ROM analysis 53 may be performed. Exemplary formats of the ROM analysis 53 are shown in FIG. 17B and in FIGS. 22A-22F, described hereinafter. The information of the ROM analysis 53 may therefore be a pre-operative indication of the current varus/valgus as a function of flexion/extension. The ROM analysis 53 may be performed intra-operatively, or post-operatively, to assist in quantifying the soft tissue balancing during or resulting from surgery.

The processor may be used to perform an implant assessment 54 to determine how an implant or implants will impact the range of motion. Using the ROM analysis 53, the implant assessment 54 takes into consideration the geometrical configuration of the implants based on selectable locations on the bone. For example, the implant assessment 54 may include the bone models B from pre-operative imaging (e.g., MRI, CT-scans), whether in 3D or in multiple 2D views. The implant assessment 54 may include the implant models C, such the 3D model files including implants of different dimensions.

Figure 18B:
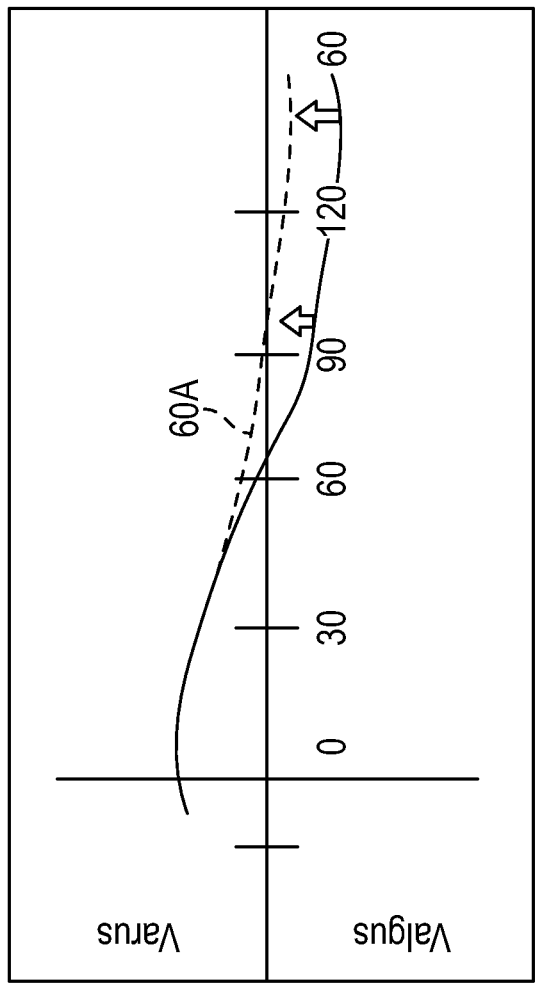
FIGS. 18A and 18B are user interfaces for displaying an implant assessment of a CAS controller, enabling implant movement from a caudal viewpoint in accordance with some embodiments.
Figure 19A:
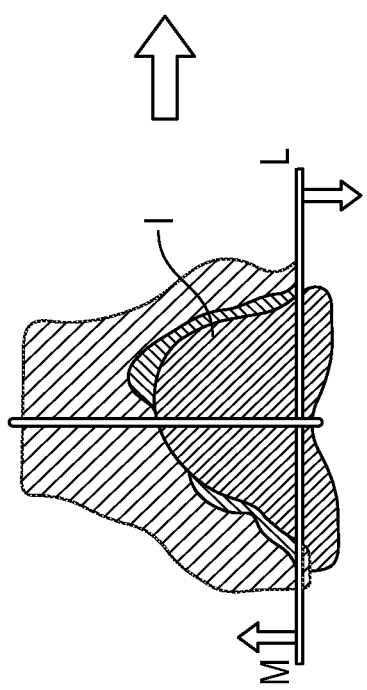
FIGS. 19A and 19B are user interfaces for displaying an implant assessment of a robotized surgery controller, enabling implant movement from a frontal viewpoint in accordance with some embodiments.
Figure 19B:
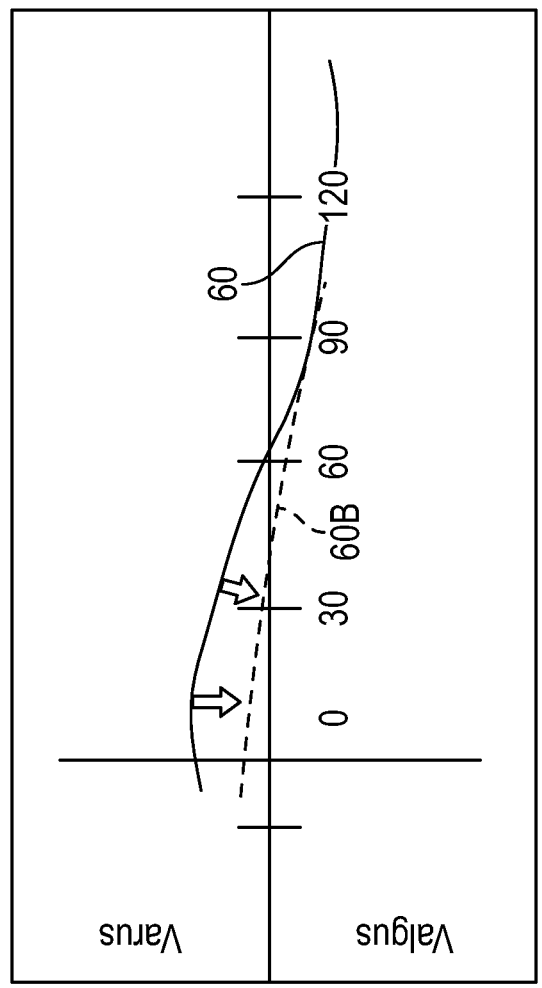

The implant assessment 54 may be performed in a fully automated manner by the processor, in evaluating from the bone model, implant models or from the ROM analysis 53 desired implant sizes and location on the bone (i.e., in position and orientation), to balance soft tissue tension/stress. Exemplary formats of the implant assessment are shown in FIGS. 18B, 19B and 23, described hereinafter. The information of the implant assessment may therefore be a pre-operative or intraoperative indication of an anticipated post-surgical varus/valgus as a function of flexion/extension.

The implant assessment 54 may optionally include operator participation. The illustrations of FIGS. 18A and 19A may be GUI items, such as in GUI 130 of FIGS. 23A and 23B that may be adjusted virtually manually by an operator, for the operator to see the impact on the graphs of FIGS. 18B and 18B, respectively. In such an embodiment, the implant assessment 54 may provide the assessment to assist the operator in making a decision, as opposed to automatically proposing the desired implant sizes and location on the bone. The proposal of desired implant sizes and location on the bone may be a starting point of operator navigation or decision making. When the implant sizes and location on the bone is selected or set, the implant assessment 54 may produce the output D in any appropriate format, such as GUIs 130. The format may also be that of FIGS. 18B and 18B, providing an assessment of the proposed implant sizes and location. The output D may also include bone alteration data to assist the operator or the robot arm 20 in performing the bone alterations. In such a case, the processor may perform a resurfacing evaluation 55 to calculate the bone cut volume and location, for the bone cuts that will be made based on the implant sizes and location on the bone.

The output D may also be a navigation file for the robot arm 20 to perform bone alterations based on the pre-operative planning from the implant assessment 54, when the system 10 is robotized. The navigation file may include patient-specific numerical control data defining the maneuvers to be performed by the robot arm 20 as directed by the robot driver 51 of the system 10, or of another system 10 in an operating room. The navigation file for robotized surgery may incorporate a calibration subfile to calibrate the robot arm 20 and patient joint prior to commencing surgery. For example, the calibration subfile may include the bone model B of the patient, for surface matching to be performed by a registration pointer of the robot arm 20. The robot arm 30 may obtain a cloud of bone landmarks of the exposed bones, to reproduce a 3D surface of the bone. The 3D surface may then be matched to the bone model B of the patient, to set the 3D model in the X, Y, Z coordinate system.

The use of the tracking apparatus 70 may be determinative on the information that will be in the navigation file C, and may provide tracking data to perform the ROM analysis 53. For example, the tracking apparatus 70 may assist in performing the calibration of the patient bone with respect to the robot arm 20, for subsequent navigation in the X, Y, Z coordinate system. According to an embodiment, the tracking apparatus 70 comprises a camera that optically sees and recognizes retro-reflective references 71A, 71B, and 71B, so as to track the limbs in six DOFs, namely in position and orientation. In an embodiment featuring the robot arm 20, the reference 71A is on the tool head 24 of the robot arm 20 such that its tracking allows the controller 50 to calculate the position or orientation of the tool head 24 and tool 26A thereon. Likewise, references 71B and 71C are fixed to the patient bones, such as the tibia for reference 71B and the femur for reference 71C. As shown, the references 71 attached to the patient need not be invasively anchored to the bone, as straps or like attachment means may provide sufficient grasping to prevent movement between the references 71 and the bones, in spite of being attached to soft tissue. However, the references 71B and 71C could also be secured directly to the bones. Therefore, the ROM analysis 53 of the controller 50 may be continuously updated to obtain a current position or orientation of the robot arm 20 or patient bones in the X, Y, Z coordinate system using the data from the tracking apparatus 70. As an alternative to optical tracking, the tracking system 70 may consist of inertial sensors (e.g., accelerometers, gyroscopes, etc) that produce tracking data to be used by the controller 50 to continuously update the position or orientation of the robot arm 20. Other types of tracking technology may also be used.

The calibration may be achieved in the manner described above, with the robot arm 20 using a registration pointer on the robot arm 20, and with the assistance of the tracking apparatus 70 when present in the robotized surgery system 10. Another calibration approach is to perform radiography of the bones with the references 71 thereon, at the start of the surgical procedure. For example, a C-arm may be used for providing suitable radiographic images. The images are then used for the surface matching with the bone model B of the patient. Because of the presence of the references 71 as fixed to the bones, the intraoperative registration may then not be necessary, as the tracking apparatus 70 tracks the position or orientation of the bones in the X, Y, Z coordinate system after the surface matching between X-ray and bone model is completed.

Figure 5A:
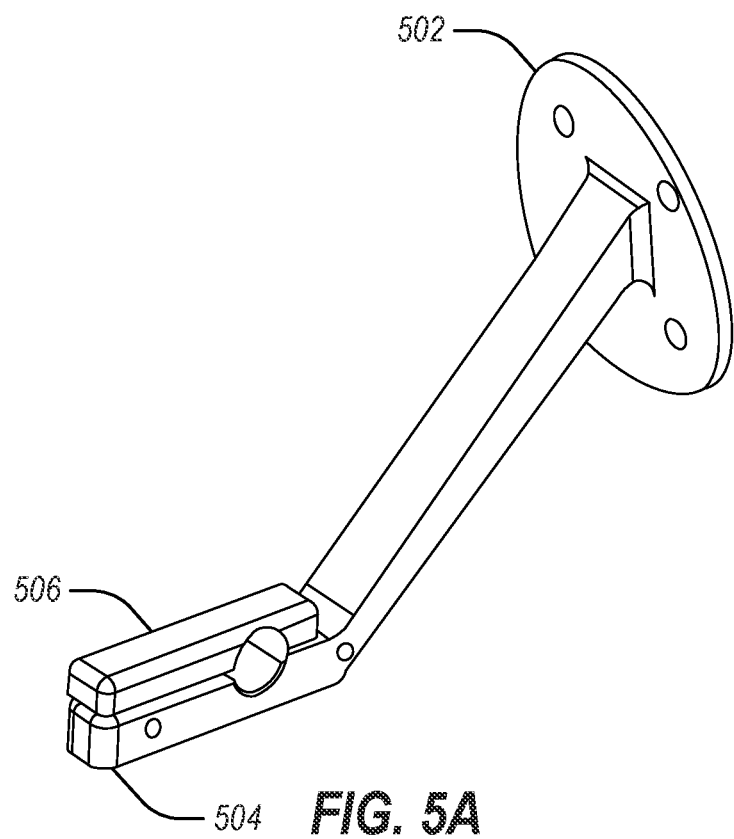
FIGS. 5A-5B illustrate a robotic arm with a pin guide end effector component in accordance with some embodiments.
Figure 5B:
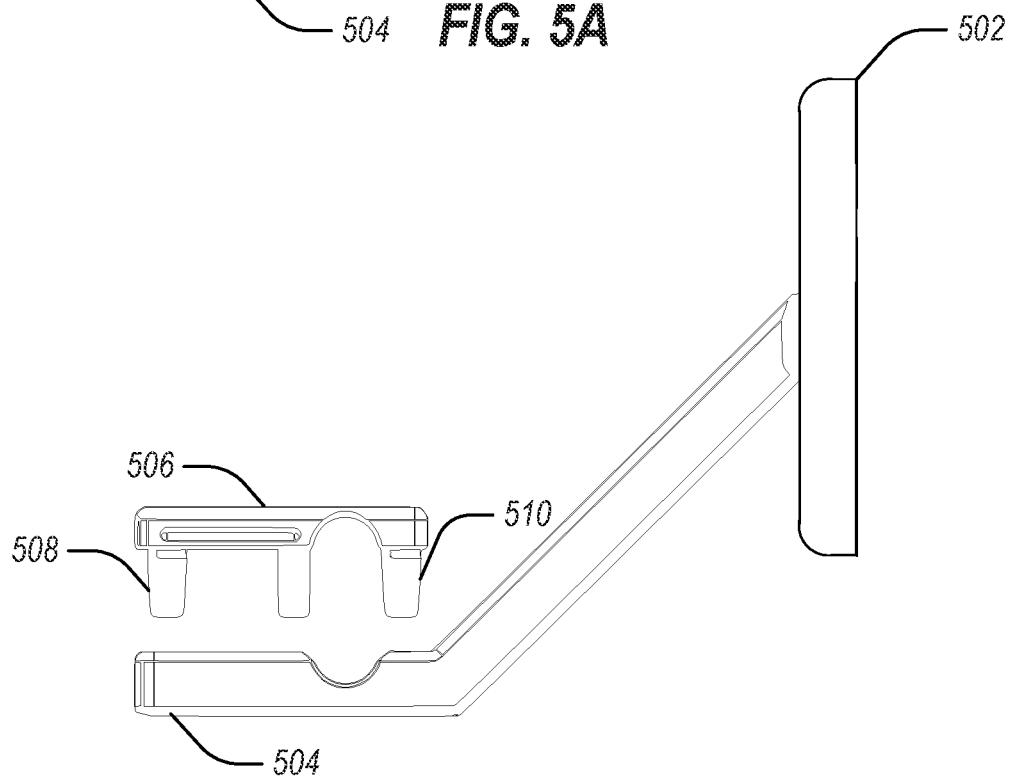

FIGS. 5A-5B illustrate a robotic arm 502 with a detachable pin guide component 506 coupled to an end effector component 504 in accordance with some embodiments. The detachable pin guide component 506 may include one or more pins (e.g., pins 508 and 510), which may fit in one or more apertures of the end effector component 504. The detachable pin guide component 506 may couple with the end effector component 504 in a locked position (e.g., as shown in FIG. 5A) and may be removed (e.g., as shown in FIG. 5B). The detachable pin guide component 506 may be locked to the end effector component 504 using, for example, a screw, friction, etc. In an example, the detachable pin guide component 506 may be disposable.

In an example, the detachable pin guide component 506 may include a cut guide (e.g., an slot for inserting a saw or other surgical instrument). For example, the detachable pin guide component 506 may include a femoral cut guide, a tibial cut guide, a 4-in-1 cut guide, or the like. In an example, the detachable pin guide component 506 may be configured for use with a specific implant or may be used generically.

In an example, a bushing may be used, such as between the detachable pin guide component 506 and the end effector component 504. The bushing may be used to prevent jamming between the end effector component 504 and the detachable pin guide component 506 or allow for easy removal of the detachable pin guide component 506. The bushing may be removable, and may be affixed to the end effector component 504. In another example, the end effector component may include one or more pins and the detachable pin guide component 506 may include one or more apertures; these features may be in addition to or may replace the one or more pins of the detachable pin guide component 506 (e.g., pins 508 or 510) or the apertures of the end effector component 504.

The detachable pin guide component 506 may include a groove corresponding to a groove on the end effector component 504. When the detachable pin guide component 506 and the end effector component 504 are coupled, the grooves may provide an aperture for receiving a soft tissue balancing component. The robotic arm 502 may apply force to the soft tissue balancing component using the end effector component 504 or the detachable pin guide component 506 locked to the end effector component 504. The soft tissue balancing component (e.g., as described in further detail below, for example in the discussion of FIGS. 6A-6B, 7A-7B, and 10A-10D) may apply force in turn to a bone or implant component to test or configure soft tissue balance.

The soft tissue balancing component may be used to perform a ligament balance pull test. Based on the pull test, a femoral rotation may be determined. The femoral rotation may be presented (e.g., using a graphical user interface, such as those described below in the discussion of FIGS. 22A-22F and 33A-33D). In an example, the femoral implant rotation may be used to calculate a target femoral implant rotation. The target femoral implant rotation may be displayed (e.g., using a user interface, such as those described below in the discussion of FIGS. 33A-33D). The target femoral implant rotation may be an inverse or opposite of the rotation of the femur rotation. For example, when the femur rotation is 3 degrees internally, the target femoral implant rotation may be 3 degrees external from the femur. The target femoral implant rotation may be further adjusted as well.

The femoral implant rotation may be determined such that the rotation may compensate for an imbalance in soft tissue tension between medial and lateral compartments. The rotation of the femur during the pull test may be directly related to the determined femoral implant rotation such that a rectangular or balanced gap results from applying the rotation. For example, when the rotation is applied to placement of the implant, the gap may be balanced between the medial and the lateral compartments. In an example, the robotic arm 502 may apply a force to perform the pull test by using the soft tissue balancing component to pull on the femur. To perform the test, the robotic arm 502 may apply one or more known loads to increase the accuracy of the determined rotation.

In an example, a torque or force sensor may be used to measure torque of one or more of the components depicted in FIGS. 5A-5B, such as the robotic arm 502, the end effector component 504, or the detachable pin guide component 506, or on a component such as a soft tissue balancing component. In an example, a sensor may be used to detect ligament stress or ligament tension. In another example, a position or orientation sensor (e.g., a navigation sensor, such as a sensor located on a portion of the robotic arm 502) may be used to determine a varus or valgus angle of a target leg. The varus or valgus angle may be used to determine ligament pulling in the target leg. From the varus or valgus angle or the stress or tension on the ligament, pulling on the soft tissue may be determined and a rotation to correct the pulling may be determined, and may be output on a graphical user interface (GUI), such as that described with respect to FIGS. 33A-33D.

In an example, a ligament test or other soft tissue balancing test may be performed before a bone resection cut is performed. For example, the soft tissue balancing test may be performed before any resection of a femur or a tibia. In an example, the soft tissue balancing test may be performed after resection and implantation of an implant to verify that the soft tissue is correctly balanced. For example, a first test may be performed pre-resection, which may result in a rotation angle to be used for balancing, and a second test may be performed after the implant is inserted to verify that the rotation angle was correct or that the implant was properly seated.

In an example, resecting a bone may include using the robotic arm 502. The robotic arm 502 may have a cut guide attached to the end effector component 504 to guide the resection. A guide may be used to align a cutting, burring, or sawing device with a target object, such as a target bone. Cut guides are often manually placed by a surgeon on the target object. In other examples, cuts are made using fully autonomous robotic cutting devices. In another example, a surgeon may guide the robotic arm 502 collaboratively with force assistance from the robotic arm 502 (e.g., using a force sensor coupled to the robotic arm 502). In this example, the surgeon may apply a small directional force while the robotic arm 502 moves in response. The robotic arm 502 may then automatically align to a cut plane in response to a surgeon selection (e.g., on the robotic arm 502 or on a user interface). In an example, the cut guide may be used to precisely align a surgical instrument to make a cut, such as on a target bone or other target object. The alignment of the end effector component 504 may involve a planning system with a user interface including positioning a representation of the end effector component 504 on a representation of the target object. During the surgical procedure, a selectable indication on an intraoperative user interface (e.g., those of FIGS. 33A-33D) may be used to activate movement the end effector component 504 to the planned alignment position. The cut guide may be used as a guide for the surgical instrument to make a cut on the target object, such as to align the surgical instrument with a specific plane or line. By using a cut guide, a surgeon may retain control of the surgical instrument while also using the robotic arm 502 to ensure that the surgical instrument is aligned with a predetermined cut plane or cut line. The robot in conjunction with a surgical navigation system allows for repeatable transfer of predefined surgical plan to the patient during the surgical procedure, while still allowing the surgeon some level of control over the final cuts.

Figure 6A:
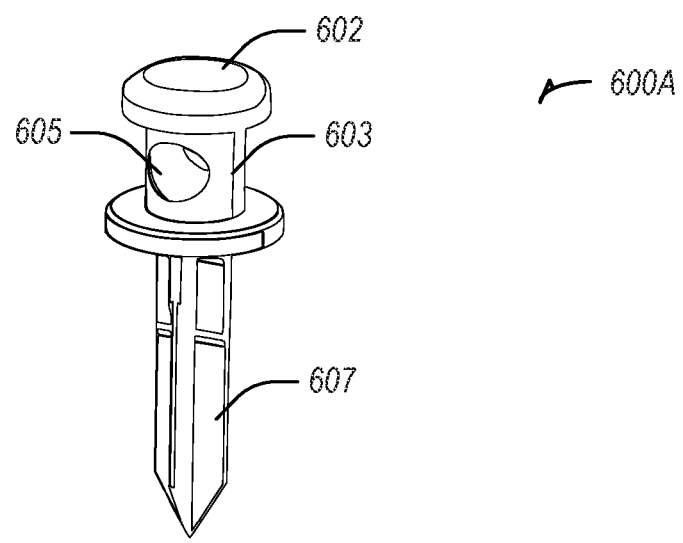
FIG. 6A illustrates a spike for use in a robotic soft tissue balancing system in accordance with some embodiments.

FIG. 6A illustrates a soft tissue balancing component, including a spike 602 for use in a robotic soft tissue balancing system 600A in accordance with some embodiments. The spike 602 may be used as a femoral spike to apply force to a femur. The spike 602 may include a shaft portion 603 to receive force and transfer the force via rigidity of the spike 602 to a spike portion 607, which in turn may apply force on the femur. The spike 602 may include a hollow shaft defined by an outer shaft wall 605. The hollow shaft may be perpendicular to the shaft portion 603. The hollow shaft may be used to lock or secure the spike in place (e.g., to prevent rotation), such as relative to a robotic arm or component.

In an example, the spike portion 607 of the spike 602 may include an enlarged surface area to minimize bone damage. In an example, different shaped spikes may be used (e.g., flat, rectangular, triangular, round, etc.), such as to accommodate the patella or soft tissue. In an example, the shaft portion 603 of the spike 602 and a component used to secure or couple with the spike 602 (e.g., a robotic arm or components attached thereto) may have a combined thickness, average thickness, or maximum thickness similar to (e.g., within a tolerance of) or less than a femoral implant to be used. For example, the shaft portion 603 of the spike 602 and the component used to secure or couple with the spike 602 may have a size such that a patellar tendon is under natural tension when the spike 602 is used to apply force to the femur.

Figure 6B:
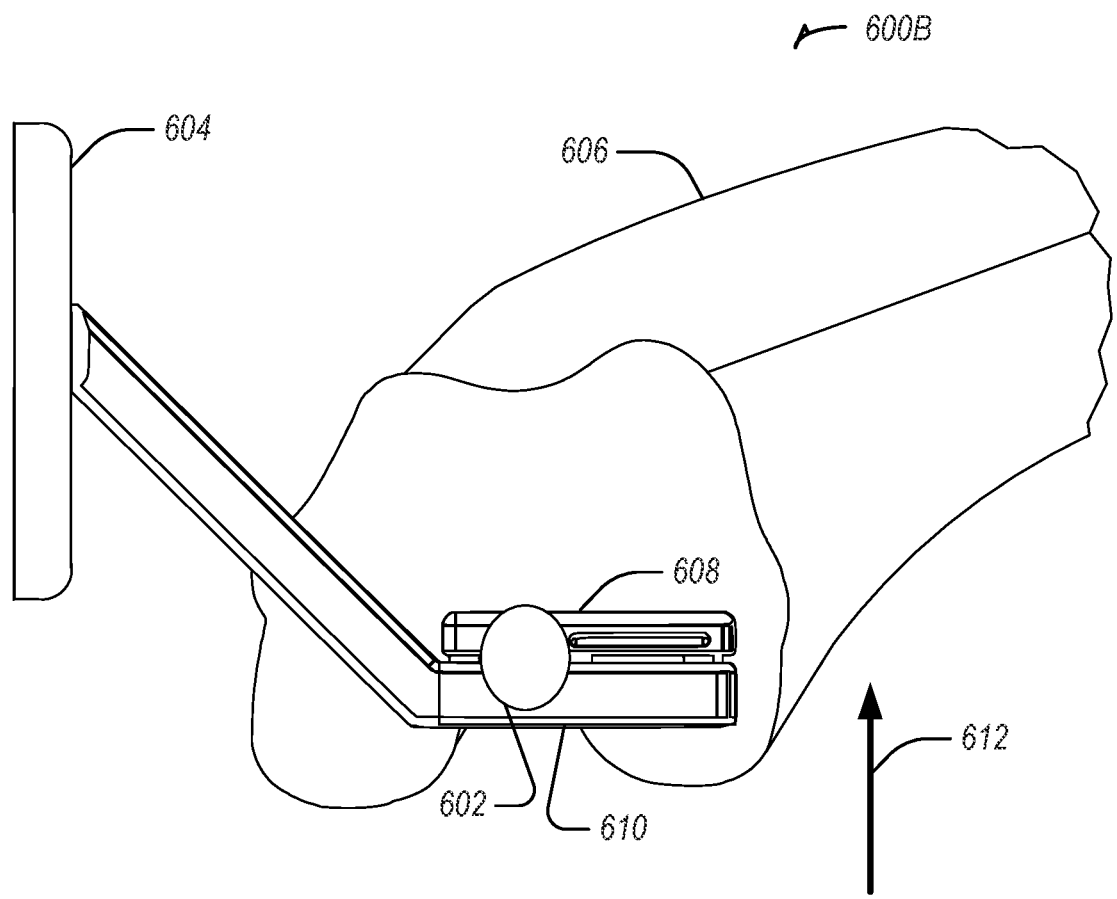
FIG. 6B illustrates a robotic soft tissue balancing system including a spike in accordance with some embodiments.

FIG. 6B illustrates a robotic soft tissue balancing system 600B including the spike 602 in accordance with some embodiments. The soft tissue balancing system 600B includes a robotic arm 604 to apply a force to the spike 602. The spike 602 may apply the force to a femur 606. The robotic arm 604 may include an end effector component 610 and a pin guide component 608, which may be detachable. The robotic arm 604, end effector component 610, and pin guide component 608 may be those described above with respect to FIGS. 5A-5B. In an example, the pin guide component 608 attaches to the end effector component 610 to secure the spike 602 in place relative to the robotic arm 604. The pin guide component 608 may be decoupled from the end effector component 610 to allow for removal of the spike 602.

A force applied by the robotic arm 604 on the spike 602 may cause the femur 606 to move, putting ligaments in tension. As the ligaments are pulled by the force on the femur 606, a balancing test may be performed. For example, tension in the ligaments may be measured or observed, force on the femur 606 may be tracked, or a rotation angle may be determined or observed. The rotation angle may then be used to set a target femoral rotation.

In an example, arrow 612 may represent a pull direction (e.g., force direction) that the spike 602 pulls the femur 606. For example, the arrow 612 may point along a line parallel to a plane of a resection cut of the femur 606. In an example, the arrow 612 may point along a line perpendicular to a plane formed by a top surface of the pin guide component 608 or perpendicular to an axis of the spike 602.

Figure 7A:
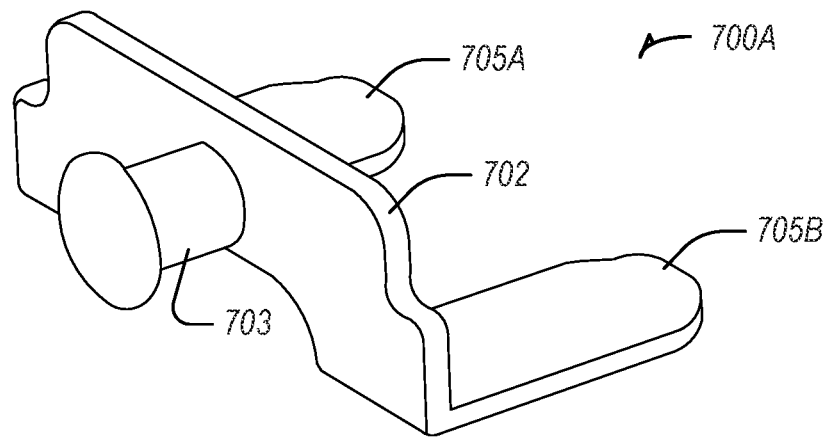
FIG. 7A illustrates a condyle pivot for use in a robotic soft tissue balancing system in accordance with some embodiments.

FIG. 7A illustrates a soft tissue balancing component, including a condyle pivot 702 for use in a robotic soft tissue balancing system 700A in accordance with some embodiments. The condyle pivot 702 may be used to apply force to a femur. The condyle pivot 702 may include a shaft portion 703 to receive force and transfer the force via rigidity of the condyle pivot 702 to platform arms 705A-705B, which in turn may apply force on the femur. The condyle pivot 702 may include a hollow shaft, which may be perpendicular to the shaft portion 703. The hollow shaft may be used to lock or secure the condyle pivot in place (e.g., to prevent rotation), such as relative to a robotic arm or component.

In an example, the platform arms 705A-705B of the condyle pivot 702 may include enlarged surface areas to minimize bone damage. In an example, different shaped platform arms 705A-705B may be used (e.g., flat, rectangular, triangular, round, etc.). In an example, the shaft portion 703 of the condyle pivot 702 and a component used to secure or couple with the condyle pivot 702 (e.g., a robotic arm or components attached thereto) may have a combined thickness, average thickness, or maximum thickness similar to (e.g., within a tolerance of) or less than a femoral implant to be used. For example, the shaft portion 703 of the condyle pivot 702 and the component used to secure or couple with the condyle pivot 702 may have a size such that a patellar tendon is under natural tension when the condyle pivot 702 is used to apply force to the femur.

The platform arms 705A-705B may each apply a same force or may apply different forces. For example, a torque may be applied to the condyle pivot 702 by the robotic arm 704 to keep the platform arms 705A-705B aligned along a plane, which may include varying force between the platform arms 705A-705B. When a limit is reached, for example, a first ligament is put in tension at a threshold level or a threshold force is reached, the relative forces applied on the platform arms 705A-705B may be used to determine a rotation angle to be used when resecting the femur 706 or when creating or inserting an implant. In another example, the platform arms 705A-705B may have equal force applied to each, and be allowed to rotate (e.g., away from an initial plane). The angle of the platform arms 705A-705B (e.g., relative to the initial plane) at an end position may be used to determine the rotation angle for later use. The end position may be determined when a threshold tension is reached on ligaments (e.g., a medial and a lateral ligament), when a threshold force is reached, or when a predetermined distance is reached (e.g., 5 mm, 10 mm, a distance corresponding to a tibia implant thickness such as 10 mm, 11 mm, 12 mm, etc.), which may include a safety factor (e.g., +/−1-5 mm), or the like. In an example, a combination of end position markers may be used, such as a predetermined distance approximately equal to a tibia implant thickness (e.g., an insert (poly) or an implant assembly, which may be predetermined using planning techniques), while retaining a maximum force as safety factor. For example, when a maximum force is reached before the predetermined distance, the robotic arm may be stopped. In another example, balanced ligaments may be used to mark the end position. The threshold tension may be determined visually or using a sensor. The end position (e.g., when rotation stops) may be determined by optical navigation in an example.

Figure 7B:
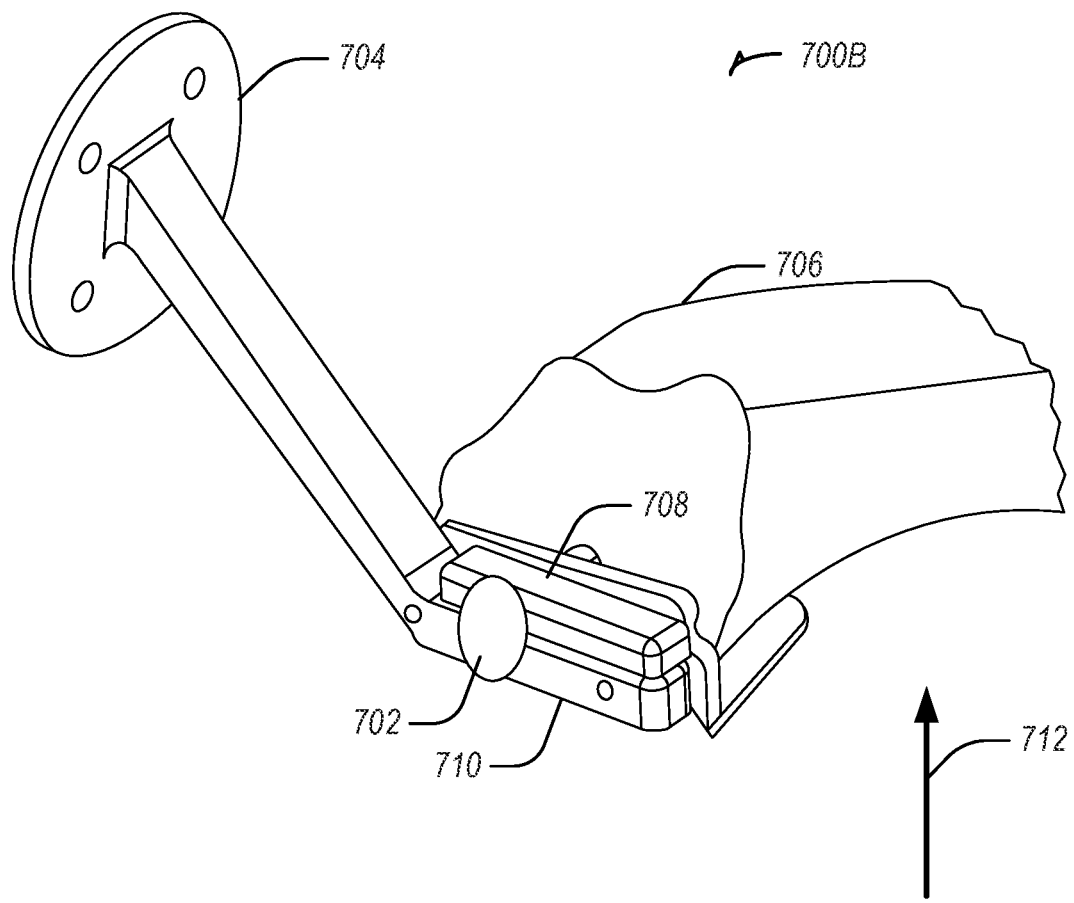
FIG. 7B illustrates a robotic soft tissue balancing system including a condyle pivot in accordance with some embodiments.

FIG. 7B illustrates a robotic soft tissue balancing system 700B including the condyle pivot 702 in accordance with some embodiments. The soft tissue balancing system 700B includes a robotic arm 704 to apply a force to the condyle pivot 702. The condyle pivot 702 may apply the force to a femur 706, such as by pushing the femur 706 in a direction away from a tibia. For example, the condyle pivot 702 may use the platform arms 705A-705B to push on the femur 706 to apply the force. The robotic arm 704 may include an end effector component 710 and a pin guide component 708, which may be detachable. The robotic arm 704, end effector component 710, and pin guide component 708 may be those described above with respect to FIGS. 5A-5B. In an example, the pin guide component 708 attaches to the end effector component 710 to secure the condyle pivot 702 in place relative to the robotic arm 704. The pin guide component 708 may be decoupled from the end effector component 710 to allow for removal of the condyle pivot 702.

A force applied by the robotic arm 704 on the condyle pivot 702 may cause the femur 706 to move, putting ligaments in tension. As the ligaments are pulled by the force on the femur 706, a balancing test may be performed. For example, tension in the ligaments may be measured or observed, force on the femur 706 may be tracked, or a rotation angle may be determined or observed.

In an example, a pivot point of the platform arms 705A-705B may be at the shaft portion 703 of the condyle pivot 702. The shaft portion 703 may be aligned, using the robotic arm 704, at various points of the femur 706. For example, the pivot point may be located at a medial condyle in a varus knee. In another example, pivot point may be the center of the knee. In yet another example, instead of using a spike as in FIGS. 6A-6B or a condyle pivot as in FIGS. 7A-7B, a posterior paddle, c-shaped adaptor, or other shape may be used to apply force to the femur 706.

In an example, a device may be inserted into a joint, such that turning a screw of the device may allow the soft tissue balancing test to be performed. For example, the device may expand at the turn of the screw. In an example, the robotic arm 704 may turn the screw. In an example, a force sensor for detecting force on the tibia, on the femur, or between the tibia and the femur may be the eLIBRA soft tissue force sensor device from Zimmer Biomet of Warsaw, IN.

The example device illustrated in FIGS. 7A and 7B is shown contacting a certain portion of a distal end of a partially resected femur. This is an exemplary engagement with the distal end of the femur, other examples may engage the femur in a different orientation or before or after resections. Additionally, in some examples, the platform arms 705A-705B may be contoured to facilitate engagement with the target bone surface.

In an example, arrow 712 may represent a pull direction (e.g., force direction) that the condyle pivot 702 pulls the femur 706. For example, the arrow 712 may point along a line parallel to a plane of a resection cut of the femur 706. In an example, the arrow 712 may point along a line perpendicular to a plane formed by a surface of the pin guide component 708 or a surface of the condyle pivot 702, for example a surface in contact with the femur 706.

Figure 8:
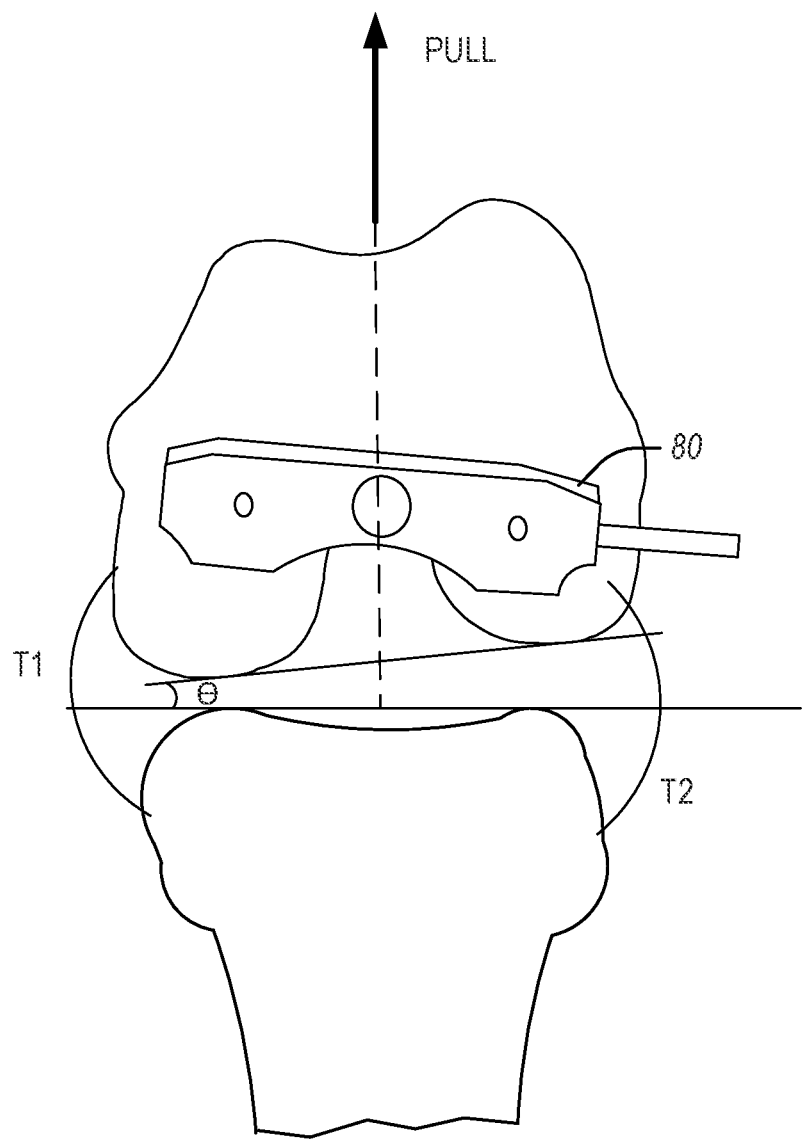
FIG. 8 is a schematic view illustrating an intraoperative soft tissue assessment using a CAS system in knee flexion in accordance with some embodiments.
Figure 9:
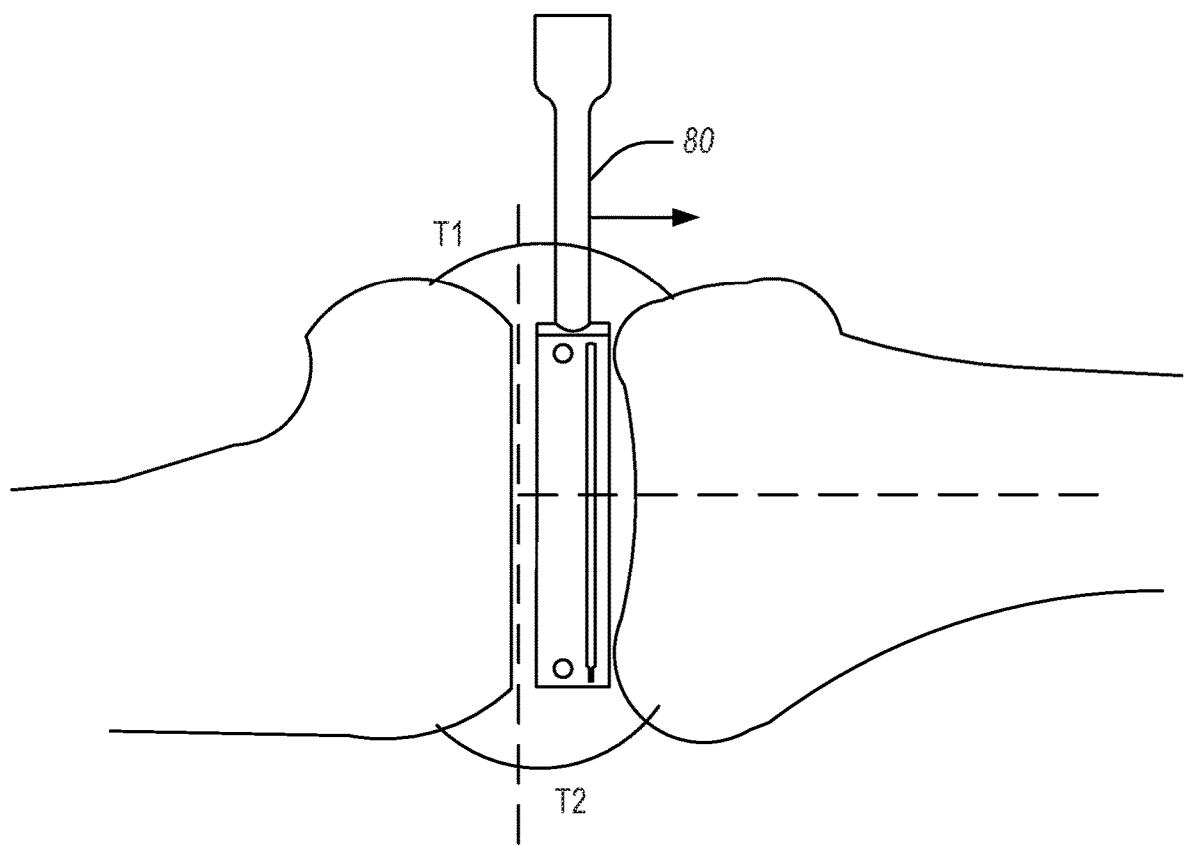
FIG. 9 is a schematic view illustrating an intraoperative soft tissue assessment using a CAS system in knee extension in accordance with some embodiments.
Figures 10A, 10B:
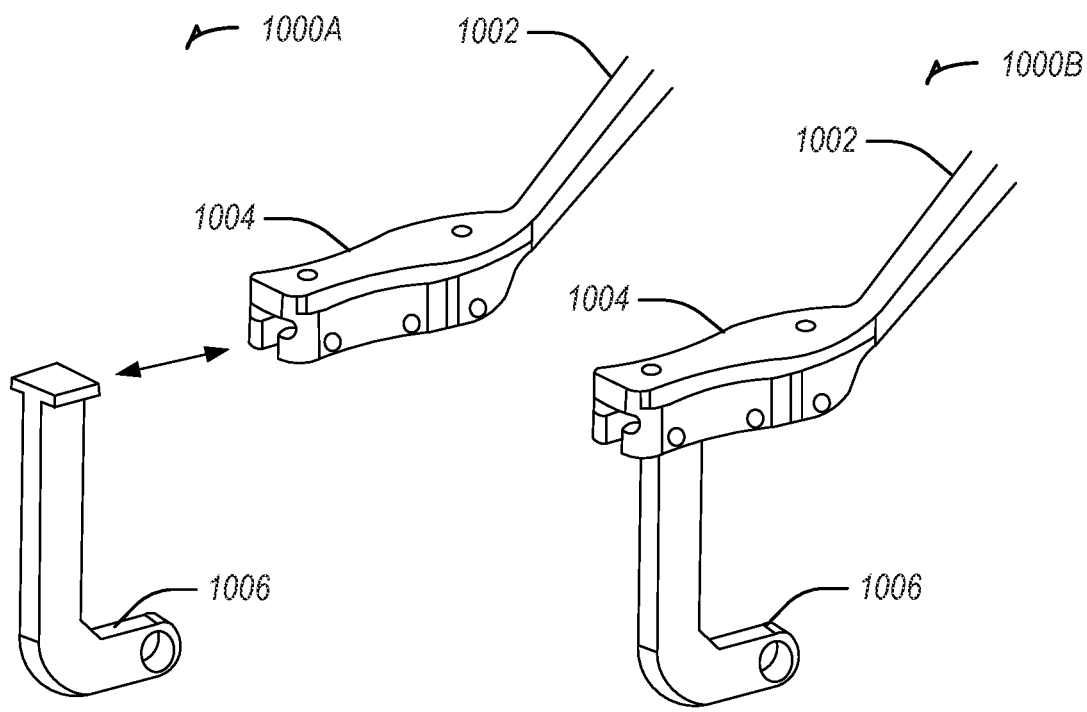
FIGS. 10A-10D illustrate a j-shaped adaptor and a robotic arm for use in a ligament pull system in accordance with some embodiments.
Figures 10C, 10D:
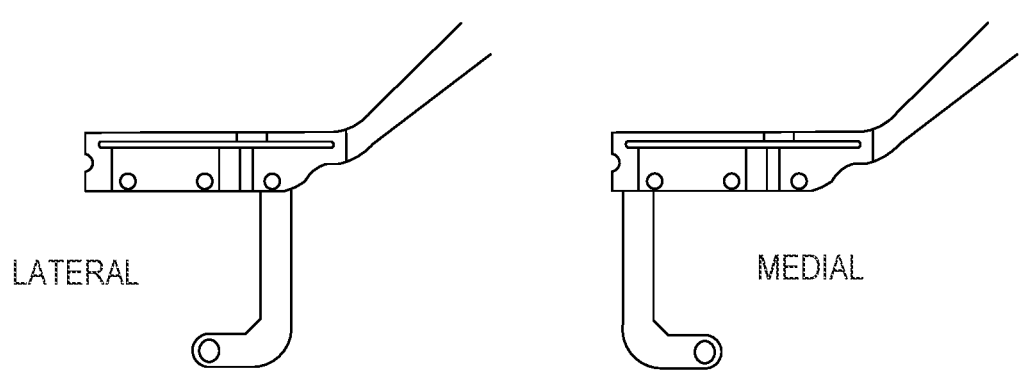

In an embodiment, the CAS controller 50 may operate the robot arm 20 to perform a robotized soft-tissue balancing assessment, such as by using a processor to perform soft-tissue balancing 56, although it may also be done without robotized assistance. Referring to FIG. 8, with a device 80 anchored to the bone (such as a pin, a cutting block, etc.), the robot arm 20 may be driven to pull on the bone and hence put the soft tissue under tension. Applied tension may be controlled using the signals from the force-torque sensors A in the robot arm 20 with the output of the force measurement 52. In an embodiment, the device 80 includes a pin and a cutting block. The robot arm 20 may pull the femur away from the tibia by manipulating the pin of the device 80, such that the pin (and femur) may rotate relative to the robot arm 20. The rotation of the femur will naturally go toward soft tissue balancing, in which tension T1 is equal to tension T2. The device 80 may further include an inertial sensor to measure a rotation θ indicative of the rotation required for soft tissue balancing. The rotation θ may also be monitored and measured by the robot arm 20, with appropriate sensors (optical, encoders, inertial, etc). Referring to FIG. 9, similar operations may be performed with the leg being in extension. FIG. 9 is a schematic view illustrating an intraoperative soft tissue assessment using a CAS system in knee extension in accordance with some embodiments. In an example, the robot arm 20 may pull the femur away from the tibia, either in extension or in flexion, and automatically stop. The robot arm 20 may stop for example at a predetermined distance (gap), when a threshold force or tension is reached, or at a user-selected stopping position. The predetermined distance (e.g., 5 mm, 10 mm, a distance corresponding to a tibia implant thickness such as 10 mm, 11 mm, 12 mm, etc.), may include a safety factor (e.g., +/−1-5 mm), or the like. In an example, a combination of end position markers may be used, such as a predetermined distance approximately equal to a tibia implant thickness (e.g., an insert (poly) or the implant assembly, which may be predetermined using planning techniques), while retaining a maximum force as safety factor. For example, when a maximum force is reached before the predetermined distance, the robotic arm may be stopped. In another example, balanced ligaments may be used to mark the end position.

In FIG. 8, the soft tissue is put under tension using the robot arm 20 acting on the device 80. In an embodiment, the robot arm 20 raises the device 80 to displace the femur, while the tibia remains still by gravity or by its fixation to the table (e.g., when a foot support 30 is used), by a human (e.g., surgical assistant or the surgeon), by surgical tape, self-adherent wrap or tape, or other fixing devices or components to secure the tibia. It is also considered to use the laminar spreaders 25 of the robot arm 20, as in FIG. 3, to spread the bones apart. The laminar spreaders 25 may be inserted in the gap between the femoral condyles and the tibial plateau. In order to assist the laminar spreaders 25, additional devices may be used and manipulated by the robot arm. For example, the spreaders 25 may manipulate a clamp to benefit from the leveraging of the clamp to apply a greater moment at the bones. Likewise, the spreaders 25 may manipulate a spreader with gear mechanism (planetary gear device, rack and pinion, etc), to assist in amplifying the force of the robot arm.

The processor may perform soft-tissue balancing 56 to quantify joint laxity to assist in the soft-tissue balancing at different moments during the surgical procedures operated by the CAS controller 50. For example, the soft-tissue balancing 56 may assess soft-tissue balancing prior to having the robot arm 20 perform the alterations to the bone, to confirm the desired implant sizes and location on the bone produced by the implant assessment 54, or to enable adjustments to the desired implant sizes and location on the bone, and impact the output of the resurfacing evaluator 55. The soft-tissue balancing 56 may assess soft-tissue after cut planes have been made, to determine whether further adjustments are necessary.

In another embodiment, the output D is in the form of a patient-specific cut guide 3D file, for a patient-specific cut guide to be machined or 3D printed for operative use. For example, the patient-specific cut guide may have negative surfaces of the bone model for unique positioning on the bone, such that cut planes and drill guides are placed as planned. As another example, the output D may be a navigation file, of the type programmed into inertial sensor units manually navigated by an operator. Referring to FIG. 9, similar operations may be performed with the leg being in extension.

In an example, the soft tissue assessment may be performed with the leg in flexion (e.g., as shown in FIG. 8) or in extension (e.g., as shown in FIG. 9). When in flexion, the leg may be held at a 90 degrees angle of flexion, or substantially 90 degrees, such as within plus or minus ten degrees. In another example, with the leg in extension, the leg may be held at zero degrees angle of extension, 10 degrees, 20 degrees, or the like, such as based on surgeon preference. The soft tissue assessment may be used to measure or display gap measurements for soft tissue balancing during a test when a knee is in flexion or extension. In an example, the soft tissue balancing assessment when the knee is in flexion may include not releasing the femur when pulling. In another example, the test may include pulling on the femur, then measuring an amount of rotation that results in balance between the soft tissue (e.g., ligaments). The femur may be free to rotate to find the balance based on the amount of force on the ligaments. In an example, the soft tissue balancing assessment may be performed with the patella in place or dislocated.

FIGS. 10A-10D illustrate a soft tissue balancing component, including a j-shaped adaptor 1006 and a robotic arm 1002 for use in a ligament pull system (shown in views 1000A-1000D) in accordance with some embodiments. The j-shaped adaptor 1006 may attach to an end effector 1004 on a distal end of the robotic arm 1002. In an example, the end effector 1004 may be configured to receive the j-shaped adaptor 1006 and lock the j-shaped adaptor 1006 into place, secured to the robotic arm 1002. The attachment of the j-shaped adaptor 1006 to the end effector 1004 may result in an audible click. View 1000A illustrates the j-shaped adaptor 1006 detached from the end effector 1004 and view 1000B illustrates the j-shaped adaptor 1006 coupled to the end effector 1004. View 1000C illustrates the j-shaped adaptor 1006 attached to the end effector 1004 in a configuration for performing a soft tissue balancing test on a lateral portion of a femur and view 1000D illustrates the j-shaped adaptor 1006 attached to the end effector 1004 in a configuration for performing a soft tissue balancing test on a medial portion of a femur. In another example, the j-shaped adaptor 1006 may be configured to be reversible and lock into the end effector 1004 at the same place in each direction, or in four directions (e.g., perpendicular to the lateral or medial views). In an example, the robotic arm 1002 may apply a force to the j-shaped adaptor 1006 to pull the j-shaped adaptor 1006 in a direction while the j-shaped adaptor 1006 is engaged with a femur. Pulling on the femur may allow the ligament pull system to determine a rotation angle for balancing the ligaments of the knee. In an example, the j-shaped adaptor 1006 may be used to pull on the femur with the patella of the knee in place. In an example, the patella or soft tissue may be averted or in a normal position when doing the pull test in flexion.

A bone spike may be used to secure the j-shaped adaptor 1006 to a bone. For example, the bone spike may be placed by a surgeon or using the robotic arm 1002 at a predetermined location on the bone. The j-shaped adaptor 1006 may be fitted around the spike with a spike adaptor anchor located at a distal end of the j-shaped adaptor 1006. The j-shaped adaptor 1006 may be fitted around the spike using the robotic arm 1002, such as automatically, or using force sensing and surgeon input. The j-shaped adaptor 1006 may then be used to apply a force on the bone (e.g., the femur) to pull the bone away form a second bone (e.g., the tibia) to conduct a soft tissue balancing test. The robotic arm 1002 may apply the force on the j-shaped adaptor 1006, which then in turn applies the force on the bone spike, which then applies the force on the bone. The soft tissue balancing test may be performed with the patella or soft tissue in place (e.g., not dislocated) by using the j-shaped adaptor 1006 to avoid the patella or soft tissue. For example, the j-shaped adaptor 1006 may reach around the patella, but remain rigid when the force is applied on the j-shaped adaptor 1006 by the robotic arm 1002, thus pulling the bone (e.g., the femur), while avoiding the patella. A straight component adaptor used instead of the j-shaped adaptor 1006 may be interfered with by the patella and require dislocation of the patella. Performing the soft tissue balancing test with the patella in place may result in more accurate results than performing the soft tissue balancing test with the patella dislocated.

In an example, the robotic arm 1002 may apply a force on the j-shaped adaptor 1006 to cause the j-shaped adaptor 1006 to pull on the bone spike until a threshold force is reached, a threshold tension in the soft tissue is reached, according to a preoperative plan, a surgeon stops the procedure, a predetermined distance is reached, or the like. The predetermined distance (e.g., 5 mm, 10 mm, a distance corresponding to a tibia implant thickness such as 10 mm, 11 mm, 12 mm, etc.), may include a safety factor (e.g., +/−1-5 mm), or the like. In an example, a combination of end position markers may be used, such as a predetermined distance approximately equal to a tibia implant thickness (e.g., predetermined using planning techniques), while retaining a maximum force as safety factor. For example, when a maximum force is reached before the predetermined distance, the robotic arm may be stopped. In another example, balanced ligaments may be used to mark the end position. The j-shaped adaptor 1006 may pull on the bone spike until a distance matching a preoperatively or intraoperatively known thickness of a tibial implant is reached. When the j-shaped adaptor 1006 completes pulling, an angle of rotation of the bone may be recorded (e.g., by surgical planning software, a robotic controller, etc.) for later pin positioning or cut guide placement. In an example, the j-shaped adaptor 1006 may include a horseshoe-shaped adapter (i.e., two j-shaped adaptors connected at their distal ends).

Figure 11:
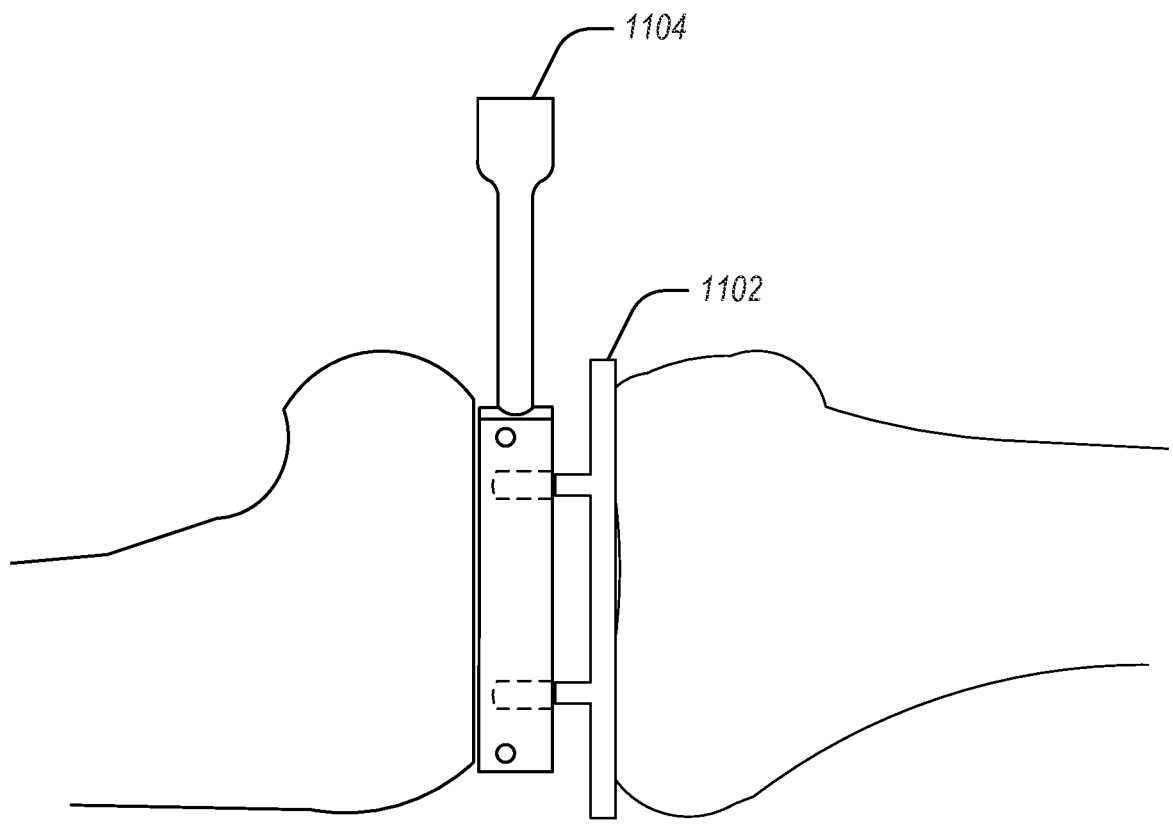
FIG. 11 illustrates a system for testing soft tissue balance in extension in accordance with some embodiments.

FIG. 11 illustrates a system 1100 for testing soft tissue balance in extension in accordance with some embodiments. The system 1100 may be used to measure or display gap measurements for soft tissue balancing during a test when a knee is in extension. For example, an extension gap test may include pulling on a tibia while a knee is in extension. In an example, a spacer block may be placed on a jig 1102, for example with shims or other flat thin surface inserted as the spacer block. For example, a flat attachment may be slid on the jig 1102 to perform the test. The jig 1102 may be attached to a robotic arm 1104, which may cause a force to be imparted onto the flat attachment via the jig 1102. The force may be imparted onto the tibia to pull the tibia away from the femur. In an example, the flat attachment may include one or more feet that may clip into a slot of the jig 1102. The jig 1102 may be used to assess the extension gap and to test varus/valgus angles. In an example, the soft tissue balancing test may be performed at a specified varus/valgus angle. Releases may be performed at that angle until the ligaments are balanced. The ligament balancing may be performed by measuring tension (e.g., by measuring force) within a component, such as using a sensor.

In another example, the soft tissue balancing test when the knee is in extension may include using a plate fixed to the tibia to pull on the tibia. The torque may be measured (e.g., using a sensor) to determine an amount of imbalance. In an example, the test may be performed by a plate that is free to rotate. The free rotation plate may be used to apply force on the tibia until the varus/valgus angles are zero to find a balance. In an example, the jig 1102 may include a spacer block. The spacer block may widen to apply tension to perform a ligament balance test.

Figure 12:
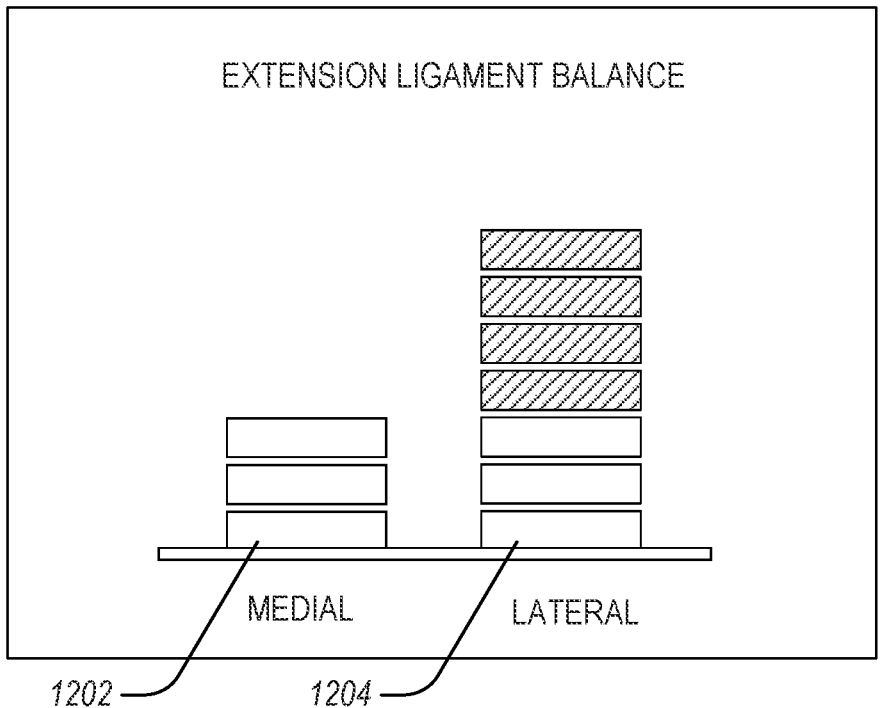
FIG. 12 illustrates an example user interface for displaying ligament balance in accordance with some embodiments.

FIG. 12 illustrates an example user interface 1200 for displaying ligament balance in accordance with some embodiments. The user interface 1200 includes a medial tension indication 1202 and a lateral tension indication 1204. In the example shown in user interface 1200, the medial tension represented in indication 1202 is less than the lateral tension represented in indication 1204. This indicates that the lateral tension should be decreased, such as by performing a release on the lateral ligaments. In an example, lateral tension may include tension between compartments, such as lateral and medial compartments, or collateral ligaments (e.g., medial and lateral collateral ligaments) as an example to differentiate the medial and lateral sides. In another example, all ligament complexes play a role in the balance of the knee, and thus may be balanced. The ligaments may include a medial collateral ligament (MCL), a lateral collateral ligament (LCL), a posterior cruciate ligament (PCL), posterior capsule, etc.

In an example, the difference displayed in the user interface 1200 between the two ligaments may include a difference in force, a difference in torque, or a difference in displacement between the two ligaments. As releases are performed, the user interface 1200 may be updated in real time to display updated differences. For example, a release may be performed on the lateral ligament in the example shown for user interface 1200, which may cause the balance between the medial and lateral ligaments to become closer to even. In an example, a robotic arm may apply a constant force on a bone to allow a surgeon to perform the ligament releases while watching the extension ligament balance in real time. In another example, a robotic arm may be used to perform the ligament releases. The process may be iterated until the ligament balance is achieved.

Figure 13:
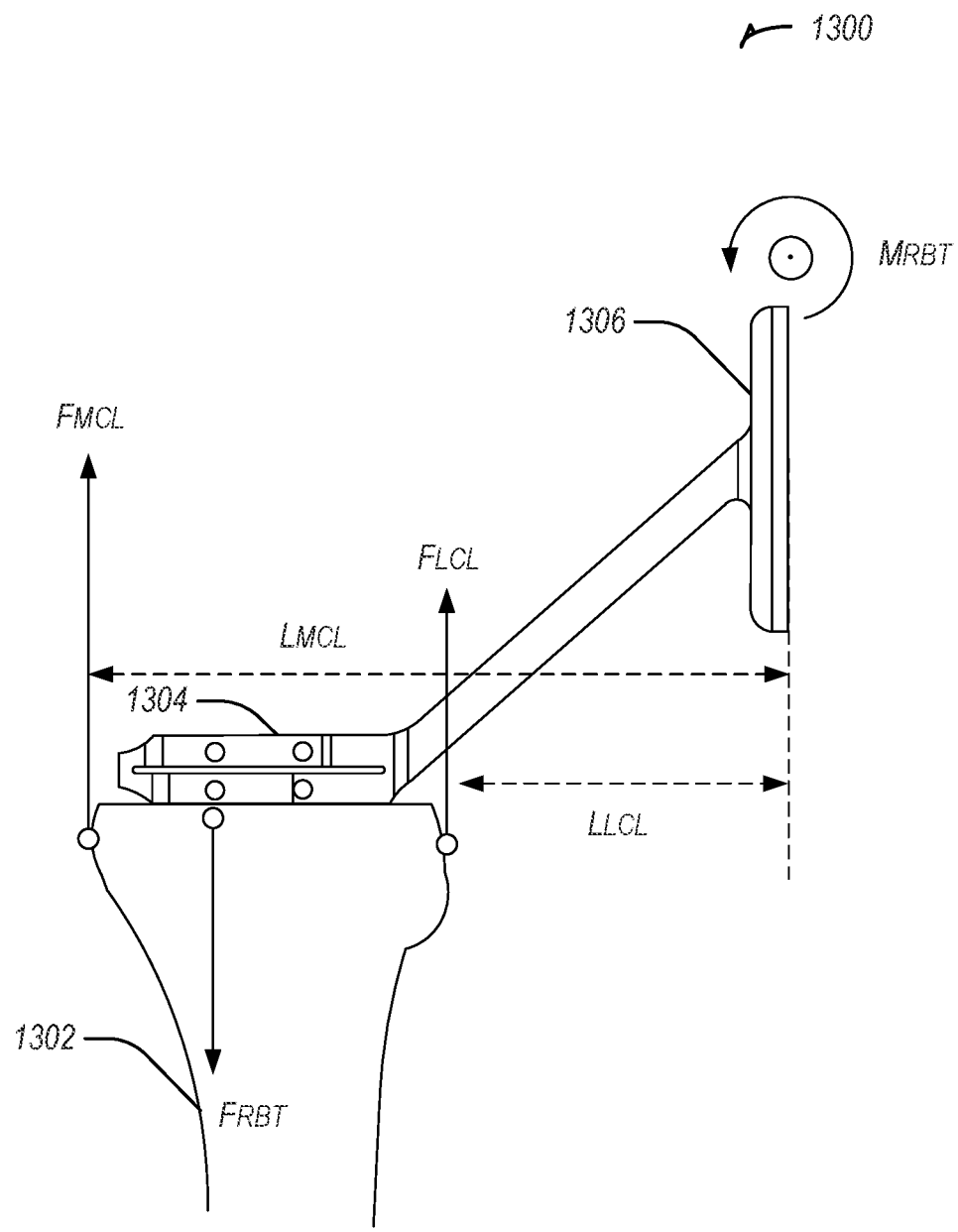
FIG. 13 illustrates a force diagram illustrating a technique for determining medial and lateral forces in accordance with some embodiments.

FIG. 13 illustrates a force diagram 1300 illustrating a technique for determining medial and lateral forces in accordance with some embodiments. The force diagram 1300 illustrates measurements of forces acted on a tibia 1302 by an end effector 1304 of a robotic arm 1306 during a soft tissue balancing test. In an example, a robotic force $F_{RBT}$ is applied by the end effector 1304 on the tibia 1302. Opposite forces are applied by the tibia 1302, which may be effectively labeled a medial force $F_{MCL}$ and a lateral force $F_{LCL}$. The forces are balanced according to Eq. 1 below:

$$F_{MCL} + F_{LCL} = F_{RBT} \qquad \text{Eq. 1}$$

The moment of force (or torque) applied by the robotic arm 1306 may be known using a force or torque sensor, such as between the end effector 1304 and the robotic arm 1306. The moment may be labeled $M_{RBT}$ and may be balanced by moments of equal and opposite torque at medial and lateral distances (labeled $L_{MCL}$ and $L_{LCL}$) from the $M_{RBT}$ moment to the medial force and the lateral force according to Eq. 2 below:

$$F_{MCL} \cdot l_{MCL} + F_{LCL} \cdot l_{LCL} = M_{RBT} \qquad \text{Eq. 2}$$

The lateral and medial distances may be known using a tracking system, such as an optical tracking system, using known dimensions of the end effector, or using sensors attached to components of the system. Using the known $F_{RBT}$ and $M_{RBT}$ and the known distances, Eqs. 1 and 2 may be solved for the $F_{MCL}$ and the $F_{LCL}$. These two forces may be used to determine balance in soft tissue, such as the medial collateral ligament and the lateral collateral ligament. The two forces may be output on a display device or user interface, such as those shown in FIG. 22A-22F or 33A-33D below or FIG. 12 above.

Figure 14:
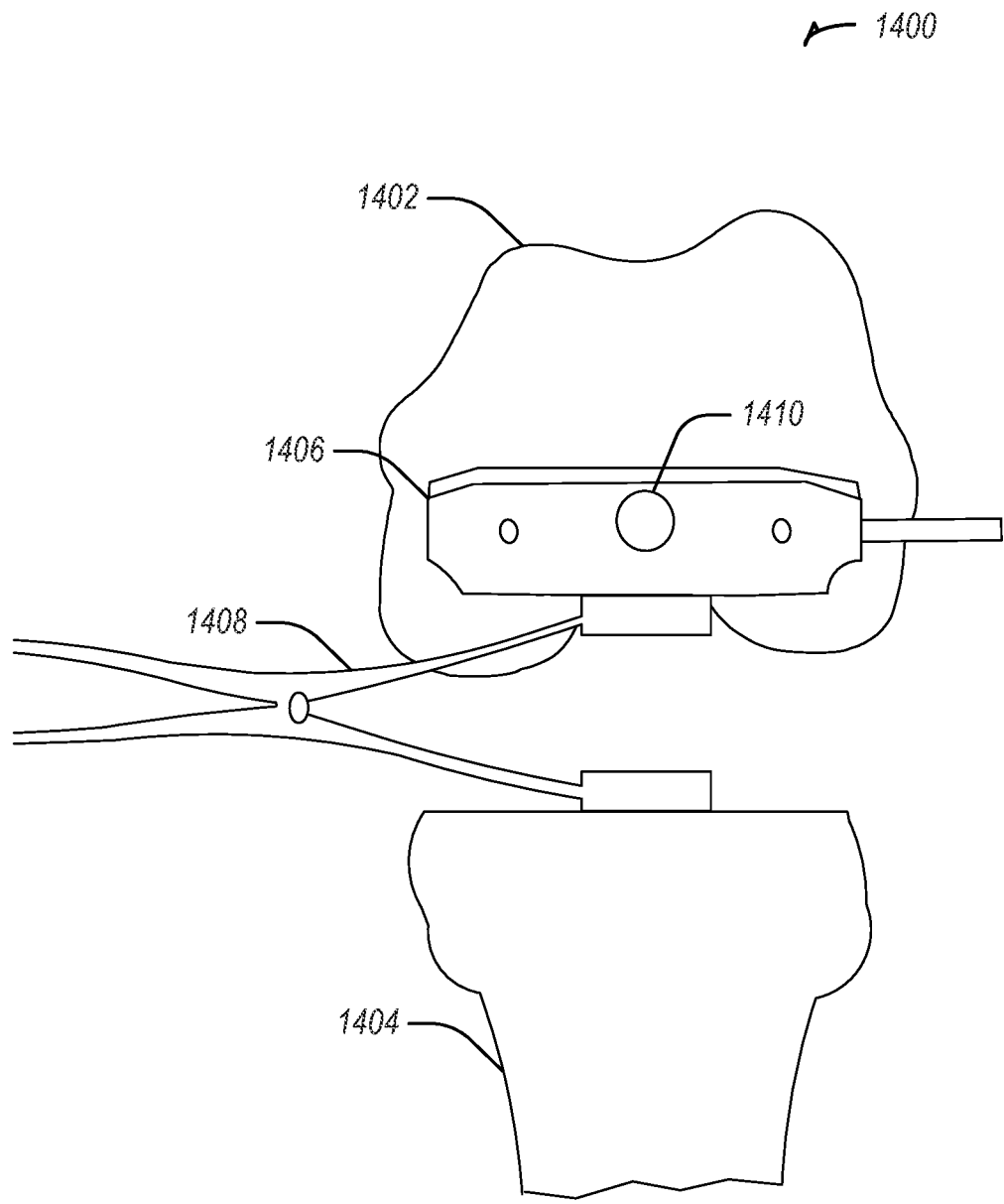
FIG. 14 illustrates a laminar spreader advantage embodiment of a soft tissue balancing test in accordance with some embodiments.
Figure 15:
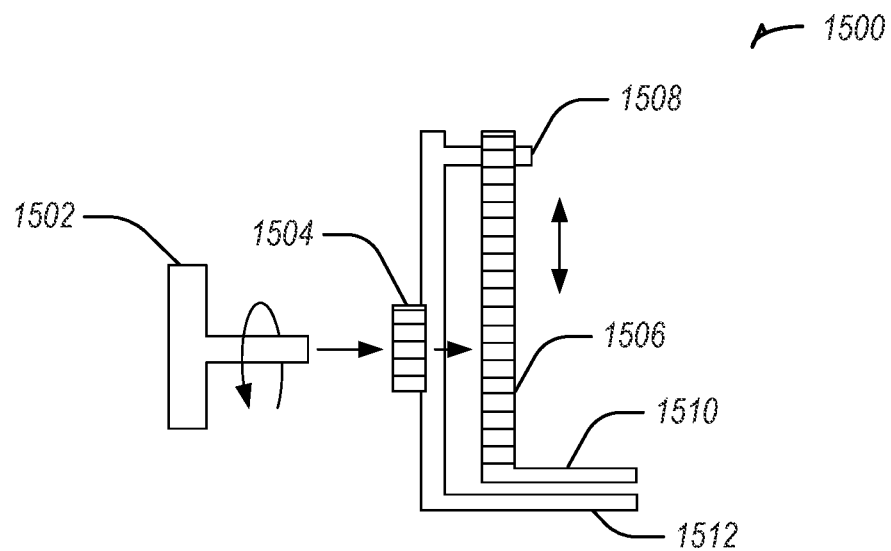
FIG. 15 illustrates a gear advantage embodiment of a soft tissue balancing test in accordance with some embodiments.
Figure 16:
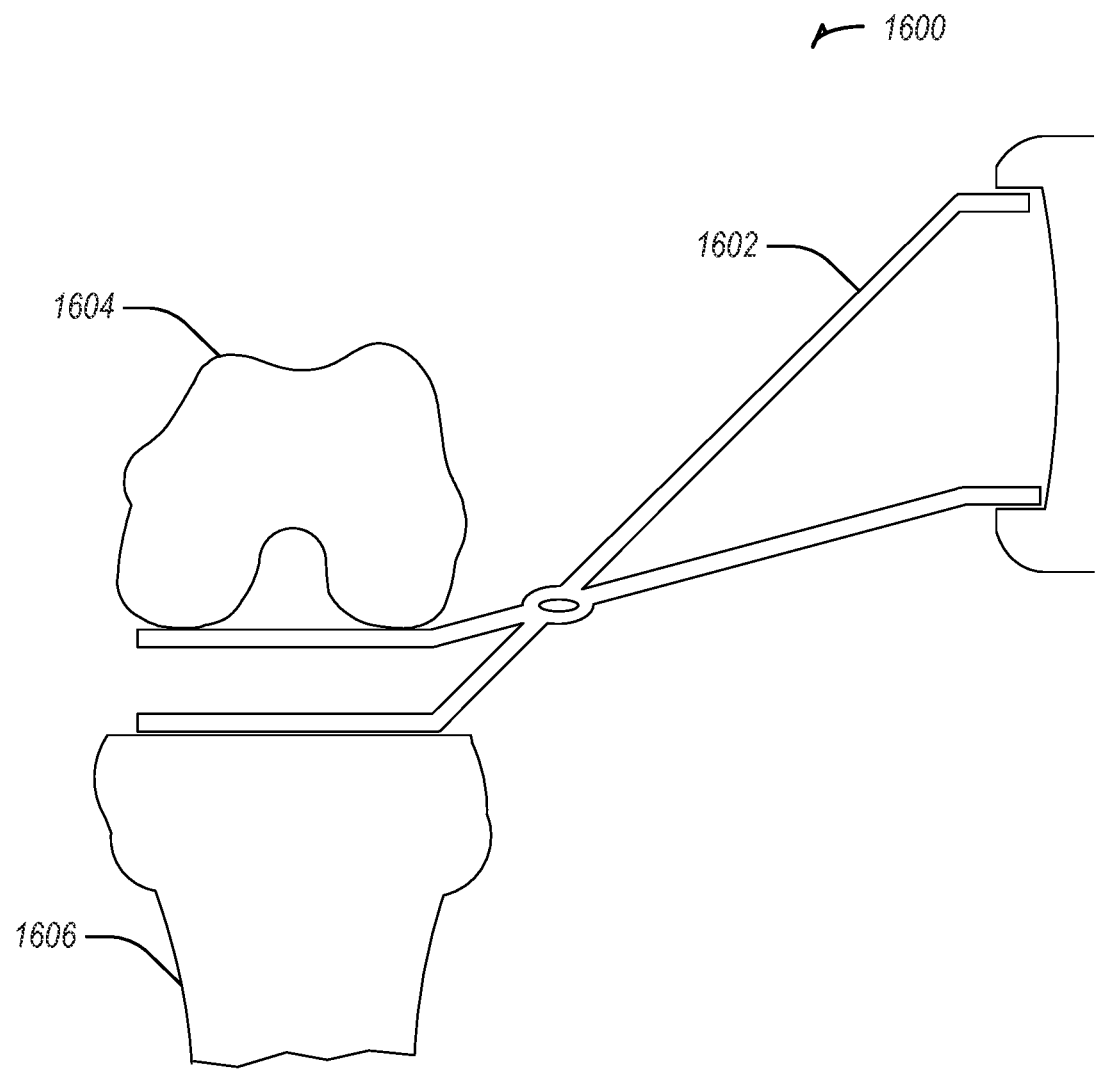
FIG. 16 illustrates a long lever arm advantage embodiment of a soft tissue balancing test in accordance with some embodiments.

FIG. 14 illustrates a laminar spreader advantage embodiment 1400 of a soft tissue balancing test in accordance with some embodiments. FIG. 15 illustrates a gear advantage embodiment 1500 of a soft tissue balancing test in accordance with some embodiments. FIG. 16 illustrates a long lever arm advantage embodiment 1600 of a soft tissue balancing test in accordance with some embodiments. In some cases, a robotic arm may not be able to apply sufficient force to separate the femur and tibia or perform a soft tissue balancing test. To increase the force applied by the robotic arm, a mechanical advantage may be used. For example, the laminar spreader advantage embodiment 1400 illustrates a laminar spreader 1408 to apply additional support while the robotic arm 1406 applies a force at 1410 (e.g., using a bone spike as described herein) on a femur 1402 to separate the femur 1402 from a tibia 1404. In the example shown in FIG. 14, force may be applied to the laminar spreader 1408 by a surgeon (or surgical assistant) or by another robotic arm.

In the example shown in FIG. 15, the gear advantage embodiment 1500 uses a robotic arm 1502 affixed to a gear 1504 to apply a torque on a second gear 1506 to move a pivot joint 1508 to cause a first spreader arm 1510 to separate from a second spreader arm 1512, the first spreader arm 1510 applying a force on a first bone and the second spreader arm 1512 applying a force on a second bone. The gear advantage embodiment 1500 relies on the additional torque of the gears 1504 and 1506 to increase the output force of the robotic arm 1502. In the example shown in FIG. 16, a robotic arm applies force to a laminar spreader 1602 with long lever arms to separate a femur 1604 from a tibia 1606. The torque applied by the robotic arm is increased via the long lever arms.

Figure 18A:
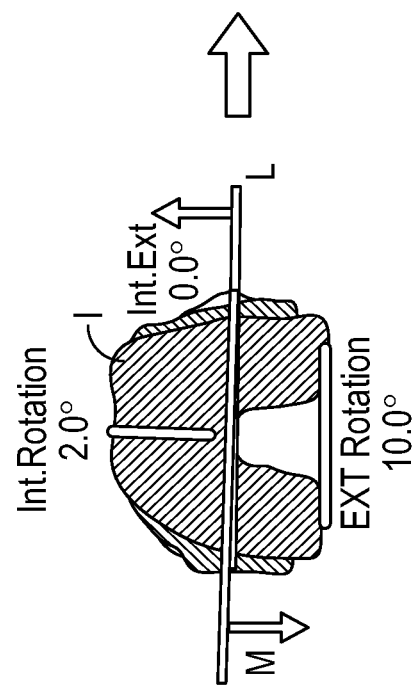

FIGS. 17A and 17B are user interfaces for displaying a range-of-motion (ROM) analysis of a CAS controller in accordance with some embodiments. FIGS. 18A and 18B are user interfaces for displaying an implant assessment of a CAS controller, enabling implant movement from a caudal viewpoint in accordance with some embodiments. FIGS. 19A and 19B are user interfaces for displaying an implant assessment of a robotized surgery controller, enabling implant movement from a frontal viewpoint in accordance with some embodiments.

Referring to FIG. 17B, a graph illustrating an actual varus/valgus balanced line 60 as a function of the leg extension is shown, as a result of the controlled movements of the foot support 30. The force measurement data allows the positioning of 60, as an indication of the varus/valgus value at balanced soft tissue. Lines 61 and 62 respectively show the valgus and varus values at maximum allowable soft tissue tension, as a result of the lateral movements depicted in FIG. 17A, as measured by the force measurement 52. The graph of FIG. 17B is the ROM analysis, done preoperatively or post-operatively.

A similar graph may be produced by the implant assessment 54, to illustrate the impact of given implants at a given location on the bones. However, as shown in FIGS. 18A and 19A, the model of the implant I may be rotated by an operator, with angle values being instantly updated. As a result of such virtual adjustments, the varus/valgus balanced line 60 may shift to reduce the valgus as in 60A (FIG. 18B) or to reduce the varus as in 60B (FIG. 19B). An operator or a processor performing the implant assessment 54 may therefore perform such adjustment in order to bring the balanced line 60 closer to a neutral varus/valgus through as much of the leg extension as possible.

Referring now to FIGS. 20, 21, 22A-F, and 23A-23B, a surgical workflow that may be operated with the CAS system 10 is described, with reference to GUIs 100-130. The expression GUI is used in the plural to indicate a variation of GUI pages in the surgical workflow. The surgical workflow may be the output D produced by the processor of the CAS controller 50.

Figure 20:
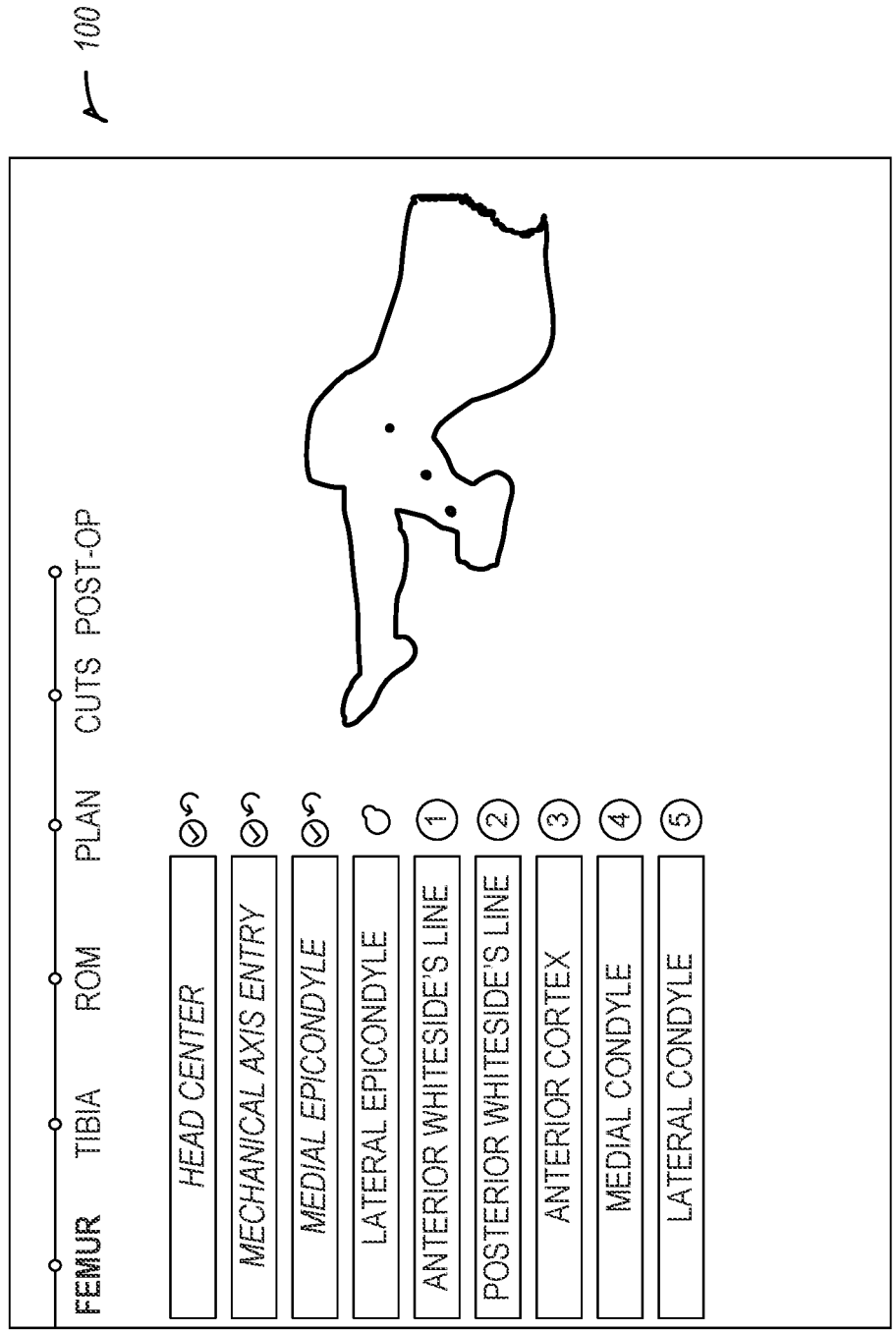
FIG. 20 is an example graphic-user interface (GUI) guiding a calibration (also known as a registration) of a femur for a CAS system in accordance with some embodiments.

Referring to FIG. 20, GUI 100 is provided to guide an operator during calibration (also known as registration) of the bones for subsequent tracking. The calibration is performed so as to position the limbs in a universal X, Y, Z coordinate system. The origin and orientation of the X, Y, Z coordinate system may be arbitrary, or may be fixed to the OR table or any other structural point, or may be even fixed to a bone of the patient. In the example of FIGS. 20, 21, 22A-F, and 23A-23B for total knee replacement, the femur and the tibia of the patient are to be tracked, whereby their position or orientation (i.e., their location) in the coordinate system must be set. The GUI may provide a visual display of the femur, with animation to suggest movements to be performed during the calibration. According to an embodiment, the femoral head center is determined using the processor to perform a ROM analysis 53 to record a plurality of femur positions and orientations, essentially forming a sphere whose center is that of the femoral head. In an embodiment, the points are acquired when the femur is moved in a conical pattern, for example manually. The GUI 100 may guide the operator in indicating the number of positions required, and in confirming that a suitable number of points have been acquired. The GUI 100 may then request that a plurality of known landmarks be digitized with a tracked digitizer tool (e.g., a tracked pointer, wand, or the registration tool described with respect to FIG. 28 below), such as the mechanical axis entry point, the medial epicondyle, the lateral epicondyle, the anterior and posterior Whiteside's lines, the anterior cortex, or the medial and lateral condyles. The acquisition of these points may enable the generation of a cloud of points or surface model that may be matched or merged with the bone model B of the femur (FIG. 1), via the ROM analysis 53. Hence, at the outset of the steps directed by GUI 100, the femur is tracked in the coordinate system.

Figure 21:
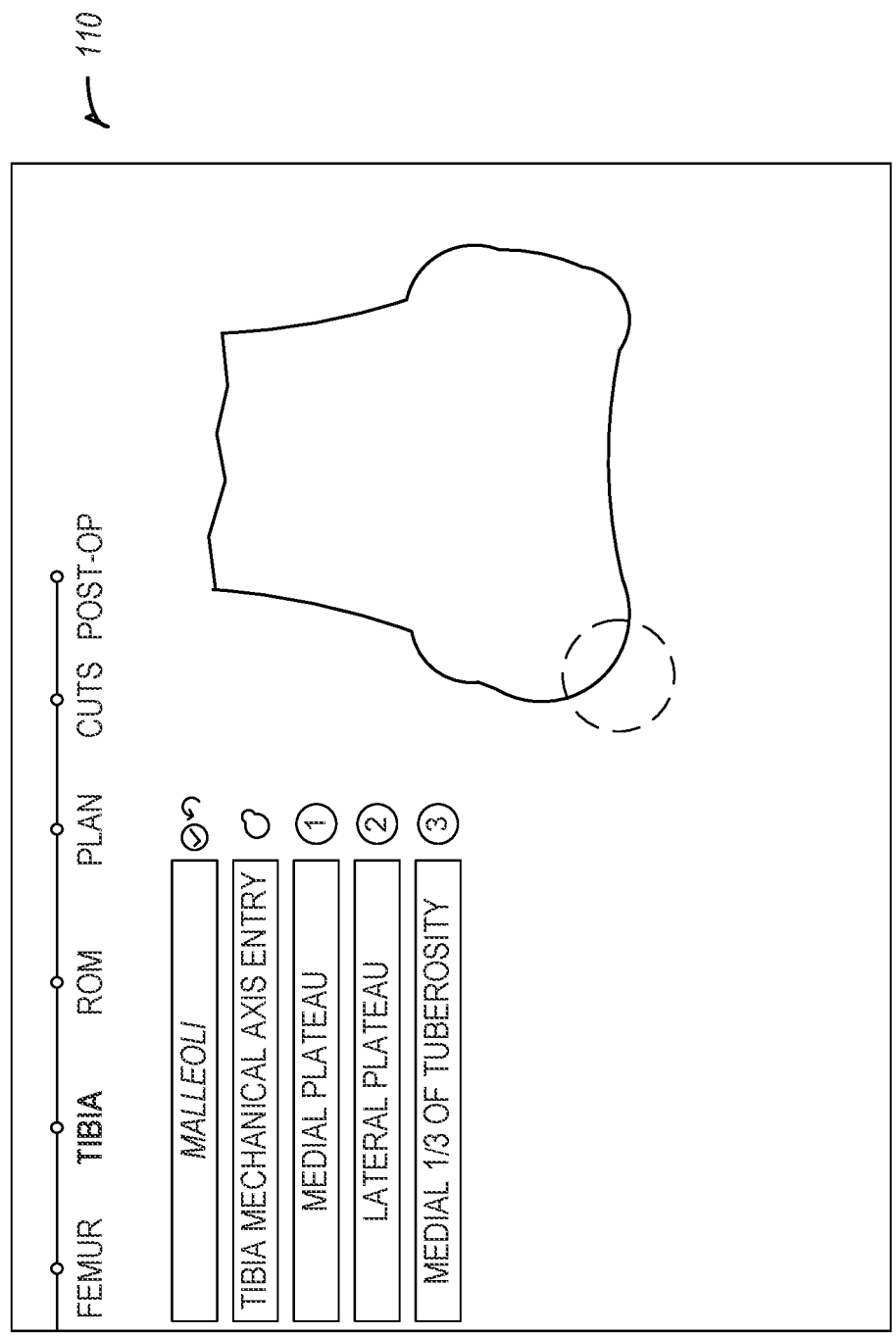
FIG. 21 is an example graphic-user interface (GUI) guiding a calibration (also known as a registration) of a tibia for a CAS system in accordance with some embodiments.

Referring to FIG. 21, GUI 110 is also provided to guide an operator during calibration (also known as a registration), but for a second bone, i.e., the tibia, to locate the tibia in the X, Y, Z coordinate system. The GUI 110 may request that a plurality of known landmarks be digitized with a tracked digitizer tool, such as the malleoli, the tibial mechanical axis entry point, points on the medial plateau and on the lateral plateau, or other points such as the medial ⅓ of tuberosity. Although not shown, the GUI 110 could suggest that a pivoting motion of the tibia relative to the femur be done to record the movement via the tracking device 70 and use the information to determine a mechanical axis of the tibia. As observed from FIG. 21, the GUI 110 may provide assistance by visual showing the regions of the tibia and fibula in which points are to be digitized. The acquisition of these points may enable the generation of a cloud of points or surface model that may be matched or merged with a bone model B of the tibia (FIG. 1), via the ROM analysis 53. Hence, at the outset of the steps directed by GUI 110, the femur and tibia are tracked in the coordinate system.

Referring to FIGS. 22A-22F, GUI 120 is used to guide the gathering of range-of-motion data of the tracked limbs, tracked in the coordinate system pursuant to the steps performed using GUIs 100 and 110. In an embodiment, the GUI 120 guides a human operator, such as a surgeon or medical professional, in determining the limits of the range of motion and of joint laxity, based on force felt by the operator, as an alternative to using the force feedback capability of the robotized version of the system 10. According to FIG. 22A, a lateral leg display 121 may be provided to visually illustrate the limits of flexion and extension, with related angle. The operator manually displaces the tibia relative to the femur between maximum (flexion) and minimum (extension) angles, and the tracking of the tibia and femur by the tracking device 10 allows the processor to record these angles for use in the ROM analysis 53. The operator may assist in determining the maximum and minimum angle, by judging when to stop the extension and flexion based on the resistance felt. The leg display 121 may present the measured data in different forms, using for instance a movement arch 121A to visually show the range of movement. A ROM bar 121B may also be provided, showing the numerical values of angle, including a median angle. When the extension angle value is outside of standards, the ROM analysis 53 may identify potential flexion contracture to influence the resection planning to remedy this issue. When the overall range of motion is below acceptable standards, the ROM analysis 53 may identify this condition to influence resection planning and implant selection.

Figure 22A:
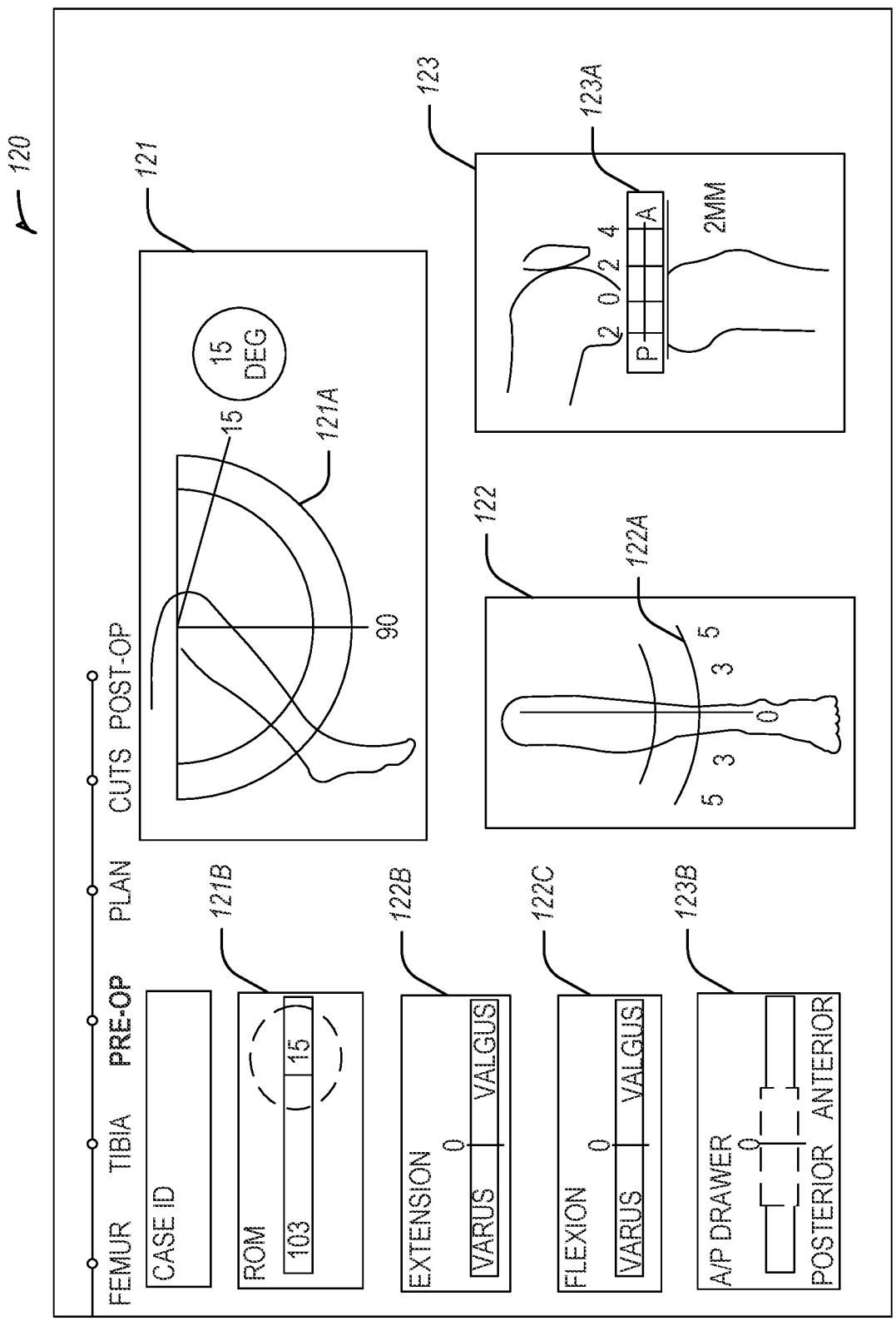
FIGS. 22A-22F are example graphic-user interfaces (GUI) guiding a quantification of joint movement for a CAS system and displaying varus and valgus angles of a knee in accordance with some embodiments.
Figure 22B:
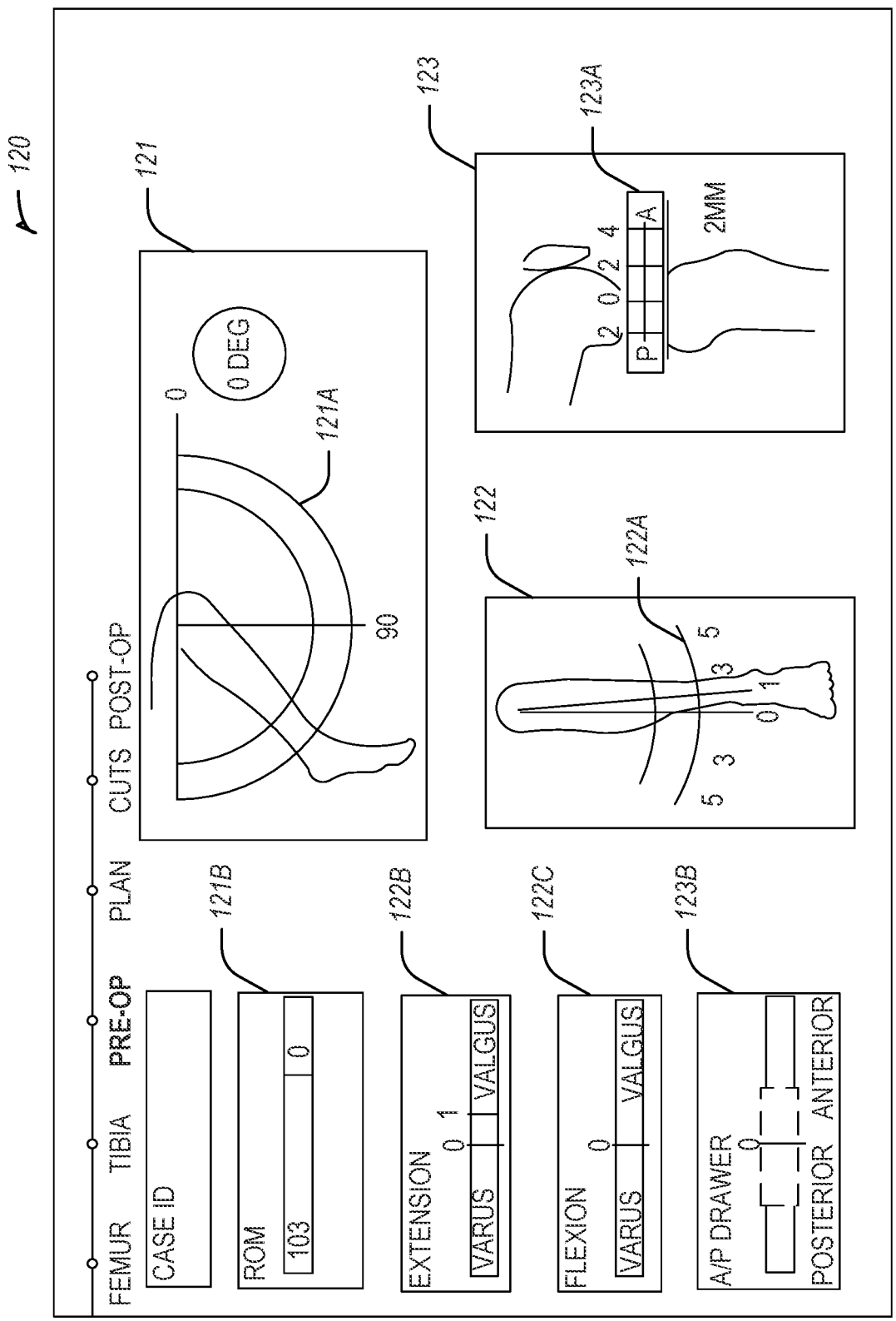

According to FIG. 22B, a frontal leg display 122 may also be provided in GUI 120 to visually illustrate the varus/valgus angles at extension and flexion. In a first step, the operator manually extends the leg, to then pivot the tibia relative to the femur to maximum varus and valgus angles, and the tracking of the tibia and femur by the tracking device 70 allows the ROM analysis 53 to use these angles. The maximum varus/valgus angles may be determined by the operator's judgement as to when to stop the extension and flexion based on the resistance felt. The frontal leg display 122 may provide the data in different forms, using also for example a movement arch 122A to visually show the range of movement, and an extension varus/valgus bar 122B, showing the numerical values of varus and valgus.

Figure 22C:
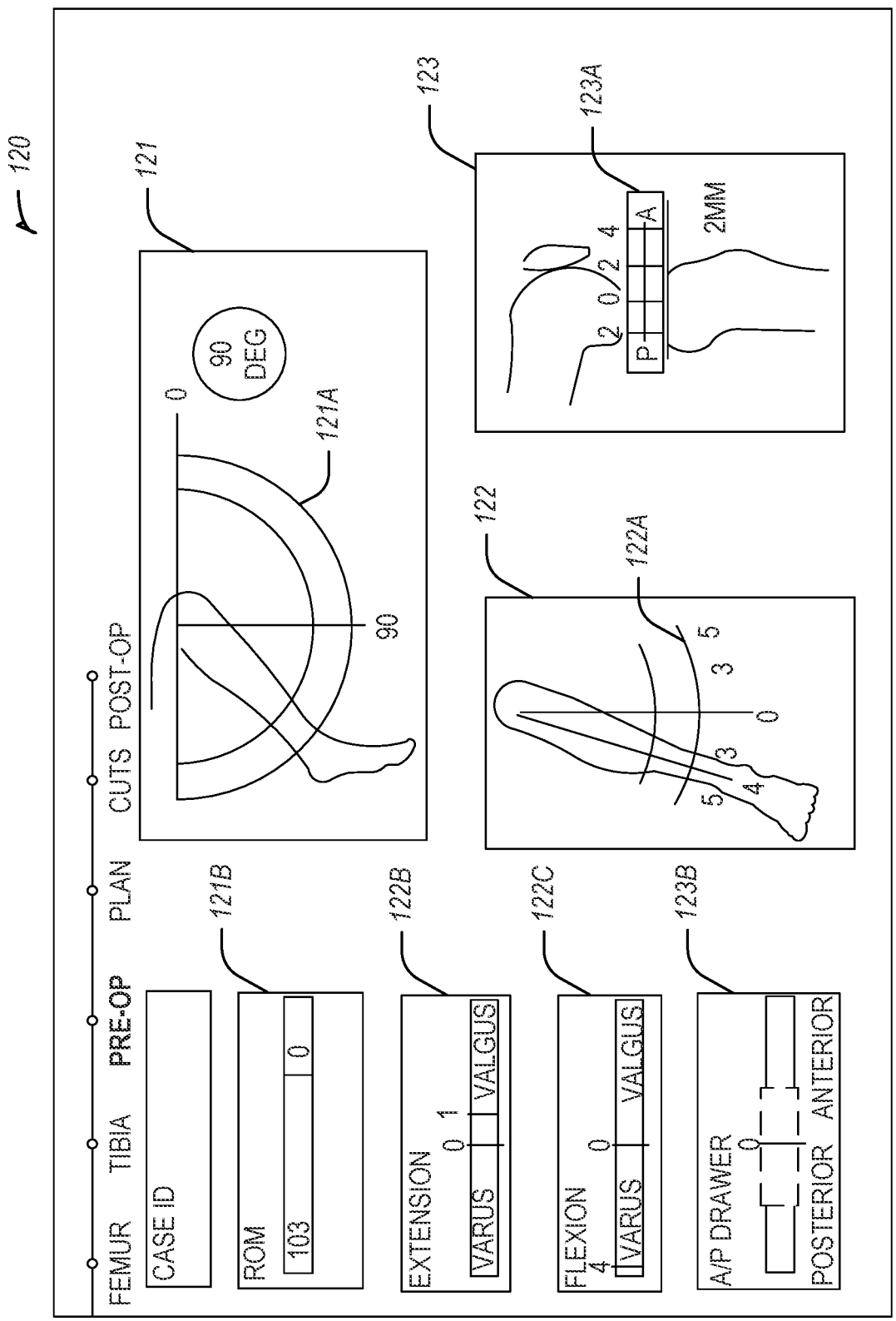

Then, according to FIG. 22C and using the same or another fontal leg display 122 and movement arch 122A, the operator manually flexes the leg, to then pivot the tibia relative to the femur to maximum varus and valgus angles, and the tracking of the tibia and femur allows the ROM analysis 53 to use these angles. A flexion varus/valgus bar 122C may then show the numerical values of varus and valgus. These values are recorded for subsequent use by the processor in performing the soft tissue balancing 56. Moreover, these values may indicate a loose or tight knee condition, laterally or medially, whether it be correctable by implant positioning or not. In the latter case, the system 10 may suggest ligament releasing to remedy the condition. The soft tissue balancing 56 may identify such a condition by being programmed with acceptable varus/valgus angle ranges. The varus/valgus angles obtained may be representative of the laxity of the medial and of the lateral collateral ligaments, as these ligaments delimit knee laxity. When the posterior and the anterior cruciate ligaments have not been resected (e.g., in a cruciate retaining surgery), these ligaments may also affect laxity. The knee articular capsule and the patellar tendon may also affect joint laxity.

Figure 22D:
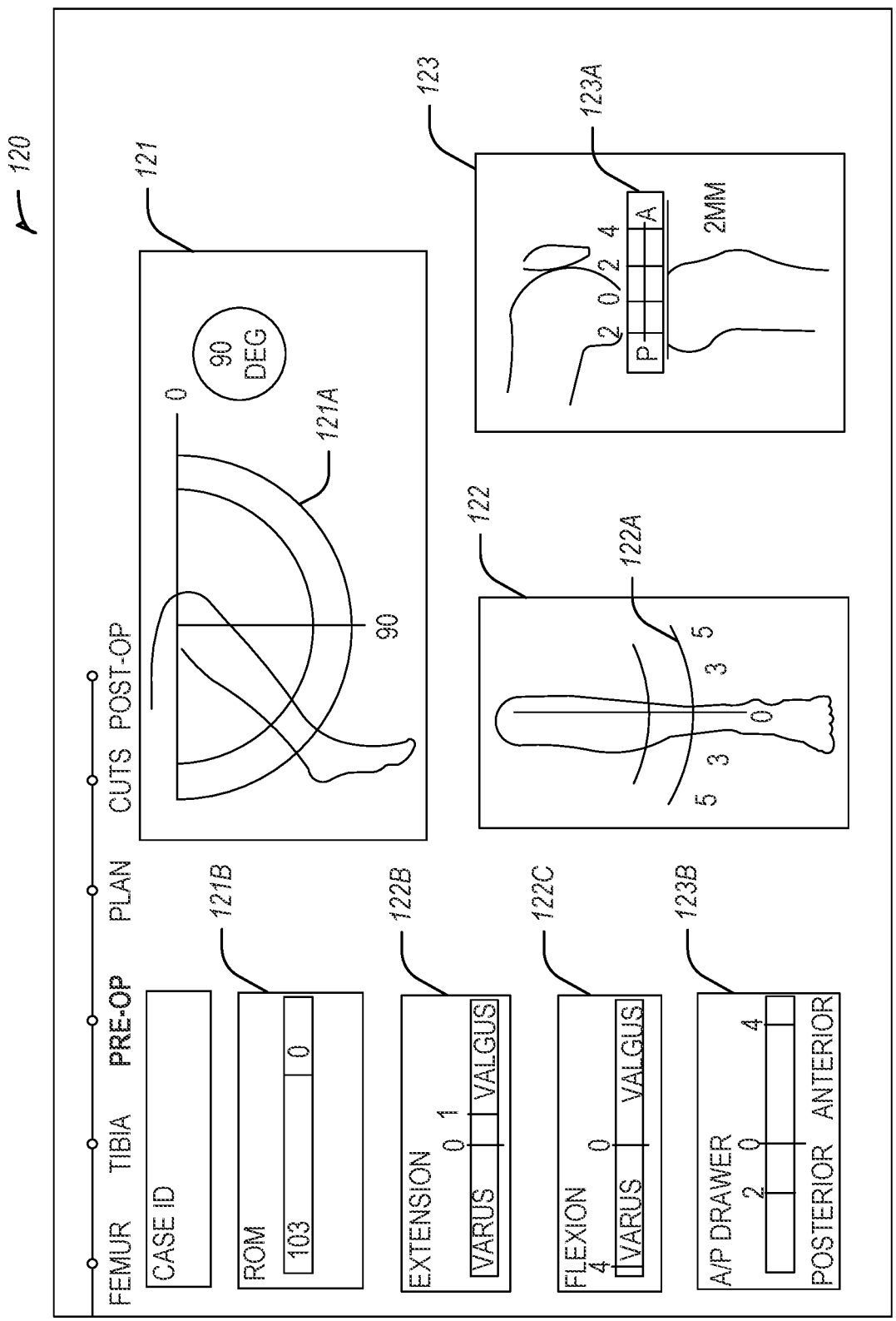

Referring to FIG. 22D, an enlarged joint display 123 may also be provided to visually illustrate the anterior and posterior drawer distances at flexion. To gather the information, with the leg flexed, the operator manually pushes and pulls the tibia relative to the femur to maximum posterior and anterior positions, and the tracking of the tibia and femur by the tracking device 70 allows the ROM analysis 53 to use the drawing positions, relative to a neutral position at which the tibia is natively positioned relative to the femur by soft tissue tension. Again, the maximum distances may be determined by the operator's judgement as to when to stop the pushing and pulling based on the resistance felt. The joint display 123 may have different forms, using a distance scale 123A to visually show the range of movement, and a distance bar 123B, showing the numerical values of varus and valgus. These values are recorded for subsequent use during the soft tissue balancing 56. Joint displays 123A and 123B may also indicate a target laxity (for comparison) which is programmed to reflect the ideal laxity. The ideal laxity may be based on a surgeon-defined preference or suggested value from literature.

Therefore, at the outset of the surgical workflow steps guided by GUI 120, the system 10 has recorded joint laxity data. The recorded information may be based on force feedback felt by the surgeon manipulating the tibia relative to the femur, or may be the result of manipulations by robotized components using sensors A and output by the force measurement 52 when the robotized components are programmed to limit force values. The recorded range of motion and joint laxity information may include maximum flexion angle, maximum extension angle, range of motion, varus and valgus angle values at extension, at flexion, or at any desired angle, anterior drawer distance, posterior drawer distance. The recorded information may be as a function of 3D bone models B of the tibia and femur, or of other bones in different surgical procedures. The order of information gathering using the GUI 120 may be changed from the order described above.

Figure 22E:
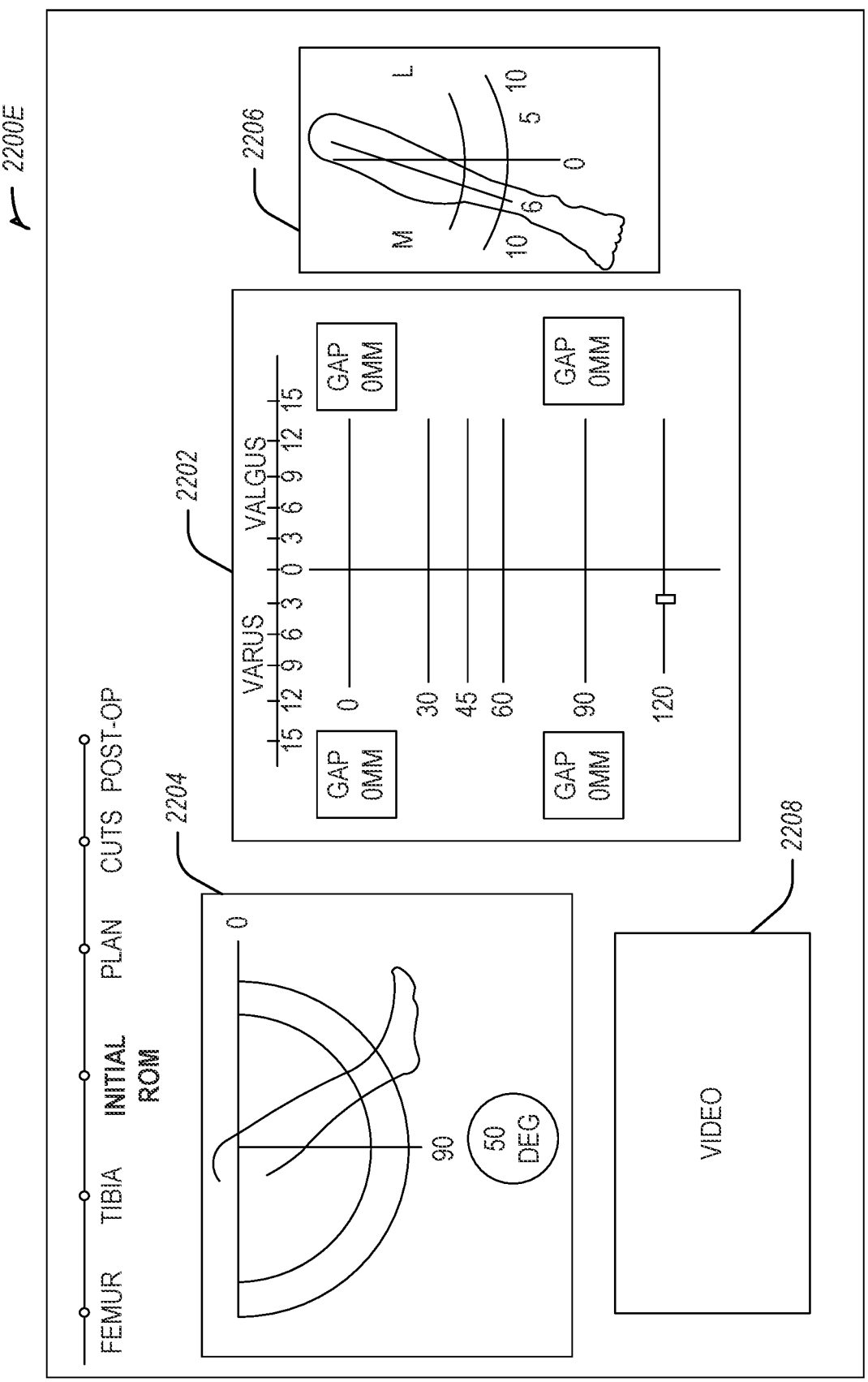
Figure 22F:
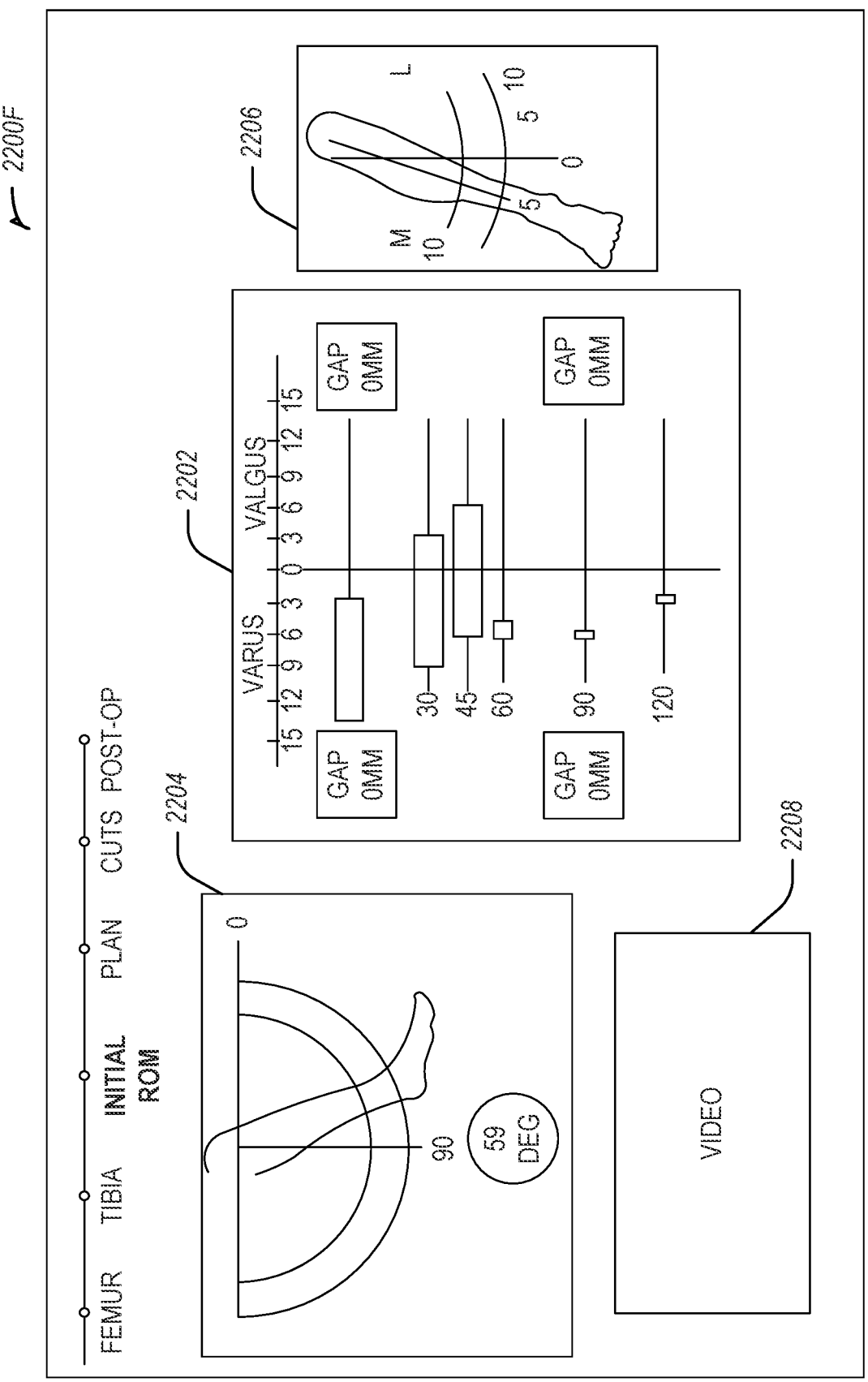

FIGS. 22E-22F illustrate graphical user interfaces (GUIs) 2200A and 2200B, which may be used for displaying flexion/extension angle, gaps, varus and valgus angles of a knee in accordance with some embodiments. The GUIs 2200A and 2200B include a video component 2208 to display real-time range of motion. The GUIs 2200A and 2200B include one or more graphical information components. For example, GUI 2200A shows the varus/valgus angle 2206 at 6 degrees varus in the medial direction at an flexion angle 2204 of 50 degrees (from full extension at 0 degrees). GUI 2200B shows the varus/valgus angle 2206 at 5 degrees varus in the medial direction at an flexion angle 2204 of 59 degrees (from full extension at 0 degrees). Additional information is shown at graphical information component 2202 in the GUIs 2200A and 2200B. The graphical information component 2202 includes gap information, varus/valgus angle information, range of motion information, and extension/flexion information. The range of motion information may be used to create a preoperative plan.

In an example, one or more of the GUIs 2200A or 2200B may provide a remote video or allow for a remote audio connection, such as with a remote surgeon. The remote video or remote audio may be a real-time connection to allow the remote surgeon to discuss a procedure or provide training with a local surgeon or to monitor the local surgeon. A GUI used by the remote surgeon may provide the remote surgeon with a video display of a surgical field operated by the local surgeon.

Figure 23A:
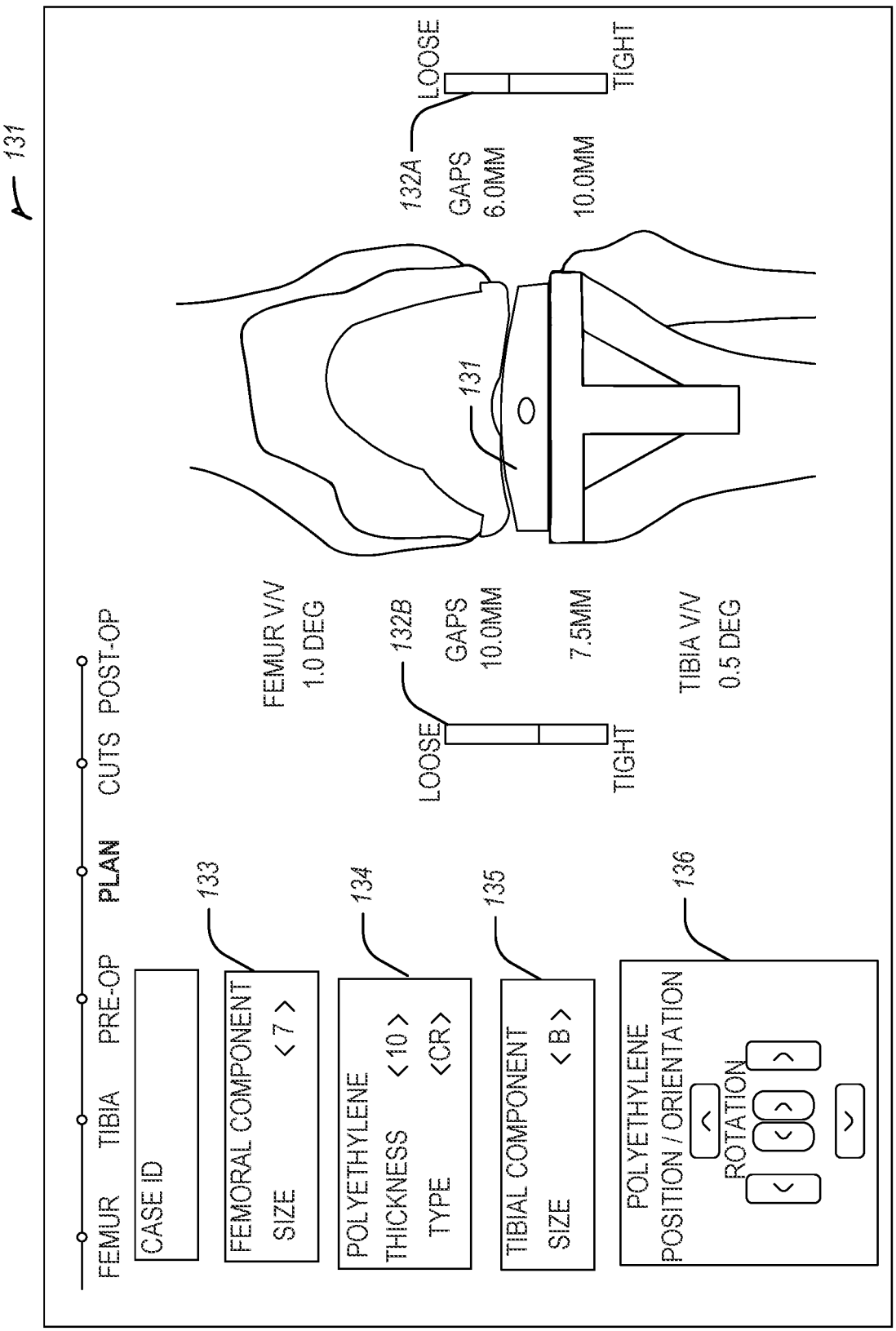
FIGS. 23A-23B are example graphic-user interfaces (GUI) for planning implant selection and locating, and for assessing resection intraoperatively or post-operatively in accordance with some embodiments.
Figure 23B:
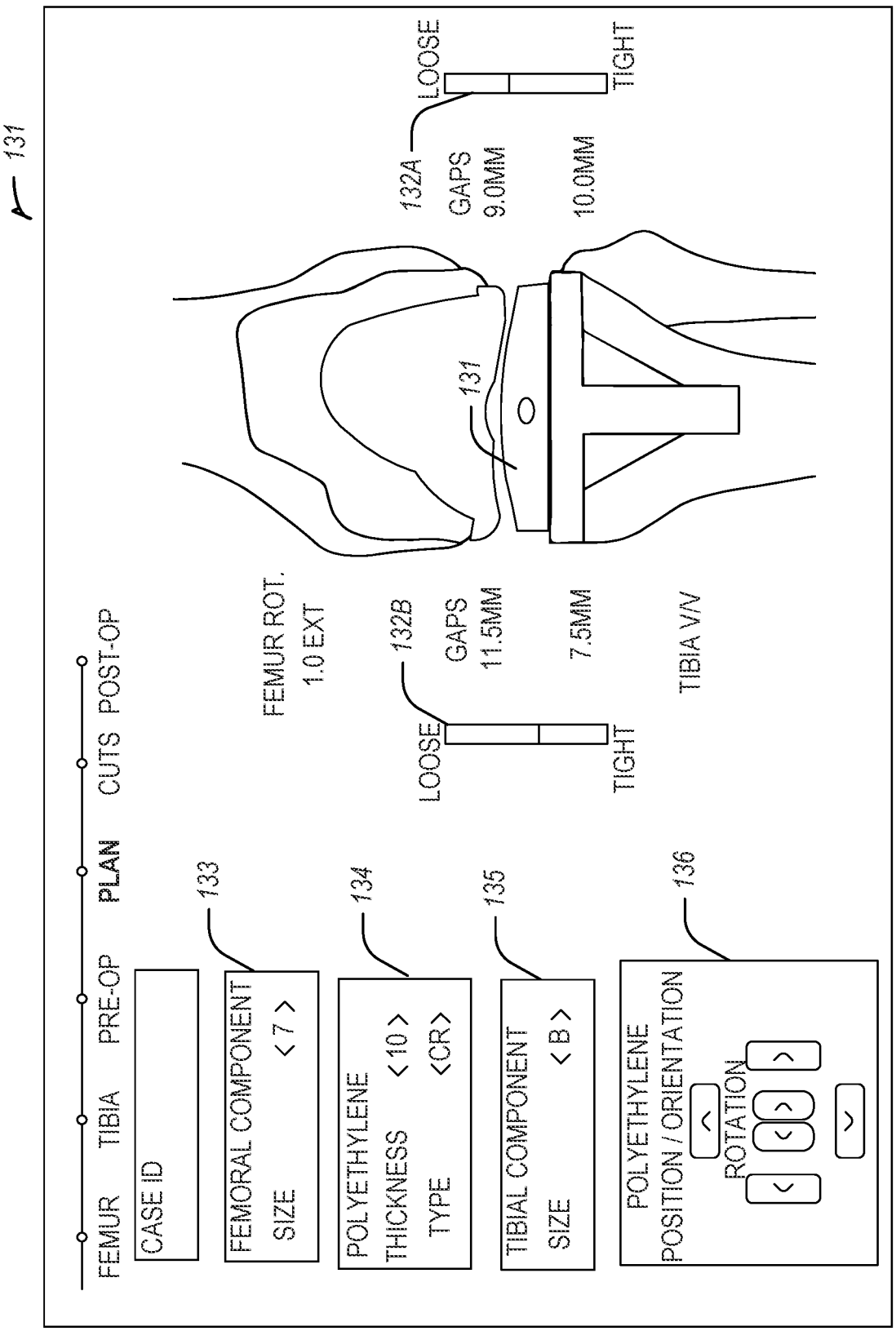

Referring to FIGS. 23A and 23B, GUI 130 is used for the planning of the implant positions and orientations, taking into consideration joint laxity and range of motion as obtained using GUI 120. The GUI 130 receives output from the implant assessment 54 and from the soft tissue balancing 56. The GUI 130 may have a joint display 131 showing bone models B with implant models C. The joint display 131 may include a view of the knee in extension (FIG. 23A) and a view of the knee in flexion (FIG. 23B). According to an embodiment, the user of GUI 130 may toggle between flexion and extension views, and may also toggle between frontal (FIGS. 23A and 23B), sagittal or axial planes of view, on preference. The initial or proposed location of the implant models C relative to the bone models B may be determined by the implant assessment 54 using the joint laxity data output by the soft tissue balancing 56. The current location may be quantified using different markers, such as those described below. Joint-line variation plane 131A may display the pre-operative joint line versus the proposed joint line or the current joint line (i.e., actual location, as modified) when an operator varies the location of either one of the implant models C. Lateral laxity scale 132A and medial laxity scale 132B may provide a visual indication of the acceptable lateral and medial soft tissue tension. In FIGS. 23A and 23B, the acceptable range is indicated by upper and lower limits, along with a pointer indicating the tension at the current implant locations. The scales 132A and 132B may also provide gap distances, current femur and tibia varus/valgus angles, and an anterior gap for patellofemoral joint stuffing as additional data representative of joint laxity. The gap distances may be the sum of planned resection and ligament laxity compared to implant thickness. According to an embodiment, the laxity scales 132A and 132B dynamically reflect modifications to the planned implant location. The adjustments on the laxity scales 132A and 132B may be reflected by the graphs shown in FIGS. 18B and 19B, as a function of a rotation of the implant. A femoral component window 133 may enable the change of femoral implant size. The user may have the possibility of changing implant sizes, in which case the displayed femoral implant model and related information on the joint display 131 may be updated (131A, 132A, 132B, etc.). A spacer component window 134 may enable the selection of the spacer thickness or the type of spacer. Changes to the spacer component may result in a dynamic update of the joint display 131 and of related data (131A, 132A, 132B, etc.). A tibial component window 135 may enable the change of tibial implant size, with the user given the option of changing implant sizes, in which case the displayed tibial implant model and related information on the joint display 131 may be dynamically updated (131A, 132A, 132B, etc.). A location control panel 136 is provided for the user to modify the location of the femoral component relative to the femur, in translation or location. As the location is modified using the location control panel 136, the joint display 131 may be updated and applicable data is also adjusted, such 131A, 132A, 132B, etc. Alternatively or additionally, the implants in the joint display 131 may be widgets that may be moved around relative to the bone models B, with the consequential dynamic adjustment of applicable data (e.g., 131A, 132A, 132B). The widget feature may be available in all views. It has the same function whether it is overlaid on the knee or on the left panel of GUI 130: it allows the user to position/orient the implant with respect to the bone. The effect of changing position or orientation of the implant will be dynamically reflected in the laxity scales. The laxity scales will be different in flexion and extension. The laxity scales could be provided throughout all angles of flexion.

Accordingly, the processor may perform the implant assessment 54 or the soft tissue balancing 56, and may propose implant components and locations for the implant components via the GUI 130. The GUI 130 gives the possibility to an operator to modify the implant components or their locations, by dynamically updating in real-time quantitative data related to joint laxity and range of movement, to assist the operator is finalizing the resection planning. When the implants are selected and their locations are set, the information of the GUI 130 is converted into another form of the output D, such as personal surgical instrument tool files or data to perform resection as decided, a navigation file for the robot arm 20 when present, or a navigation file for tracked tools. The GUI 130 may also be used post-resection, to provide the joint laxity data for the "as-resected" state. The data may be used to document the surgical procedure. This may also allow post-resection corrections when deemed necessary. It may be required to return to GUI 100 or 110 to recalibrate the bones to obtain more precision in the assessment.

Figure 24:
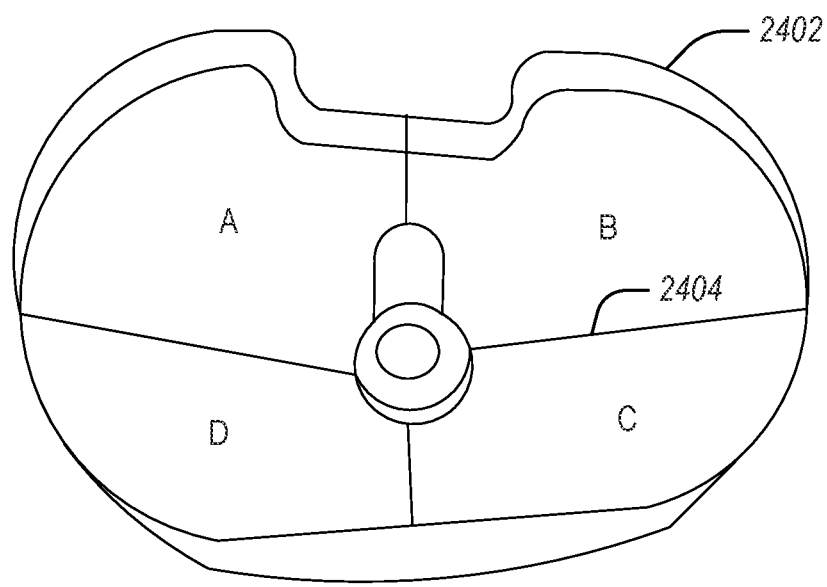
FIG. 24 illustrates a tibial force detection system in accordance with some embodiments.

FIG. 24 illustrates a tibial force detection system 2400 in accordance with some embodiments. The tibial force detection system 2400 includes a tibial baseplate 2402 including one or more force detection components. In an example, the tibial baseplate 2402 includes four force detection components, corresponding to four quadrants, which are labeled in FIG. 24 as quadrants 'A', 'B', 'C', and 'D'. The quadrants may be divided such that each quadrant is moveable independently in at least one axis relative to the other quadrants. For example, dividing line 2404 illustrates a separation between quadrants B and C, such that quadrants B and C may be compressed or decompressed relative to each other. The force detection components may be located within the quadrants (e.g., within the tibial baseplate 2402 (e.g., underneath a first layer shown in FIG. 24). As a quadrant is compressed or decompressed, the force detection component corresponding to that quadrant may include a sensor to detect the compression force (or measure a decompression force or change in force). In another example, the quadrants may be immovable relative to each other, while still including corresponding force detection components to measure force in each quadrant independently. In yet another example, the tibial baseplate 2402 may be divided into halves, with each half including a corresponding force detection sensor and being moveable relative to the other half. In yet another example, further subdivisions may be made of the tibial baseplate 2402 including corresponding force detection components and independent movement (e.g., six, eight, etc., radial slices of the tibial baseplate 2402). The force detection components may be used to obtain data regarding force imparted on the tibial baseplate 2402 intraoperatively.

In an example, the knee may be opened and a navigated tibial cut may be made. In an example, variances in the tibial cut may be related to a depth of the cut, which may be relatively standard for most surgeons taking reference from either the high or low tibial plateau. Once the tibial cut has been made the tibial force detection system 2400 may be placed. The tibial force detection system 2400 may include a tibial baseplate and a polyethylene trial combination. The tibial force detection system 2400 may expand medially and laterally, such as to accommodate various sized knees. In an example, the tibial force detection system 2400 may have a medial or lateral tilting hemi-plateau with the ability to rise and fall all four quadrants independently. The displacement up and down and the force experienced by each quadrant may be measured, such as electronically or hydraulically using a sensor. In an example, the tibial force detection system 2400 may be an active device such that upward or downward movement may be measured as the knee (e.g., before femoral cuts are performed) is put through a range of motion test. In an example, measuring the movement during the range of motion test may be performed while tracking the patella. In an example, varus or valgus forces may be applied, such as by a robotic arm on the knee or by a surgeon through a range of motion (e.g., the entire range or a predetermined interval, such as 10, 30, 60, 90 degrees, or as performed by the surgeon). The sequence may be repeated with a pre-stress test to better appreciate the knee mechanics, for example, after correction for a lax medial collateral ligament (MCL) or lateral collateral ligament (LCL). In an example, the sequence may be repeated after the femoral cuts have been made or after the femoral trial is seated to provide an opportunity for further improvements to the trial or to optimize soft tissue balancing.

In an example, when a knee requires soft tissue releases, the releases may performed in a staged and sequential fashion and a re-assessment of the improved kinematics may be performed, for example, after each intervention. This process allows a quantification of knee kinematics during different measurement points intraoperatively. The quantifications may be used to balance the soft tissue more accurately than previous techniques. The quantifications may be saved to a database, such as for modeling, machine learning to predict outcomes in future cases, or the like. In an example, an indication may be provided to a surgeon regarding useful releases for a particular patient. In another example, an indication of femoral component sizing AP, location AP, or rotation may be provided to improve flexion/extension gaps throughout the range 0 to 90 degrees, which may include accounting for a location of the patella by using the patella tracking.

In an example, a robotic arm may be used to assess bone quality. Using the assessed bone quality, a system may determine whether to use bone cement or to stem a patient when placing an implant, such as the tibial baseplate 2402. In another example, the tibial baseplate 2402 may be hydraulically powered. The hydraulic power may be used to cause the tibia or femur to rotate to a tension rotation angle automatically. The angle may be recorded, such as by using sensors within the tibial baseplate 2402. The tibial baseplate 2402 may be used to expand the gap between the tibia and the femur.

FIGS. 25A-25B illustrate a patella sensor 2504 of a range of motion testing system in accordance with some embodiments. A first view 2500A illustrates a side view of a patella 2502 with the patella sensor 2504, including relative placement of the patella 2502 with respect to a femur 2506 and a tibia 2508. A second view 2500B illustrates a back view of the patella 2502 with the patella sensor 2504.

In an example, the patella sensor 2504 may be placed on the back of the patella 2502, for example prior to an incision or bone cut. The patella sensor 2504 may be used to determine patella position during a range of motion test. For example, the patella sensor 2504 may include an accelerometer, a magnetometer, a gyroscope, an RFID chip, an optical tracking sensor, or other location sensor. In an example, the patella sensor 2504 may be located around the periphery of the patella 2502, for example to detect and output the outline of the patella 2502. In another example, a size of the patella 2502 may be measured (e.g., via preoperative or intraoperative imaging or direct measurement), and a position of the patella sensor 2504 relative to the patella 2502 may be known, allowing a location of the entirety of the patella 2502 to be known.

The location of the patella 2502 may be used during a surgical procedure, such as a knee replacement. During a knee replacement procedure, a robotic arm may be used to perform aspects of the procedure. The robotic arm may use the detected location of the patella 2502 (from the patella sensor 2504) to perform a patella cut or to avoid the patella while making other cuts. In an example, the patella sensor 2504 may be a passive sensor. In an example, a tracking assembly may be used, such as that described in U.S. Pat. No. 8,571,637 to Biomet Manufacturing, LLC, which is herein incorporated by references in its entirety.

Figure 26A:
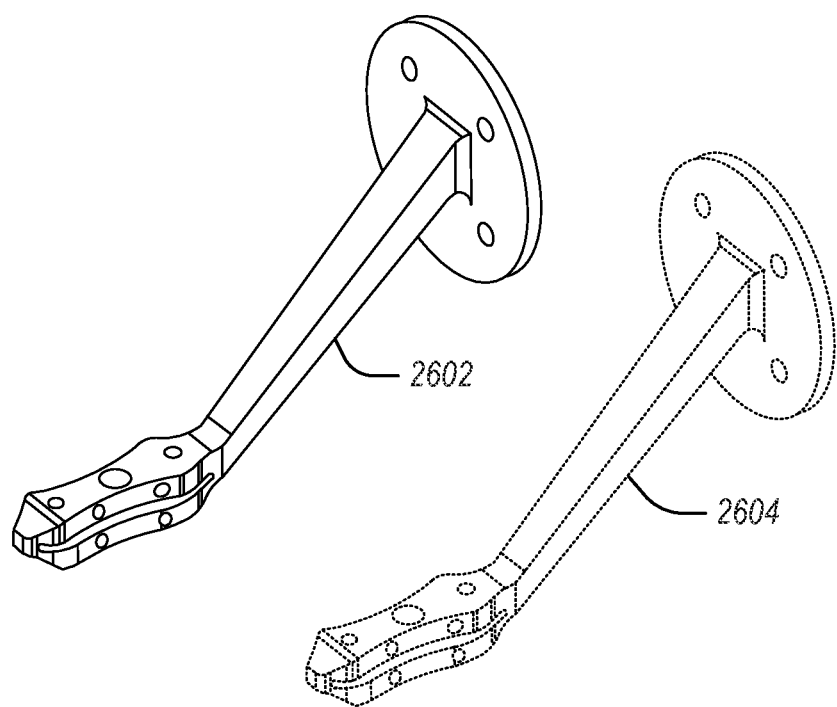
FIGS. 26A-26B illustrate augmented reality systems for control of a robotic arm in accordance with some embodiments.
Figure 26B:
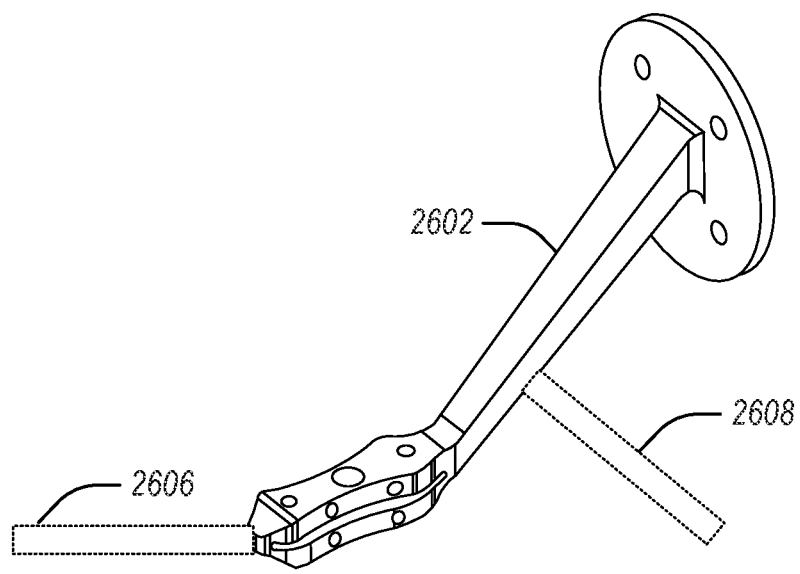

FIGS. 26A-26B illustrate augmented reality systems for control of a robotic arm 2602 in accordance with some embodiments. FIGS. 26A-26B include two example embodiments. The augmented reality systems use virtual components to control real world objects. An augmented reality (AR) device allows a user to view displayed virtual objects that appear to be projected into a real environment, which is also visible. AR devices typically include two display lenses or screens, including one for each eye of a user. Light is permitted to pass through the two display lenses such that aspects of the real environment are visible while also projecting light to make virtual elements visible to the user of the AR device.

Augmented reality is a technology for displaying virtual or "augmented" objects or visual effects overlaid on a real environment. The real environment may include a room or specific area (e.g., a surgical field), or may be more general to include the world at large. The virtual aspects overlaid on the real environment may be represented as anchored or in a set position relative to one or more aspects of the real environment. For example, a virtual robotic arm 2604 of FIG. 26A may be displayed in a set location of a surgical field, to be controlled by a surgeon using an AR device. An AR system may present virtual aspects that are fixed to a real object without regard to a perspective of a viewer or viewers of the AR system (e.g., the surgeon 102). For example, the virtual object 2604 of FIG. 26A may be configured to appear to be an offset distance away from the robotic arm 2602. In an example, virtual objects may appear to have a degree of transparency or may be opaque (i.e., blocking aspects of the real environment).

A surgeon may control the virtual robotic arm 2604 by interacting with the virtual robotic arm 2604 (e.g., using a hand to "interact" with the virtual robotic arm 2604 or a gesture recognized by a camera of the AR device). The virtual robotic arm 2604 may then be used to control the robotic arm 2602. For example, the surgeon may move the virtual robotic arm 2604 and the robotic arm 2602 may move correspondingly.

In the example shown in FIG. 26B, one or more virtual control arms (e.g., 2606 or 2608) may be used to control movement of the robotic arm 2602. For example, a surgeon may move the virtual control arm 2608 to cause the robotic arm 2602 to move in a corresponding fashion. Using more than one virtual control arm may allow for independent degrees of freedom in controlling the robotic arm 2602. For example, a surgeon may rotate his or her hand to virtually "twist" the virtual control arm 2606, which may cause an end effector of the robotic arm 2602 to rotate, without translating the robotic arm 2602. Similarly, the virtual control arm 2608 may be moved to cause the robotic arm 2602 to translate without rotating.

In an example, aspects of the robotic arm 2602 may be controlled by pressing one or more virtual buttons that may appear virtually overlaid in a real environment. For example, a button may be displayed virtually to cause the robotic arm 2602 to move to a first position to aid in performing or to perform a surgical technique. Using the virtual button allows the surgeon to remain in place without needing to turn or avert his or her vision to a display device. This allows the surgeon to maintain focus on the surgical field and monitor the robot, as well as reducing time for the procedure.

In an example, using virtual control elements (e.g., 2604, 2606, or 2608) to control the robotic arm 2602 to perform a procedure may avoid the use of force sensing. For example, instead of controlling the robotic arm 2602 using force sensing when a surgeon moved the robotic arm 2602, the robotic arm 2602 may respond to movements of the virtual control elements. In another example, force sensing may be used in addition to the augmented reality elements described above. For example, force sensing may be used to communicate information to a system using the robotic arm. For example, tapping on the robotic arm 2602 may cause the robotic arm 2602 to lock in place, confirm actions, deny actions, etc. In another example, information may be communicated using virtual buttons as described above. Using the virtual control elements may allow the robotic arm 2602 to be driven in an active mode throughout a procedure, instead of having non-active modes or locations where the active mode is disabled.

Figure 27:
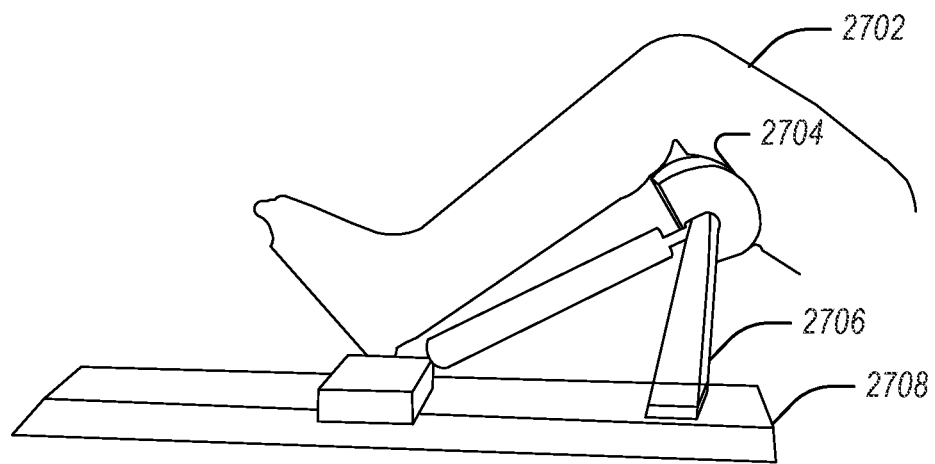
FIG. 27 illustrates a system for distracting a femur from a tibia in accordance with some embodiments.

FIG. 27 illustrates a system 2700 for distracting a femur from a tibia in accordance with some embodiments. The system includes a leg holder 2704 connected to a support structure 2708 via a support device 2706, the leg holder 2704 supporting a patient's knee 2702. The support device 2706 may include a force applicator, such as a hydraulic device, motor, etc., to apply pressure under the femur, for example while the leg is under extension. In another example, the support device 2706 may be connected to a robotic arm, which may be used to apply a force.

Figure 28:
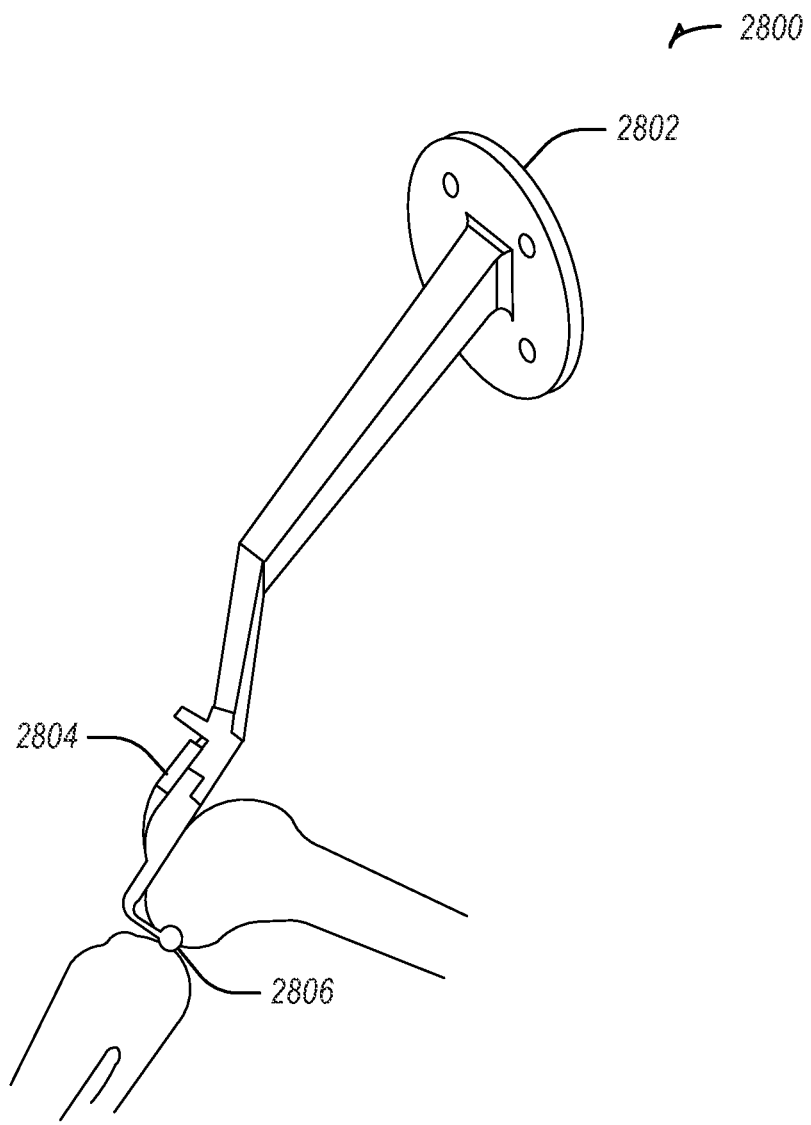
FIG. 28 illustrates a robotic arm registration system in accordance with some embodiments.

FIG. 28 illustrates a robotic arm registration system 2800 in accordance with some embodiments. The robotic arm registration system 2800 includes a robotic arm 2802, an end effector 2804 attached to a distal end of the robotic arm 2802, and a landmark registration identifier 2806 attached to the end effector 2804. The landmark registration identifier 2806 may be used to automatically identify landmarks by using the robotic arm 2802 to navigate to different points of a patient's anatomy. For example, the robotic arm 2802 may be connected to a system that may track the robotic arm 2802 or the patient's anatomy. Using tracking data, the robotic arm 2802 may navigate the patient's anatomy to automatically find and tag points using the landmark registration identifier 2806. In an example, the landmark registration identifier 2806 may include a claw tool to register landmarks at angles that may otherwise be difficult to reach with a straight tool.

Figure 29:
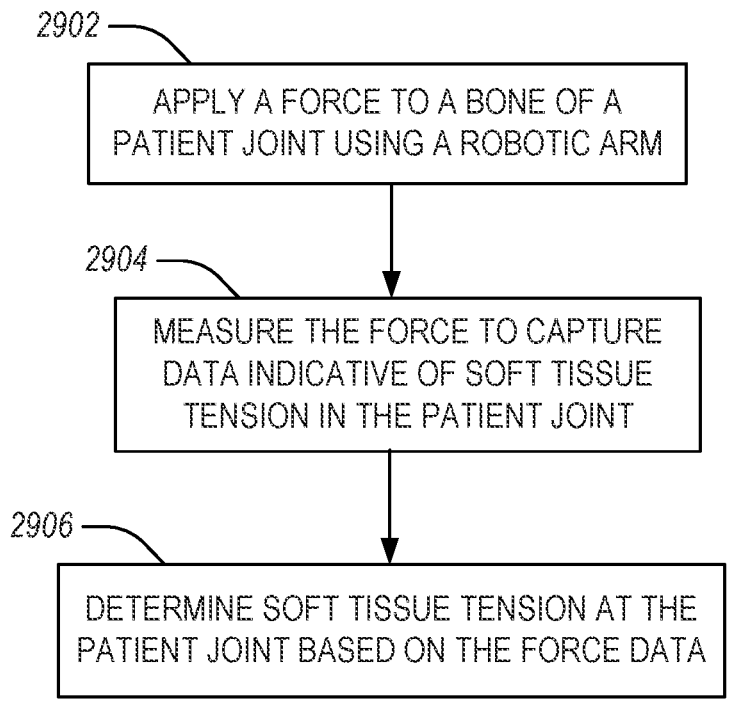
FIG. 29 illustrates a flow chart showing a technique for using a robotic arm to perform soft tissue balancing in accordance with some embodiments.

FIG. 29 illustrates a flow chart showing a technique 2900 for using a robotic arm to perform soft tissue balancing in accordance with some embodiments. The technique 2900 includes an operation 2902 to apply a force to a bone of a patient joint using a robotic arm. The technique 2900 includes an operation 2904 to measure the force to capture data indicative of soft tissue tension in the patient joint. The technique 2900 may include an operation to track, using a processor, movement of the robotic arm, which may include capturing tracking data. The technique 2900 includes an operation 2906 to determine soft tissue tension at the patient joint based on the force data. The soft tissue tension may be determined using the tracking data. The technique 2900 may include an operation to output the soft tissue tension. The technique 2900 may include receiving patella location information from a sensor affixed to a back side of the patella. The technique 2900 may include outputting the patella location information during a range of motion test. The technique 2900 may include controlling the robotic arm using a virtual component displayed using an augmented reality device. In an example, tracking aspects of the patient's anatomy may be performed using a pneumatic cuff sensor on the patient's anatomy. In an example, the bone may be a tibia or a femur.

Figure 30:
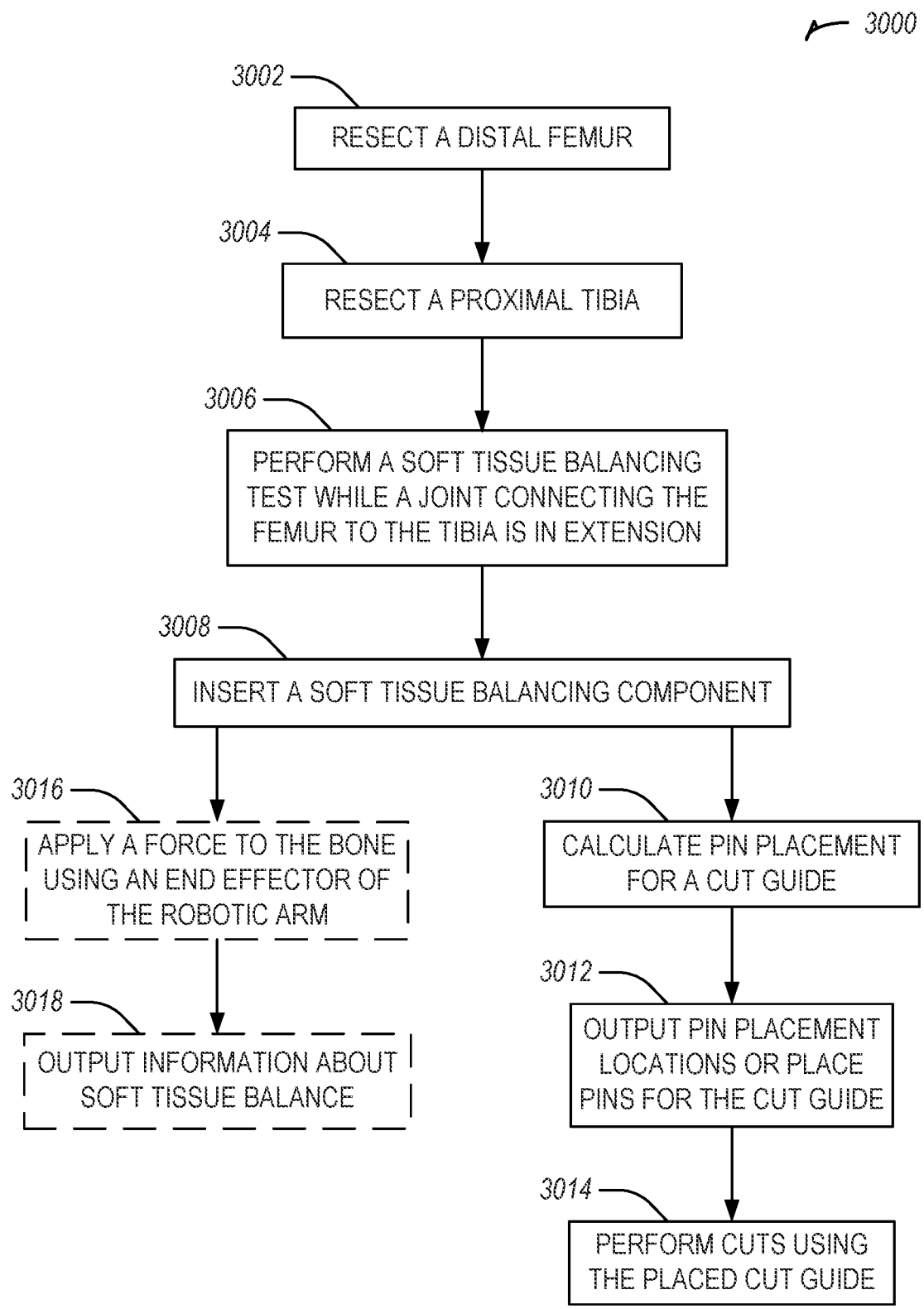
FIG. 30 illustrates a flow chart showing a technique for using a robotic arm to perform a soft tissue pull test in accordance with some embodiments.

FIG. 30 illustrates a flow chart showing a technique 3000 for using a robotic arm to perform a soft tissue pull test in accordance with some embodiments. In an example, the technique 3000 includes an operation 3002 to resect a distal femur and an operation 3004 to resect a proximal tibia. In an example, the technique 3000 includes an operation 3006 to perform a soft tissue balancing test, such as a ligament test while a joint connecting the femur to the tibia is in extension. Operation 3006 may be performed with spacer component or a shim device to put the joint under tension. After operation 3006, the technique 3000 may include performing a release, such as of a ligament or a tendon. The technique 3000 includes an operation 3008 to insert a soft tissue balancing component, such as a spike, condyle pivot, j-shaped adapter, or the like. Once inserted, the soft tissue balancing component may be used to perform a pull test, such as when the joint is in flexion to determine a rotation required to balance ligaments in the joint.

The technique 3000 includes an operation 3010 to use the determined rotation to calculate pin placement for a cut guide (e.g., a 4-in-1 cut guide) to obtain a desired or predetermined femoral component rotation. Operation 3010 may be performed by a processor, such as using surgical procedure planning software to provide instructions to the processor. The technique 3000 includes an operation 3012 to output pin placement locations or to place pins for the cut guide. The technique 3000 includes an operation 3014 to perform cuts using the placed cut guide. In an example, a tibial cut may be performed, optionally after operation 3014 or before operation 3002. In an example, any one or more of operations 3002, 3004, 3006, 3008, 3012, 3014, or the tibial cut may be performed using a robotic arm. In another example, the technique 3000 may include an operation to output a pin placement using the rotation angle for updating a preoperative plan intraoperatively. The output pin placement be used instead of preoperative pin placement locations, or an average or weighted average may be used.

In an example, the technique 3000 may include an optional operation 3016 to apply a force to a bone, such as the femur or the tibia, to perform a soft tissue balancing test, using an end effector of a robotic arm, which may apply a force to the soft tissue balancing component. In an example, the technique 3000 may include an optional operation 3016 to output information about soft tissue balance. In another example, the technique 3000 may include applying a force to the femur or the tibia using the soft tissue balancing component without the use of a robotic arm.

Figure 31:
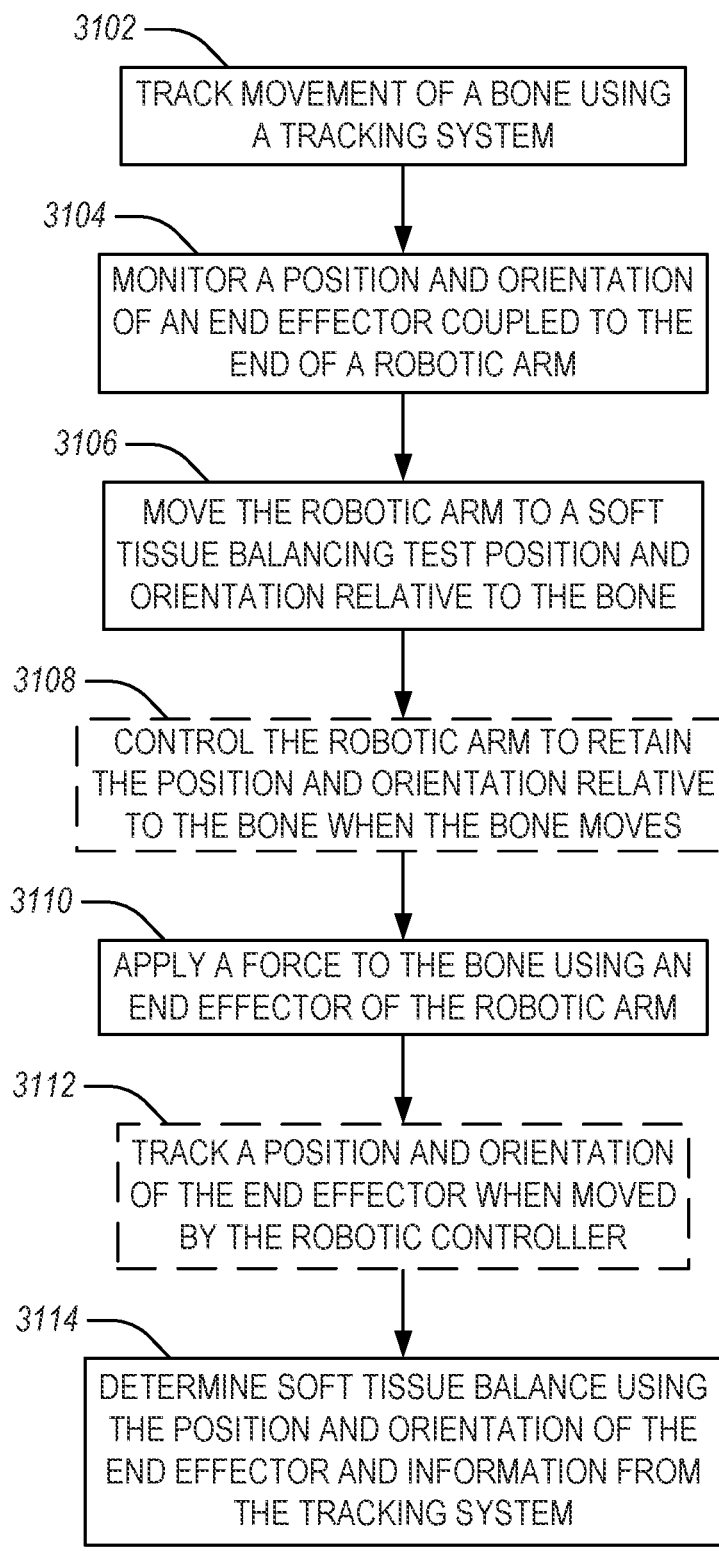
FIG. 31 illustrates a flow chart showing a technique for performing robot-aided surgery using tracking in accordance with some embodiments.

FIG. 31 illustrates a flow chart showing a technique 3100 for performing robot-aided surgery using tracking in accordance with some embodiments. The technique 3100 includes an operation 3102 to track movement of a bone using a tracking system, such as an optical tracking system. The tracking system may include a first tracker affixed to a bone of a patient. In an example, the tracking system includes a second tracker affixed to a second bone of the patient. In an example, the tracking system includes a third tracker affixed to a robotic arm. The technique 3100 may include receiving tracking information from the tracking system including position or orientation information for the third tracker affixed to a portion of the robotic arm. The tracking position or orientation of the robotic arm may be used to track an end effector located at a distal end of the robotic arm, at least in part, using the position and orientation information from the second tracker.

The technique 3100 includes an operation 3104 to monitor a position and orientation of an end effector coupled to the end of a robotic arm, for example using a robotic controller. The technique 3100 includes an operation 3106 to move the robotic arm to a soft tissue balancing test position and orientation relative to the bone. The technique 3100 includes an optional operation 3108 to control the robotic arm to retain the position and orientation relative to the bone when the bone moves, for example using the robotic controller. The optional operation 3108 may include receiving an indication of movement of the bone from the tracking system. The technique 3100 includes an operation 3110 to apply a force to the bone using an end effector of the robotic arm. The technique 3100 includes an optional operation 3112 to track a position and orientation of the end effector when moved by the robotic controller.

The technique 3100 includes an operation 3114 to determine soft tissue balance using the position and orientation of the end effector or information from the tracking system, such as a position of the first tracker affixed to the bone. In an example, determining the soft tissue balance may include using force information from a force sensor coupled between the end effector and the robotic arm. The technique 3100 may include an operation to identify manual movement of the end effector using a force sensor and allowing the manual movement of the end effector relative to the bone. In an example, the end effector may be coupled to a distal end of a bone spike after the bone spike is coupled to the bone. The technique 3100 may include an operation to output the soft tissue balance, such as for display on a user interface.

The technique 3100 may include an operation to release the force on the bone when the soft tissue balancing test indicates that soft tissue connected to the bone is in balance, when a threshold force is reached, when a threshold tension is reached, when a predetermined distance (e.g., a distance equal to a tibial implant thickness), or the like. Releasing the force on the bone may include returning the force to zero, such as by increments. For example, the soft tissue balancing test indicates that the soft tissue connected to the bone is in balance based on detecting the bone in a pre-determined orientation during the test. In another example, the soft tissue balancing test indicates that soft tissue connected to the bone is in balance when sufficient data is collected to determine a balance in the soft tissue, and wherein the balance is an indication of the difference in tension between a medial side and a lateral side of the joint. The balance may indicate an angle for a resection cut to be made in a joint replacement procedure. The technique 3100 may include an operation to perform a release of a portion of soft tissue connected to the bone based on the soft tissue balance. The technique 3100 may include an operation to output, for example for display on a user interface, an indication of soft tissue balance or an angle of rotation of the bone relative to a second bone.

The technique 3100 may include an operation to calculate a target femoral implant rotation using a determined rotation of the femur during a soft tissue balancing test. For example, the determined rotation used may be when the gap balance is equal to a predetermined gap distance. The target femoral implant may be the inverse or opposite of the determined rotation. In an example, the technique 3100 may include an operation to store the target femoral implant rotation, such as in memory or a database, for use by planning software.

Figure 32:
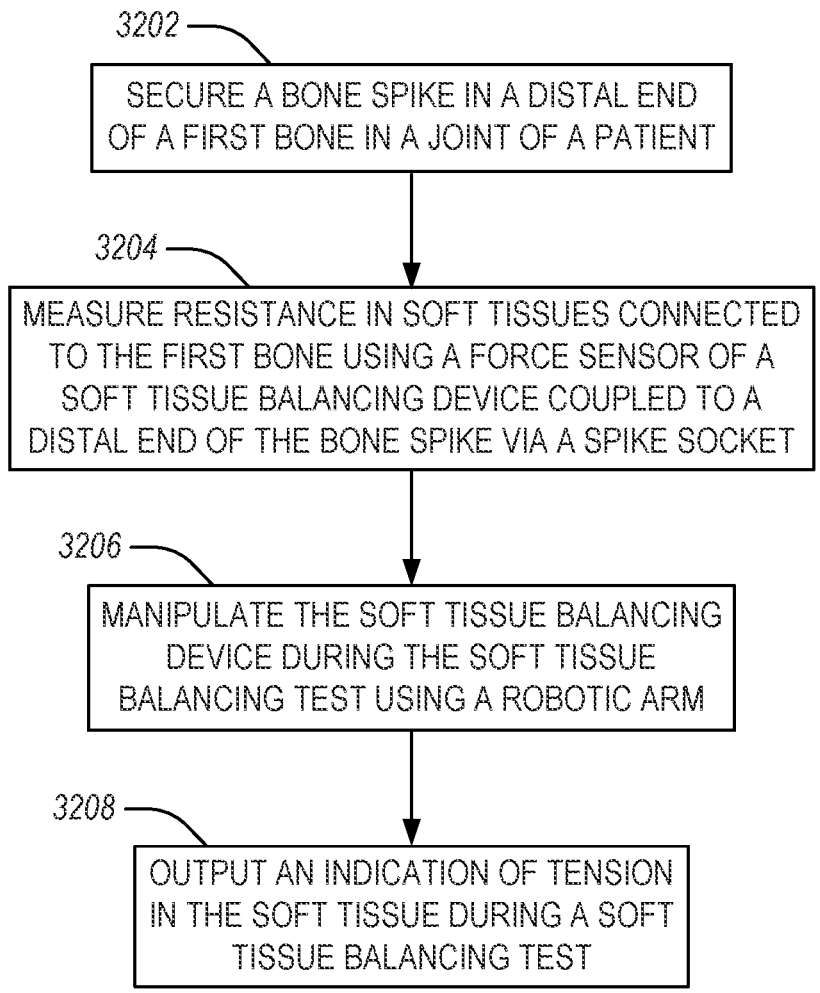
FIG. 32 illustrates a flow chart showing a technique for performing robot-aided surgery using a force sensor in accordance with some embodiments.

FIG. 32 illustrates a flow chart showing a technique 3200 for performing robot-aided surgery using a force sensor in accordance with some embodiments. The technique 3200 includes an operation 3202 to secure a bone spike in a distal end of a first bone in a joint of a patient. The technique 3200 includes an operation 3204 to measure resistance in soft tissues connected to the first bone using a force sensor of a soft tissue balancing device coupled to a distal end of the bone spike via a spike socket.

The technique 3200 includes an operation 3206 to manipulate the soft tissue balancing device during the soft tissue balancing test using a robotic arm. The operation 3206 may include applying tension to the joint using the robotic arm through the soft tissue balancing device during the soft tissue balancing test. The technique 3200 includes an operation 3208 to output an indication of tension in the soft tissue during a soft tissue balancing test. In an example, the first bone is a femur, and the soft tissue includes ligaments connecting the femur to a tibia of the patient joint. The technique 3200 may include using the robotic arm is to manipulate the soft tissue balancing device with the femur and the tibia in flexion or extension.

The technique 3200 may include an operation to output, from the robotic arm, a resection angle for an at least partial joint replacement to a computing device to calculate soft tissue balance in the joint. The computing device may be used to calculate a pin placement location for a cut guide based on the resection angle. In an example, a pin placement trial or pins may be positioned or placed, for example using the robotic arm, at a location on the first bone according to the pin placement location. The technique 3200 may include an operation to output, from a force sensor, force data indicative of soft tissue tension in the patient joint when the force is applied to the first bone by the soft tissue balancing component. In an example, soft tissue tension may be determined at the patient joint based on the force data.

The technique 3200 may include an operation to move the robotic arm to a soft tissue balancing test position and orientation relative to the first bone. In an example, the robotic arm may be controlled to retain the position and orientation relative to the first bone when the bone moves. The operation may include applying a force to the first bone using the soft tissue balancing component. The operation may include tracking movement of the first bone using an optical tracking system including a first optical tracker affixed to the first bone of the patient and a second optical tracker affixed to the robotic arm. The operation may include determining the tension in the soft tissue during a soft tissue balancing test using the tracked movement of the first bone. The operation may include tracking a position and orientation of the soft tissue balancing component when moved, and determining soft tissue tension using the position and orientation of the end effector and information from the optical tracking system including a position of the second optical tracker affixed to the robotic arm and a position of the first optical tracker affixed to the first bone. In an example, the operation may include determining a tension in medial soft tissue and a tension in lateral soft tissue using a force vector of the soft tissue balancing component on the first bone provided by the force sensor and a relative bone orientation of the first bone to a second bone provided by the optical tracking system.

FIGS. 33A-33D illustrate example user interfaces 3300A-3300D for joint replacement surgical planning in accordance with some embodiments. User interface 3300A of FIG. 33A includes a cut checklist 3302 to illustrate cuts that have been performed or that are not yet completed. User interface 3300A includes an interactive user guide 3304 showing a soft tissue balancing test overview. The user guide 3304 shows a target implant rotation with respect to a femur to give a balanced flexion gap. The user guide 3304 shows four steps of the soft tissue balancing test, from an initial state, to pulling on the femur, to showing a gap imbalance, to finally showing a rotation to align the soft tissue.

Figure 33A:
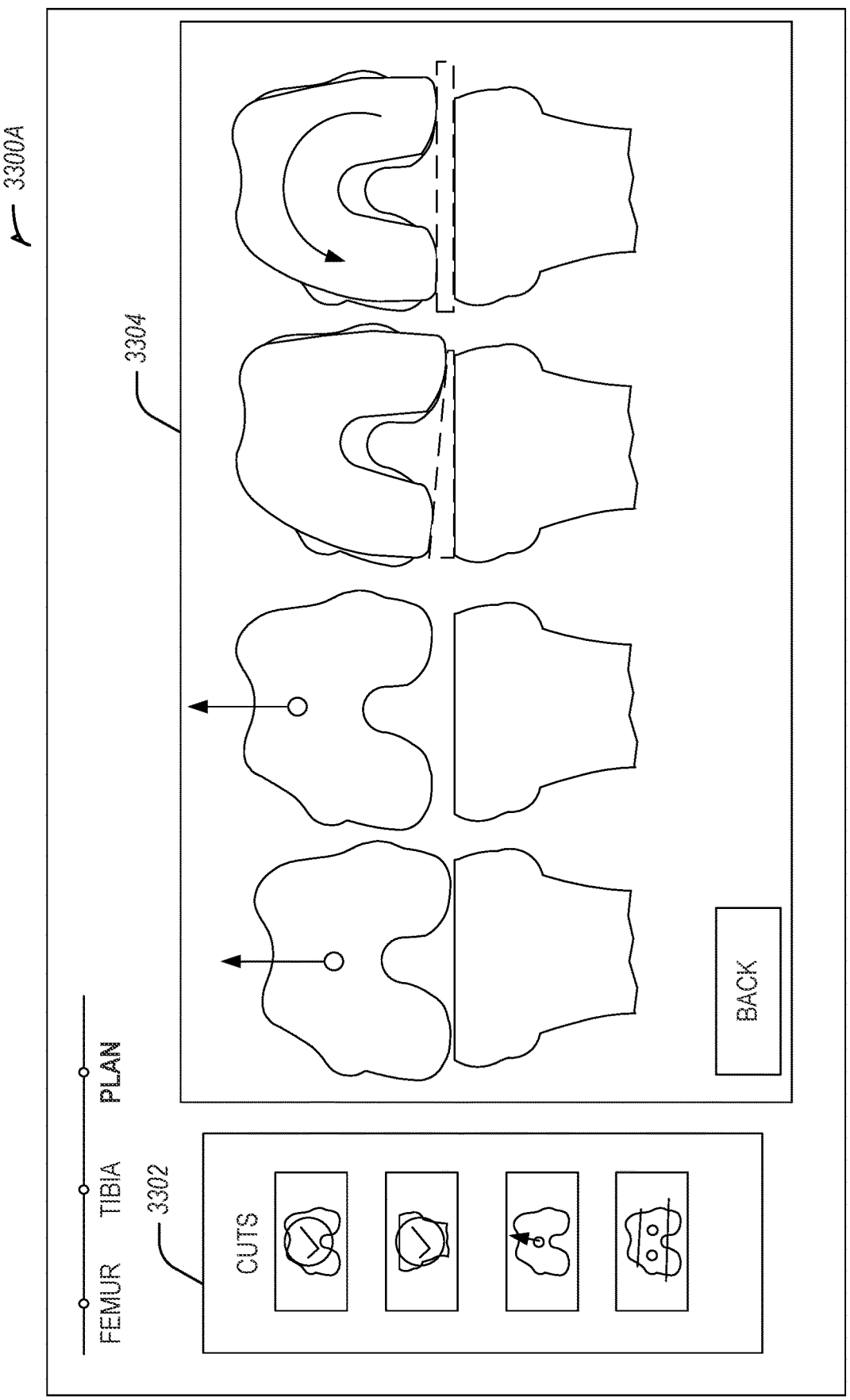
FIGS. 33A-33D illustrate example user interfaces for joint replacement surgical planning in accordance with some embodiments.
Figure 33B:
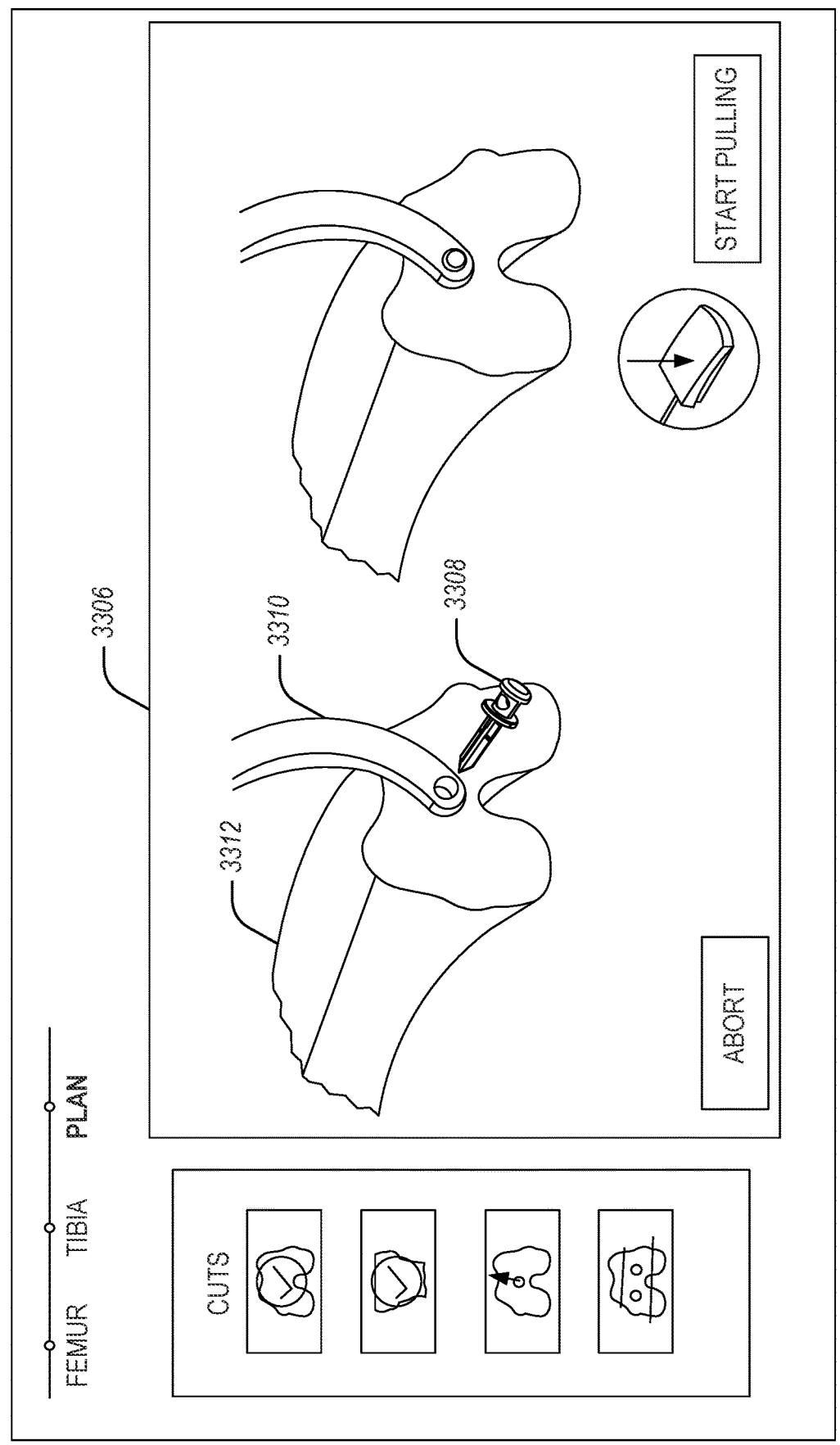

User interface 3300B of FIG. 33B includes a second user guide 3306 including instructions on how to insert a spike 3308 to connect a soft tissue balancing component 3310 to a femur 3312. The spike 3308 holds the soft tissue balancing component 3310 in place, but may allow the femur 3312 to rotate. The soft tissue balancing test may be initiated, for example, by pressing a foot pedal, which is indicated in the second user guide 3306. In an example, the soft tissue balancing test may be performed with a patella or soft tissue in place by using a j-shaped or hook-shaped soft tissue balancing component 3310. When the soft tissue balancing test is initiated, a robotic arm may pull the soft tissue balancing component 3310, such as by using an end effector connecting the robotic arm to the soft tissue balancing component 3310 to apply a force on the spike 3308, which may in turn cause a force on the femur 3312, for example to move the femur 3312 away from a tibia.

Figure 33C:
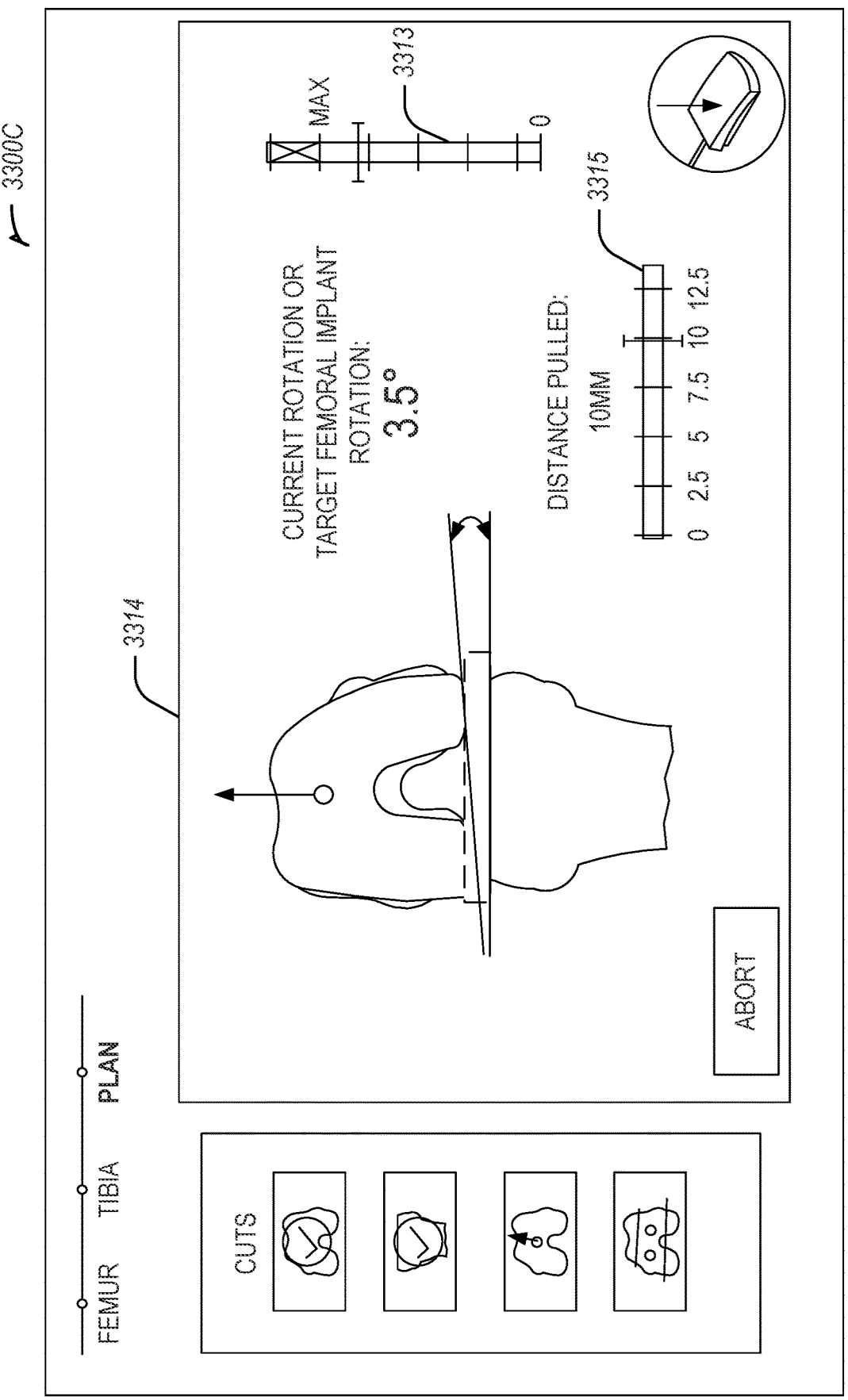

User interface 3300C of FIG. 33C includes a third user guide 3314 which shows an illustration of a patient joint including a current imbalance at a particular gap distance, while superimposing a proposed balance (e.g., based on completed releases, cuts, and implants added to the joint). The third user guide 3314 includes information related to a current rotation or a target femoral implant rotation (e.g., the rotation information may change over time or during a procedure, such as from a current rotation to a target rotation, or may show both, or a difference). The distance pulled (e.g., over time or at a current time) is also illustrated in the third user guide 3314. The third user guide 3314 may include user-selectable options to apply a target femoral implant rotation to a 3D plan or to not apply the target femoral implant rotation to the 3D plan. The 3D plan may include preoperative or intraoperative plans. Adding the target femoral implant rotation to the 3D plan may include adding it to the 3D plan as is, or with changes (e.g., surgeon adjustments).

The user guide 3314 may include a force bar 3313 or a distance bar 3315. The force bar 3313 may be used to display a current pulling force (e.g., of a robotic arm on the femur). In an example, the robotic arm may be stopped automatically by a robotic controller when the force reaches a maximum force, which may be displayed on the force bar 3313. In an example, a surgeon may control the robotic arm by adjusting the force bar 3313. The distance bar 3315 may move simultaneously with the force bar 3313 in an example. The distance bar 3315 shows a distance pulled, such as a distance from the femur to the tibia (whether the femur or the tibia is pulled). In an example, the distance bar 3315 may be controlled by a surgeon to move the robotic arm similar. In an example, the distance bar 3315 may include a maximum distance pulled, which when the femur and the tibia are separated by the maximum distance, the robotic arm may be stopped.

Figure 33D:
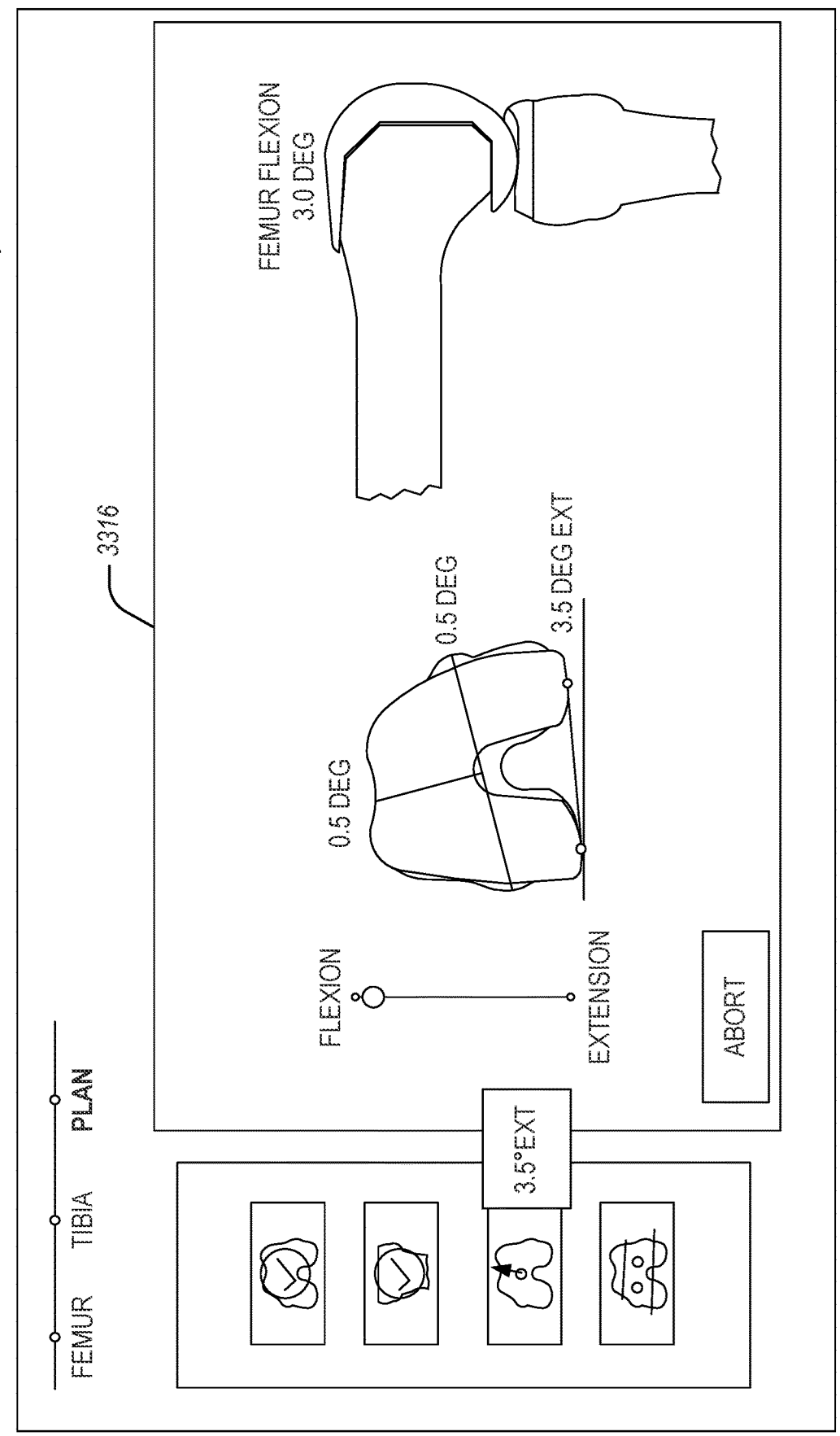

User interface 3300D of FIG. 33D includes a fourth user guide 3316, which shows rotation of a femur in a knee joint in various views. The femur may be viewed in flexion with respect to a tibia or in extension. When used intraoperatively, as the joint is placed in these different orientations, the user guide 3316 may be automatically updated (e.g., using trackers).

One or more of user guides 3304, 3306, 3314, or 3316 may include information on ligament balance. For example, a soft tissue balancing test may be performed, and force information, tension information, or other sensor data may be sent to the one or more of user guides 3304, 3306, 3314, or 3316 to display soft tissue balance, such as a rotation angle to balance the ligaments. In another example, the one or more of user guides 3304, 3306, 3314, or 3316 may display a measured resection technique, for example by providing feedback on actual measured angles or detected forces after or before resection, in addition to the rotation angle at which there is balance.

In an example, medial and lateral borders of a tibial tubercle may be identified and used to determine a medial third landmark location. The one or more of user guides 3304, 3306, 3314, or 3316 may display the medial and lateral borders or the medial third landmark location. For example, a robotic arm may be used to identify a most medial boundary of a tibial tuberosity. The robotic arm may be used to identify a most lateral boundary of the tibia tuberosity. A system may use these identified boundaries to accurately display and locate a location known as a medial third location on the tibial tuberosity. Identifying this location may not be reproducibly performed with conventional instrumentation, such as with sub-millimeter metric precision. This location may be used to assist in a rotational placement of a tibial base plate for a knee arthroplasty as a reference point.

VARIOUS NOTES & EXAMPLES

Each of these non-limiting examples may stand on its own, or may be combined in various permutations or combinations with one or more of the other examples.

Example 1 is a robot-aided surgical system comprising: a tracking system including a first tracker affixed to a bone of a patient, the tracking system configured to track movement of the bone; a robotic controller to; monitor a position and orientation of an end effector coupled to an end of a robotic arm; apply a force to the bone using the end effector; determine soft tissue balance using information from the tracking system including a position of the first tracker affixed to the bone; and output the soft tissue balance.

In Example 2, the subject matter of Example 1 optionally includes a soft tissue balancing component coupled to the end effector and configured to transfer force from the end effector to the bone.

In Example 3, the subject matter of Example 2 optionally includes wherein the soft tissue balancing component comprises at least one of a spike, a condyle pivot, a jig, or an adaptor, wherein the adaptor is shaped to avoid a patella or soft tissue of a knee joint of the patient.

In Example 4, the subject matter of Example 3 optionally includes wherein the soft tissue balancing component comprises the condyle pivot, and wherein the condyle pivot comprises a plurality of platform arms each capable of applying an individually determined force to the bone.

In Example 5, the subject matter of any one or more of Examples 3-4 optionally include wherein the soft tissue balancing component comprises the jig, and wherein the jig includes at least one of a spacer block or a flat attachment.

In Example 6, the subject matter of any one or more of Examples 1-5 optionally include a force sensor coupled to the robotic arm, and wherein to determine the soft tissue balance, the robotic controller is to use force information from the force sensor.

In Example 7, the subject matter of Example 6 optionally includes wherein the robotic controller is to determine the force information when a pull test performed by the robotic arm reaches a predetermined gap distance from the bone to a second bone, the force information indicative of an equal force between two ligaments connecting the bone to the second bone.

In Example 8, the subject matter of any one or more of Examples 1-7 optionally include wherein to output the soft tissue balance, the robotic controller is to output an indication of the degree of rotation of the bone.

In Example 9, the subject matter of Example 8 optionally includes wherein the robotic controller is to determine a location to place a cut guide for resecting the bone using the robotic arm based at least in part the indication of the degree of rotation.

In Example 10, the subject matter of any one or more of Examples 1-9 optionally include wherein the determined soft tissue balance indicates a difference in tension between a medial side and a lateral side of a knee joint of the patient.

In Example 11, the subject matter of any one or more of Examples 1-10 optionally include wherein to output the soft tissue balance, the robotic controller is to output an amount of force applied by the end effector on the bone when the bone reaches a predetermined gap thickness in relation to a second bone.

In Example 12, the subject matter of any one or more of Examples 1-11 optionally include a cutting device to perform a release of a portion of soft tissue connected to the bone based on the soft tissue balance.

In Example 13, the subject matter of any one or more of Examples 1-12 optionally include a display device to display an indication of the output soft tissue balance or an angle of rotation of the bone relative to a second bone.

In Example 14, the subject matter of any one or more of Examples 1-13 optionally include wherein the robot controller is further to determine alterations required on the bone to receive at least one implant in a given location, using a model of the at least one implant and the soft tissue balance.

Example 15 is a robot-aided surgical system comprising: a tracking system including a first tracker affixed to a bone of a patient, the tracking system configured to track movement of the bone; a robotic controller to: monitor a position and orientation of an end effector coupled to an end of a robotic arm; apply a force to the bone using a soft tissue balancing component coupled to the end effector, the soft tissue balancing component configured to transfer force from the end effector to the bone; and determine soft tissue balance using information from the tracking system including a position of the first tracker affixed to the bone and force information from a force sensor coupled to the robotic arm; and a display device to display an indication of the soft tissue balance including a tension of at least one ligament connecting the bone to a second bone or an angle of rotation of the bone relative to the second bone.

In Example 16, the subject matter of Example 15 optionally includes wherein the indication of the soft tissue balance includes an indication of a difference in tension between a medial ligament and a lateral ligament of a knee joint of the patient.

In Example 17, the subject matter of any one or more of Examples 15-16 optionally include a cut guide coupled to the robotic arm to guide a resection cut in a joint replacement procedure based on the angle of rotation of the bone relative to the second bone.

In Example 18, the subject matter of any one or more of Examples 15-17 optionally include a cutting device coupled to the robotic arm to perform a release of a portion of soft tissue connected to the bone based on the soft tissue balance.

In Example 19, the subject matter of any one or more of Examples 15-18 optionally include a cut guide coupled to the robotic arm to guide a resection on a tibia of the patient before determining the soft tissue balance.

In Example 20, the subject matter of Example 19 optionally includes wherein the robotic controller is further to determine a pin placement location for a cut guide based at least in part on the angle of rotation of the bone relative to the second bone.

Example 21 is a robot-aided knee arthroplasty system comprising: a leg holder to affix anatomy of a patient during an arthroplasty procedure; an end effector of a robotic arm to couple to a femur of the knee joint with a soft tissue balancing component that permits the femur to freely rotate while coupled to the end effector; a robotic controller to: cause the robotic arm to apply a pulling force to the femur to increase a gap distance between the femur and a tibia of the knee joint; measure the gap distance between the femur and the tibia and a rotation of the femur; and store, when the gap balance is equal to a predetermined gap distance, the rotation of the femur as a target femoral implant rotation; and a surgical planning system to plan a position and orientation of a resection such that inserting a femoral implant on the femur causes the femur to achieve the target femoral implant rotation.

In Example 22, the subject matter of Example 21 optionally includes a cut guide coupled to the robotic arm to guide a cutting device to perform the resection.

In Example 23, the subject matter of Example 22 optionally includes wherein the robotic controller is to: determine a pin hole location on the bone based at least in part on the indication of the degree of rotation, the pin hole location determined such that a pin inserted into the pin hole location aligns the cut guide to the bone; cause the robotic arm to place a pin guide component, coupled to the end effector of the robotic arm, on the bone such that a drill hole of the pin guide component aligns with the pin hole location.

In Example 24, the subject matter of any one or more of Examples 21-23 optionally include a tracking system to track trackers affixed to the femur and the tibia and to output tracking information, and wherein to measure the gap distance between the femur and tibia and the rotation of the femur, the robotic controller is to use the tracking information.

In Example 25, the subject matter of any one or more of Examples 21-24 optionally include wherein the robotic controller is further to cause the robotic arm to apply a pushing force to the tibia and calculate a tension in a lateral collateral ligament and a medial collateral ligament of the knee joint as the pushing force is applied to the tibia with the robotic arm, and further comprising a display device to display an indication of the tension in the lateral collateral ligament and the medial collateral ligament.

Example 26 is at least one machine-readable medium including instructions for performing robot-aided surgery, which when executed by a processor, cause the processor to: cause a robotic arm to apply a pulling force to a femur, using a soft tissue balancing component coupled to the femur such that the femur freely rotates, to increase a gap distance between the femur and a tibia of the knee joint; measure the gap distance between the femur and a tibia and a rotation of the femur; and calculate a target femoral implant rotation using the rotation of the femur, when the gap balance is equal to a predetermined gap distance; store the target femoral implant rotation; and plan, using a surgical planning system, a position and orientation of a resection such that inserting a femoral implant on the femur causes the femur to achieve the target femoral implant rotation.

In Example 27, the subject matter of Example 26 optionally includes instructions to: track trackers affixed to the femur and the tibia; output tracking information; and use the tracking information to measure the gap distance between the femur and tibia and the rotation of the femur.

In Example 28, the subject matter of any one or more of Examples 26-27 optionally include instructions to: cause the robotic arm to apply a pushing force to the tibia; calculate a tension in lateral and medial compartments (e.g., a lateral collateral ligament and a medial collateral ligament) of the knee joint as the pushing force is applied to the tibia with the robotic arm; and output an indication of the tension in the lateral and medial compartments.

In Example 29, the subject matter of any one or more of Examples 26-28 optionally include instructions to determine a pin placement location for a cut guide based at least in part on the rotation of the femur.

In Example 30, the subject matter of Example 29 optionally includes instructions to cause the robotic arm to position a pin placement trial for placing a pin at a location on the bone according to the pin placement location.

Example 31 is a robot-aided surgical system comprising: a bone spike adapted to be secured in a distal end of a first bone in a joint of a patient; a soft tissue balancing device comprising a force sensor and a spike socket coupable to a distal end of the bone spike, the force sensor adapted to measure resistance in soft tissues connected to the first bone; a robotic arm to manipulate the soft tissue balancing device during the soft tissue balancing test; and an output device to output an indication of tension in the soft tissue during a soft tissue balancing test.

In Example 32, the subject matter of Example 31 optionally includes wherein the soft tissue balancing device is an end effector on the robotic arm or a j-shaped arm coupleable to the bone spike.

In Example 33, the subject matter of any one or more of Examples 31-32 optionally include wherein the robotic arm applies tension to the joint through the soft tissue balancing device during the soft tissue balancing test.

In Example 34, the subject matter of any one or more of Examples 31-33 optionally include wherein the robotic arm and soft tissue balancing device provide output to a computing device to calculate soft tissue balance in the joint.

In Example 35, the subject matter of Example 34 optionally includes wherein the soft tissue balance is output in a medial tension and a lateral tension.

In Example 36, the subject matter of any one or more of Examples 34-35 optionally include wherein the soft tissue balance is output as a resection angle for an at least partial joint replacement.

In Example 37, the subject matter of Example 36 optionally includes wherein the resection angle is selected to balance the soft tissue after at least a portion of the joint is replaced with a prosthesis.

In Example 38, the subject matter of any one or more of Examples 36-37 optionally include wherein the computing device is to calculate a pin placement location for a cut guide based on the resection angle.

In Example 39, the subject matter of Example 38 optionally includes wherein the robotic arm is further to position a pin placement trial for placing a pin at a location on the first bone according to the pin placement location.

In Example 40, the subject matter of any one or more of Examples 31-39 optionally include a retention device to restrain a second bone of the joint of the patient during the soft tissue balancing test.

In Example 41, the subject matter of any one or more of Examples 31-40 optionally include a force sensor to output force data indicative of soft tissue tension in the patient joint when the force is applied to the first bone by the soft tissue balancing component.

In Example 42, the subject matter of Example 41 optionally includes a processor to determine soft tissue tension at the patient joint based on the force data.

In Example 43, the subject matter of any one or more of Examples 31-42 optionally include a robotic controller to: move the robotic arm to a soft tissue balancing test position and orientation relative to the first bone; control the robotic arm to retain the position and orientation relative to the first bone when the bone moves; and apply a force to the first bone using the soft tissue balancing component.

In Example 44, the subject matter of Example 43 optionally includes an optical tracking system including a first optical tracker affixed to the first bone of the patient and a second optical tracker affixed to the robotic arm, the optical tracking system to track movement of the first bone, and further comprising a processor to determine the tension in the soft tissue during a soft tissue balancing test using the tracked movement of the first bone.

In Example 45, the subject matter of Example 44 optionally includes wherein the processor is further to: track a position and orientation of the soft tissue balancing component when moved by the robotic controller; and determine soft tissue tension using the position and orientation of the end effector and information from the optical tracking system including a position of the second optical tracker affixed to the robotic arm and a position of the first optical tracker affixed to the first bone.

In Example 46, the subject matter of Example 45 optionally includes wherein the processor is to use a force vector of the soft tissue balancing component on the first bone provided by the force sensor and a relative bone orientation of the first bone to a second bone provided by the optical tracking system to determine a tension in medial soft tissue and a tension in lateral soft tissue.

Example 47 is a method for performing robot-aided surgery comprising: securing a bone spike in a distal end of a first bone in a joint of a patient; measuring resistance in soft tissues connected to the first bone using a force sensor of a soft tissue balancing device coupled to a distal end of the bone spike via a spike socket; manipulating the soft tissue balancing device during the soft tissue balancing test using a robotic arm; and outputting an indication of tension in the soft tissue during a soft tissue balancing test.

In Example 48, the subject matter of Example 47 optionally includes wherein the first bone is a femur, and the soft tissue includes ligaments connecting the femur to a tibia of the patient joint, and further comprising using the robotic arm is to manipulate the soft tissue balancing device with the femur and the tibia in flexion or extension.

In Example 49, the subject matter of any one or more of Examples 47-48 optionally include wherein manipulating the soft tissue balancing device includes applying tension to the joint using the robotic arm through the soft tissue balancing device during the soft tissue balancing test.

In Example 50, the subject matter of any one or more of Examples 47-49 optionally include outputting, from the robotic arm, a resection angle for an at least partial joint replacement to a computing device to calculate soft tissue balance in the joint.

In Example 51, the subject matter of Example 50 optionally includes calculating, using the computing device, a pin placement location for a cut guide based on the resection angle.

In Example 52, the subject matter of Example 51 optionally includes positioning, using the robotic arm, a pin placement trial for placing a pin at a location on the first bone according to the pin placement location.

In Example 53, the subject matter of any one or more of Examples 47-52 optionally include outputting, from a force sensor, force data indicative of soft tissue tension in the patient joint when the force is applied to the first bone by the soft tissue balancing component.

In Example 54, the subject matter of Example 53 optionally includes determining soft tissue tension at the patient joint based on the force data.

In Example 55, the subject matter of any one or more of Examples 47-54 optionally include moving the robotic arm to a soft tissue balancing test position and orientation relative to the first bone; controlling the robotic arm to retain the position and orientation relative to the first bone when the bone moves; and applying a force to the first bone using the soft tissue balancing component.

In Example 56, the subject matter of Example 55 optionally includes tracking movement of the first bone using an optical tracking system including a first optical tracker affixed to the first bone of the patient and a second optical tracker affixed to the robotic arm; and determining the tension in the soft tissue during a soft tissue balancing test using the tracked movement of the first bone.

In Example 57, the subject matter of Example 56 optionally includes tracking a position and orientation of the soft tissue balancing component when moved; and determining soft tissue tension using the position and orientation of the end effector and information from the optical tracking system including a position of the second optical tracker affixed to the robotic arm and a position of the first optical tracker affixed to the first bone.

In Example 58, the subject matter of Example 57 optionally includes determining a tension in medial soft tissue and a tension in lateral soft tissue using a force vector of the soft tissue balancing component on the first bone provided by the force sensor and a relative bone orientation of the first bone to a second bone provided by the optical tracking system.

Example 59 is a robot-aided surgical system comprising: an end effector of a robotic arm configured to apply a force to a tibia of a knee joint of a patient when the robotic arm is in contact with the tibia and moved in a specified direction to perform a soft tissue balancing test; and a display device to output an indication of tension in soft tissue during the soft tissue balancing test.

In Example 60, the subject matter of Example 59 optionally includes a force sensor to output force data indicative of soft tissue tension in the patient joint when the force is applied to the tibia by the robotic arm.

In Example 61, the subject matter of Example 60 optionally includes a processor to determine soft tissue tension at the patient joint based on the force data.

In Example 62, the subject matter of any one or more of Examples 59-61 optionally include an optical tracking system including a first optical tracker affixed to the tibia of the patient, the optical tracking system to track movement of the tibia.

In Example 63, the subject matter of Example 62 optionally includes a robotic controller to: move the end effector of the robotic arm to a soft tissue balancing test position and orientation relative to the tibia; control the robotic arm to retain the position and orientation of the end effector relative to the tibia when the optical tracking system indicates movement of the tibia; and apply a force to the tibia using the robotic arm.

In Example 64, the subject matter of Example 63 optionally includes a processor to: track a position and orientation of the end effector when moved by the robotic controller; and determine soft tissue tension using the position and orientation Af the end effector and information from the optical tracking system including a position of the first optical tracker affixed to the tibia.

In Example 65, the subject matter of any one or more of Examples 63-64 optionally include a second optical tracker affixed to the robotic arm, and wherein the robotic controller is to use a position of the second optical tracker affixed to the robotic arm to determine the position and orientation of the end effector relative to the tibia.

In Example 66, the subject matter of any one or more of Examples 59-65 optionally include a processor to enable a manual movement mode of the robotic arm, the manual movement mode allowing a surgeon to initiate movement of the end effector of the robotic arm, the initiated movement continued by augmented force applied by the robotic arm.

In Example 67, the subject matter of Example 66 optionally includes wherein the initiated movement causes the end effector to be in contact with the tibia.

In Example 68, the subject matter of any one or more of Examples 59-67 optionally include a processor to receive an indication to initiate the soft tissue balancing test, and in response, cause the robotic arm to initiate the soft tissue balancing test.

In Example 69, the subject matter of any one or more of Examples 59-68 optionally include a pin to couple the end effector to the tibia when the end effector is in contact with the tibia.

In Example 70, the subject matter of any one or more of Examples 59-69 optionally include a processor to determine a resection angle on a cut of a femur connected via the soft tissue to the tibia based on the indication of tension in the soft tissue determined during the soft tissue balancing test.

Example 71 is a tibial force detection system comprising: a tibial baseplate including: a plurality of force sensors to detect forces at corresponding locations of the tibial baseplate; and a plurality of actuators corresponding to the plurality of force sensors, the plurality of actuators causing the tibial baseplate to displace a femur from a tibia at respective locations; and a processor to: receive force information related to forces at the corresponding locations from the plurality of force sensors of the tibial baseplate; determine a rotation angle of the femur relative to the tibia based on the force information; and output the rotation angle for display.

In Example 72, the subject matter of Example 71 optionally includes wherein the plurality of force sensors include four force sensors corresponding to four quadrants of the tibial baseplate.

In Example 73, the subject matter of any one or more of Examples 71-72 optionally include wherein the plurality of actuators are configured to be activated independently of each other.

In Example 74, the subject matter of any one or more of Examples 71-73 optionally include wherein the plurality of actuators are activated to apply tension to one or more ligaments connecting the femur to the tibia until the one or more ligaments are in tension before determining the rotation angle.

In Example 75, the subject matter of any one or more of Examples 71-74 optionally include wherein the plurality of actuators include a number of actuators corresponding to a number of force sensors of the plurality of force sensors, and wherein the respective locations cause forces at the corresponding locations of the tibial baseplate.

In Example 76, the subject matter of any one or more of Examples 71-75 optionally include wherein the processor is further to use the rotation angle to determine a resection angle for a cut of the femur.

In Example 77, the subject matter of any one or more of Examples 71-76 optionally include wherein in response to a release cut being performed on soft tissue connecting the femur to the tibia, the plurality of actuators are further to cause the tibial baseplate to further displace the femur from the tibia at respective locations.

In Example 78, the subject matter of any one or more of Examples 71-77 optionally include wherein the plurality of actuators are to cause the tibial baseplate to release the femur from being displaced with respect to the tibia in response to the processor determining that the rotation angle is at a predetermined angle.

Example 79 is a method for performing a soft tissue pull test, the method comprising: performing a soft tissue balancing test, using a robotic arm, while a joint connecting a femur to a tibia is in extension; inserting a soft tissue balancing component attached to a distal end of a robotic arm; performing the soft tissue balancing test using the soft tissue balancing component and the robotic arm while the joint is in flexion to determine a rotation to balance ligaments in the joint; calculating pin placement for a cut guide based on the rotation; and placing the cut guide according to the pin placement using the robotic arm.

In Example 80, the subject matter of Example 79 optionally includes performing a cut using the placed cut guide.

In Example 81, the subject matter of any one or more of Examples 79-80 optionally include performing a tibial cut, using the robotic arm, before performing the soft tissue balancing test while the joint is in extension.

In Example 82, the subject matter of any one or more of Examples 79-81 optionally include wherein calculating the pin placement includes using surgical planning software.

In Example 83, the subject matter of any one or more of Examples 79-82 optionally include wherein the soft tissue balancing component is one of a spike, a condyle pivot, or a j-shaped adapter.

Example 84 is a robotic arm controller comprising: a processor to: receive force data indicative of soft tissue tension in a patient joint during movements of the patient joint by a robotic arm; receive tracking data for the movements of the robotic arm; determine soft tissue tension as a function of joint extension using the tracking data and the force data; and output the soft tissue tension as a function of joint extension.

In Example 85, the subject matter of Example 84 optionally includes wherein the processor is further to calculate a projected soft tissue tension as a function of joint extension using a model of at least one implant at a given location on a bone of the joint, and the actual soft tissue tension as a function of joint extension, wherein the output includes the projected soft tissue tension as a function of joint extension.

In Example 86, the subject matter of Example 85 optionally includes wherein the processor is further to determine alterations required on the bone to receive the at least one implant in the given location, using the model of the implant, wherein the output includes an alteration file for operating a robotized apparatus in effecting the alterations.

In Example 87, the subject matter of any one or more of Examples 84-86 optionally include wherein the processor is further to assess soft-tissue balancing by calculating a rotation of bones of the joints during robot manipulations of the bone.

Example 88 is a CAS controller comprising: a tracking device for producing tracking data representative of bone movements; a range-of-motion (ROM) analysis module configured for receiving tracking data for the bone movements and for determining range of motion and joint laxity data using said tracking data; a soft-tissue balancing module and an implant assessment module configured for updating joint laxity data and calculating resection planes as a function of a model of at least one implant at an adjustable location on a bone of the joint; and an output including the resection planes based on the adjustable location.

Example 89 is a robotic arm comprising: a tracking sensor to output tracking data indicative of movement of the robotic arm, a soft tissue balancing component affixed to an end effector at a distal end of the robotic arm, the soft tissue balancing component configured to apply a force to a bone of a patient joint when the robotic arm is moved in a specified direction; a force sensor to output force data indicative of soft tissue tension in the patient joint when the force is applied to the bone by the soft tissue balancing component; and a processor to: determine soft tissue tension at the patient joint based on the tracking data and the force data; and output the soft tissue tension.

In Example 90, the subject matter of Example 89 optionally includes wherein the soft tissue balancing component includes a spike.

In Example 91, the subject matter of any one or more of Examples 89-90 optionally include wherein the soft tissue balancing component includes a condyle pivot.

In Example 92, the subject matter of any one or more of Examples 89-91 optionally include wherein the soft tissue balancing component is affixed to the robotic arm using a removable pin guide end effector component.

In Example 93, the subject matter of any one or more of Examples 89-92 optionally include wherein the bone is a femur, and wherein the soft tissue balancing component includes a ligament pulling component configured to: snap in place on the end effector; and pull on the femur with a patella in place.

In Example 94, the subject matter of Example 93 optionally includes wherein the processor is to: receive patella location information from a sensor affixed to a back side of the patella; and output the patella location information during a range of motion test.

In Example 95, the subject matter of any one or more of Examples 89-94 optionally include wherein the force is applied while the patient joint is in extension.

In Example 96, the subject matter of any one or more of Examples 89-95 optionally include wherein the force is applied while the patient joint is in flexion.

In Example 97, the subject matter of any one or more of Examples 89-96 optionally include wherein the robotic arm is controlled using a virtual component displayed using an augmented reality device.

In Example 98, the subject matter of any one or more of Examples 89-97 optionally include wherein the soft tissue tension is output to a display device to be displayed on a user interface.

In Example 99, the subject matter of Example 98 optionally includes wherein the user interface is to display varus and valgus angles of the patient joint during a range of motion test.

Example 100 is a method of using a robotic arm to perform soft tissue balancing, the method comprising: tracking, using a processor, movement of the robotic arm to obtain tracking data; applying a force, using a soft tissue balancing component coupled to a distal end of the robotic arm, to a bone of a patient joint; measuring the force to capture data indicative of soft tissue tension in the patient joint when the force is applied to the bone by the soft tissue balancing component; and determining soft tissue tension at the patient joint based on the tracking data and the force data; and outputting the soft tissue tension.

In Example 101, the subject matter of Example 100 optionally includes wherein the soft tissue balancing component includes a spike.

In Example 102, the subject matter of any one or more of Examples 100-101 optionally include wherein the soft tissue balancing component includes a condyle pivot.

In Example 103, the subject matter of any one or more of Examples 100-102 optionally include wherein the soft tissue balancing component is affixed to the robotic arm using a removable pin guide end effector component.

In Example 104, the subject matter of any one or more of Examples 100-103 optionally include wherein the bone is a femur, wherein the soft tissue balancing component includes a ligament pulling component, and further comprising: snapping the ligament pulling component in place on the end effector; and pulling, using the ligament pulling component on the femur with a patella in place.

In Example 105, the subject matter of Example 104 optionally includes receiving patella location information from a sensor affixed to a back side of the patella; and outputting the patella location information during a range of motion test.

In Example 106, the subject matter of any one or more of Examples 100-105 optionally include wherein the force is applied while the patient joint is in extension.

In Example 107, the subject matter of any one or more of Examples 100-106 optionally include wherein the force is applied while the patient joint is in flexion.

In Example 108, the subject matter of any one or more of Examples 100-107 optionally include controlling the robotic arm using a virtual component displayed using an augmented reality device.

In Example 109, the subject matter of any one or more of Examples 100-108 optionally include wherein the soft tissue tension is output to a display device to be displayed on a user interface.

In Example 110, the subject matter of Example 109 optionally includes wherein the user interface is to display varus and valgus angles of the patient joint during a range of motion test.

In Example 111, the subject matter of any one or more of Examples 100-110 optionally include controlling the robotic arm to automatically detect a point on the bone; and registering the point as a landmark using the tracking data.

Example 112 is at least one non-transitory machine-readable medium including instructions for operation of a robotic arm, which when executed by at least one processor, cause the at least one processor to perform operations of any of the methods of Examples 100-111.

Example 113 is a tibial force detection system comprising: a tibial baseplate including a plurality of force sensors to detect forces at corresponding locations of the tibial baseplate; a processor to: receive force information for the corresponding locations from the plurality of force sensors of the tibial baseplate; determine a rotation angle of a femur relative to a tibia based on the force information; and output the rotation angle for display.

Example 114 is a robot-aided surgical system comprising elements of one or more of Examples 1-113.

In Example 115, the subject matter of Example 114 optionally includes performing a tibial cut, using the robotic arm, before performing the soft tissue balancing test while the joint is in extension.

In Example 116, the subject matter of any one or more of Examples 114-115 optionally include wherein the soft tissue balancing component is one of a spike, a condyle pivot, or a j-shaped adapter.

In Example 117, the subject matter of any one or more of Examples 114-116 optionally include wherein the processor is further to calculate a projected soft tissue tension as a function of joint extension using a model of at least one implant at a given location on a bone of the joint, and the actual soft tissue tension as a function of joint extension, wherein the output includes the projected soft tissue tension as a function of joint extension.

In Example 118, the subject matter of Example 117 optionally includes wherein the processor is further to determine alterations required on the bone to receive the at least one implant in the given location, using the model of the implant.

In Example 119, the subject matter of Example 118 optionally includes wherein the output includes an alteration file for operating a robotized apparatus in effecting the alterations.

In Example 120, the subject matter of any one or more of Examples 114-119 optionally include wherein the soft tissue balancing component is affixed to the robotic arm using a removable pin guide end effector component.

In Example 121, the subject matter of any one or more of Examples 114-120 optionally include wherein the soft tissue balancing component includes a j-shaped arm to couple to a femoral spike to allow for performance of the soft tissue balancing test with a patella in place.

In Example 122, the subject matter of Example 121 optionally includes wherein the processor is to: receive patella location information from a sensor affixed to a back side of the patella; and output the patella location information during a range of motion test.

In Example 123, the subject matter of any one or more of Examples 114-122 optionally include wherein the robotic arm is controlled using a virtual component displayed using an augmented reality device.

In Example 124, the subject matter of any one or more of Examples 114-123 optionally include wherein the soft tissue tension is output to a display device to be displayed on a user interface.

In Example 125, the subject matter of Example 124 optionally includes wherein the user interface is to display varus and valgus angles of the patient joint during a range of motion test.

In Example 126, the subject matter of any one or more of Examples 114-125 optionally include controlling the robotic arm to automatically detect a point on the bone; and registering the point as a landmark using the tracking data.

In Example 127, the subject matter of Example 126 optionally includes using the landmark to determine the tension in the soft tissue during a soft tissue balancing test.

In Example 128, the subject matter of any one or more of Examples 114-127 optionally include a removable holder, which when coupled to an end effector of the robotic arm, creates an anchor to receive a spike, the spike configured to couple the end effector to the bone.

In Example 129, the subject matter of any one or more of Examples 114-128 optionally include an attachment to couple to an end effector of the robotic arm, the attachment comprising a spike, a J-hook, or an L-hook.

In Example 130, the subject matter of any one or more of Examples 114-129 optionally include a spreader attached to a distal end of the robotic arm, the spreader configured to mechanically distract the first bone from the second bone in the joint to perform the soft tissue balancing test.

In Example 131, the subject matter of Example 130 optionally includes wherein the spreader includes a gear or a long lever arm to assist in mechanically distracting the first bone from the second bone.

In Example 132, the subject matter of any one or more of Examples 114-131 optionally include a processor to determine whether the soft tissue is in balance using information from a preoperative plan or image.

In Example 133, the subject matter of any one or more of Examples 114-132 optionally include wherein range of motion is tested postoperatively to determine success of the soft tissue balancing test.

Example 134 is at least one non-transitory machine-readable medium including instructions for operation of a robotic arm, which when executed by at least one processor, cause the at least one processor to perform operations of any of the methods of Examples 1-133.

Example 135 is a method for performing any one of examples 1-133.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

What is claimed is:

1. A robot-aided surgical system comprising:
a processor;
a display device; and
memory, including instructions, which when executed by the processor, cause the processor to:
   receive an indication that a first surgical step has been completed on a patient by a robotic arm;
   automatically cause the robotic arm to perform an intraoperative orthopedic assessment for the patient;
   output for display, on a user interface of the display device, information related to the intraoperative orthopedic assessment;
   determine whether the intraoperative orthopedic assessment has been completed; and
   output for display, on the user interface in response to determining that the orthopedic assessment has been completed, information corresponding to a second surgical step based on results of the intraoperative orthopedic assessment.

2. The robot-aided surgical system of claim 1, further comprising displaying the indication on the user interface.

3. The robot-aided surgical system of claim 1, wherein the intraoperative orthopedic assessment includes a soft tissue balancing test or an implant assessment.

4. The robot-aided surgical system of claim 1, wherein displaying the information corresponding to the second surgical step includes displaying a bone model and an implant as a 3D representation, the 3D representation including selectable views including at least one of a flexion, extension, frontal plane, sagittal plane, or axial plane view.

5. The robot-aided surgical system of claim 1, wherein the information corresponding to the second surgical step includes a proposed implant model.

6. The robot-aided surgical system of claim 1, further comprising:
receiving a change to a planned implant model; and
modifying a displayed joint line based on the change.

7. The robot-aided surgical system of claim 1, wherein displaying the information related to the intraoperative orthopedic assessment includes displaying a gap distance, a current femur or tibia/valgus angle, or an anterior gap for patellofemoral joint stuffing.

8. The robot-aided surgical system of claim 1, wherein the first surgical step includes a resection.

9. The robot-aided surgical system of claim 1, wherein the second surgical step is to be performed by the robotic arm.

10. A robot-aided surgical method comprising:
receiving, at a processor, an indication that a first surgical step has been completed on a patient by a robotic arm;
automatically causing the robotic arm to perform an intraoperative orthopedic assessment for the patient;
displaying, on a user interface of a display device, information related to the intraoperative orthopedic assessment;
determining whether the intraoperative orthopedic assessment has been completed; and
displaying, on the user interface in response to determining that the intraoperative orthopedic assessment has been completed, information corresponding to a second surgical step based on results of the intraoperative orthopedic assessment.

11. The robot-aided surgical method of claim 10, further comprising displaying the indication on the user interface.

12. The robot-aided surgical method of claim 10, wherein the intraoperative orthopedic assessment includes a soft tissue balancing test or an implant assessment.

13. The robot-aided surgical method of claim 10, wherein displaying the information corresponding to the second surgical step includes displaying a bone model and an implant as a 3D representation, the 3D representation including selectable views including at least one of a flexion, extension, frontal plane, sagittal plane, or axial plane view.

14. The robot-aided surgical method of claim 10, wherein the information corresponding to the second surgical step includes a proposed implant model.

15. The robot-aided surgical method of claim 10, further comprising:
receiving a change to a planned implant model; and
modifying a displayed joint line based on the change.

16. The robot-aided surgical method of claim 10, wherein displaying the information related to the intraoperative orthopedic assessment includes displaying a gap distance, a current femur or tibia/valgus angle, or an anterior gap for patellofemoral joint stuffing.

17. The robot-aided surgical method of claim 10, wherein the first surgical step includes a resection.

18. The robot-aided surgical method of claim 10, wherein the second surgical step is to be performed by the robotic arm.

19. At least one non-transitory machine-readable medium including instructions, which when executed by processing circuitry, cause the processing circuitry to perform operations to:
receive an indication that a first surgical step has been completed on a patient by a robotic arm;
automatically cause the robotic arm to perform an intraoperative orthopedic assessment for the patient;
output for display, on a user interface of a display device, information related to the intraoperative orthopedic assessment;
determine whether the intraoperative orthopedic assessment has been completed; and
output for display, on the user interface in response to determining that the intraoperative orthopedic assessment has been completed, information corresponding to a second surgical step based on results of the intraoperative orthopedic assessment.

20. The at least one machine-readable medium of claim 19, wherein the intraoperative orthopedic assessment includes a soft tissue balancing test or an implant assessment.

* * * * *

UNITED STATES PATENT AND TRADEMARK OFFICE
CERTIFICATE OF CORRECTION

| | | |
|---|---|---|
| PATENT NO. | : 12,364,544 B2 | Page 1 of 1 |
| APPLICATION NO. | : 17/469415 | |
| DATED | : July 22, 2025 | |
| INVENTOR(S) | : Couture et al. | |

It is certified that error appears in the above-identified patent and that said Letters Patent is hereby corrected as shown below:

On the Title Page

Item (72), in "Inventors", in Column 1, Line 6, delete "Marseilles" and insert --Marseille-- therefor On page 3, in Column 1, under Item (56), "Other Publications", Line 26, delete "Jul. 16, 2018"," and insert --Jul. 06, 2018",-- therefor In the Claims In Column 43, Line 17, in Claim 1, before "orthopedic", insert --intraoperative--

Signed and Sealed this
Eleventh Day of November, 2025

John A. Squires
*Director of the United States Patent and Trademark Office*